US009737545B2

(12) United States Patent
McCauley et al.

(10) Patent No.: US 9,737,545 B2
(45) Date of Patent: Aug. 22, 2017

(54) HIV PROTEASE INHIBITORS

(71) Applicants: MERCK SHARP & DOHME CORP., Rahway, NJ (US); MERCK CANADA INC., Kirkland (CA)

(72) Inventors: John A. McCauley, Maple Glen, PA (US); Christian Beaulieu, Laval (CA); David Jonathan Bennett, Boston, MA (US); Christopher J. Bungard, Lansdale, PA (US); Sheldon Crane, Ile Perrot (CA); Thomas J. Greshock, Collegeville, PA (US); Katharine M. Holloway, Lansdale, PA (US); Helen Juteau, Ville St-Laurent (CA); Daniel McKay, Milton, MA (US); Carmela Molinaro, Rahway, NJ (US); Oscar Miguel Moradei, Kirkland (CA); Christian Nadeau, Montreal (CA); Daniel Simard, Montreal (CA); Satyanarayana Tummanapalli, Singapore Science Park III (SG); Vouy Linh Truong, Pierrefonds (CA); Karine M. Villeneuve, Montreal (CA); Peter D. Williams, Harleysville, PA (US)

(73) Assignees: Merck Sharp & Dohme Corp., Rahway, NJ (US); Merck Canada Inc., Kirkland, Quebec (CA)

(*) Notice: Subject to any disclaimer, the term of this patent is extended or adjusted under 35 U.S.C. 154(b) by 0 days.

(21) Appl. No.: 15/104,782

(22) PCT Filed: Dec. 17, 2014

(86) PCT No.: PCT/US2014/070725
§ 371 (c)(1),
(2) Date: Jun. 15, 2016

(87) PCT Pub. No.: WO2015/095265
PCT Pub. Date: Jun. 25, 2015

(65) Prior Publication Data
US 2016/0296527 A1    Oct. 13, 2016

Related U.S. Application Data

(60) Provisional application No. 61/918,013, filed on Dec. 19, 2013.

(51) Int. Cl.
*A61K 31/5377* (2006.01)
*C07D 417/04* (2006.01)
*A61K 45/06* (2006.01)
*C07D 487/04* (2006.01)
*C07D 471/04* (2006.01)
*C07D 413/04* (2006.01)
*C07D 265/30* (2006.01)
*C07D 413/14* (2006.01)

(52) U.S. Cl.
CPC ......... *A61K 31/5377* (2013.01); *A61K 45/06* (2013.01); *C07D 265/30* (2013.01); *C07D 413/04* (2013.01); *C07D 413/14* (2013.01); *C07D 417/04* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 5,196,438 A | 3/1993 | Martin et al. |
| 5,413,999 A | 5/1995 | Vacca et al. |
| 5,484,801 A | 1/1996 | Al-Razzak et al. |
| 5,484,926 A | 1/1996 | Dressman et al. |
| 5,852,195 A | 12/1998 | Romines et al. |
| 5,858,397 A | 1/1999 | Lim et al. |
| 8,497,383 B2 | 7/2013 | Coburn et al. |
| 9,315,475 B2 | 4/2016 | Beaulieu et al. |
| 2009/0036422 A1 | 2/2009 | Knust et al. |
| 2009/0306141 A1 | 12/2009 | Eriksson et al. |
| 2013/0158020 A1 | 6/2013 | Deng et al. |
| 2014/0018325 A1 | 1/2014 | Boyd et al. |
| 2014/0018326 A1 | 1/2014 | Moradei et al. |
| 2014/0303171 A1 | 10/2014 | Boyd et al. |

FOREIGN PATENT DOCUMENTS

| | | |
|---|---|---|
| WO | 0138332 A1 | 5/2001 |
| WO | 0230930 A2 | 4/2002 |
| WO | 2004045347 A2 | 7/2004 |

(Continued)

OTHER PUBLICATIONS

Database CAPLUS in STN, Acc. No. 2013:159376, Xia et al., WO 2013013640 A1 (Jan. 31, 2013) (abstract).*
Daniel E. Patterson, et al, "Developement of a Practical Large-Scale Synthesis of Denagliptin Tosylate", Drganic Process Research & Dev., 2009, pp. 900-906, vol. 13.
Joseph P. Vacca, et al, "L-735,524: An Orally Bioavailable Human Immunodeficiency Virus Type 1 Protease Inhibitor", Proc. Natl. Acad. Sci., Apr. 1994, pp. 4096-4100, vol. 91.

(Continued)

*Primary Examiner* — Brian J Davis
(74) *Attorney, Agent, or Firm* — Carol S. Quagliato; Catherine D. Fitch

(57) ABSTRACT

The present invention is directed to 5-heteroarylmorpholine derivatives and their use in the inhibition of HIV protease, the inhibition of HIV replication, the prophylaxis of infection by HIV, the treatment of infection by HIV, and the prophylaxis, treatment, and delay in the onset or progression of AIDS. The compounds and their salts can be employed as ingredients in pharmaceutical compositions, optionally in combination with other antivirals, immunomodulators, antibiotics or vaccines.

15 Claims, No Drawings

(56) References Cited

FOREIGN PATENT DOCUMENTS

| WO | 2009042094 A2 | 4/2009 |
|---|---|---|
| WO | 2009042943 A1 | 4/2009 |
| WO | 2012030685 A2 | 3/2012 |
| WO | 2012116440 A1 | 9/2012 |
| WO | 2013019635 A1 | 2/2013 |
| WO | 2015017393 A1 | 2/2015 |
| WO | 2015096276 A1 | 6/2015 |
| WO | 2015134366 A1 | 9/2015 |
| WO | 2015138220 A1 | 12/2015 |

OTHER PUBLICATIONS

Joel R. Huff, "HIV Protease: A Novel Chemotherapeutic Target for AIDS", Journal of Medicinal Chemistry, 1991, pp. 2305-2314, vol. 34, No. 8.

Nancy E. Kohl, et al, "Active Human Immunodeficiency Virus Protease Is Required for Viral Infectivity", Proc. Natl. Acad. Sci., 1988, pp. 4686-4690, vol. 85.

Laurence H. Pearl, et al, "A Structural Model for the Retroviral Proteases", Nature, 1987, pp. 351-354, vol. 329.

Michael D. Power, et al, "Nucleotide Sequence of SRV-1, a Type D Simian", Science, 1986, pp. 1567-1572, vol. 231.

Lee Ratner, et al, "Complete Nucleotide Sequence of AIDS Virus, HTLV-III", Nature, 1985, pp. 277-284, vol. 313.

Roy M. Gulick, et al, "Treatment With Indinavir, Zidovudine, and Lamivudine in Adults With Human Immunodeficiency Virus Infection and Prior Antiretroviral Therapy", New England Journal of Medicine, 1997, pp. 734-739, vol. 337.

Scott M. Hammer, et al, "A Controlled Trial of Two Nucleoside Analogues Plus Indinavir in Persons With Human Immunodeficiency Virus Infection and CD4 Cell Counts of 200 Per Cubic Millimeter or Less", The New England Journal of Medicine, 1997, pp. 725-733, vol. 337, No. 11.

Hiroyuki Toh, et al, "Close Structural Resemblance Between Putative Polymerase of a *Drosophila* Transposable Genetic Element 17.5 and Pol Gene Product of Moloney Murine Leukaemia Virus", The EMBO Journal, 1985, pp. 1267-1272, vol. 4, No. 5.

* cited by examiner

HIV PROTEASE INHIBITORS

RELATED APPLICATIONS

This application is a 35 U.S.C. §371 filing from International Application No. PCT/US2014/070725, filed Dec. 17, 2014, which claims the benefit of U.S. Provisional Application No. 61/918,013, filed Dec. 19, 2013. Each of the aforementioned applications is herein incorporated by reference in its entirety.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus.

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Furthermore, the currently available protease inhibitors are rapidly metabolized and cleared from the bloodstream, requiring frequent dosing and use of a boosting agent. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

SUMMARY OF THE INVENTION

The present invention is directed to 5-heteroarylmorpholine derivatives and their use in the inhibition of HIV protease, the inhibition of HIV replication, the prophylaxis of infection by HIV, the treatment of infection by HIV, and the prophylaxis, treatment, and delay in the onset or progression of AIDS.

DETAILED DESCRIPTION OF THE INVENTION

The invention encompasses a genus of compounds of Formula I:

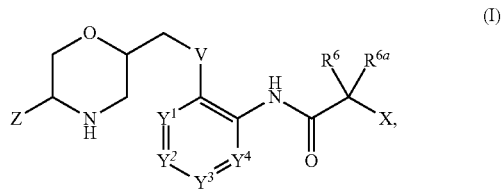

or a pharmaceutically acceptable salt thereof, wherein:
V is $CH_2$ or O;
$Y^1$, $Y^2$, $Y^3$ and $Y^4$ are independently selected from C(R) and N;
X is selected from H and $NR^7R^8$;
R is selected from H, halo, hydroxy, $C_{1-4}$alkyl, $C_{1-4}$alkoxy, $C_{1-4}$alkyl-$S(O)_k$—, $CF_3$, CN, and benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, $C_{1-4}$alkyl, $C_{1-4}$alkoxy, $CF_3$ and CN;
each k is independently 0, 1 or 2;
Z is HetA;
$R^6$ is selected from:

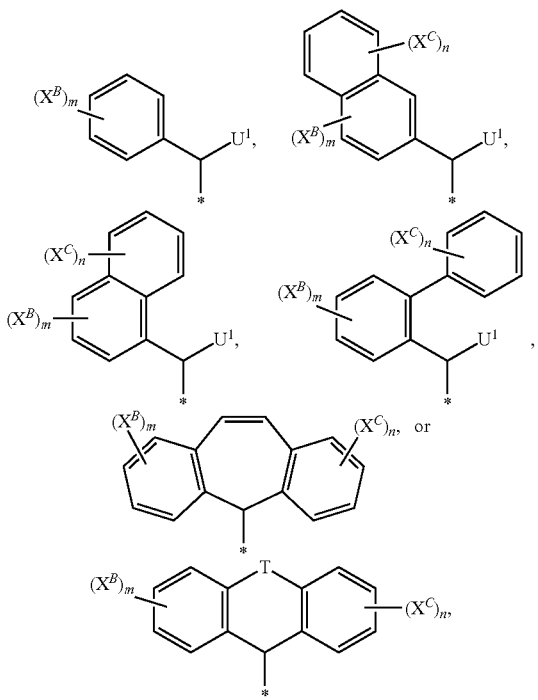

-continued

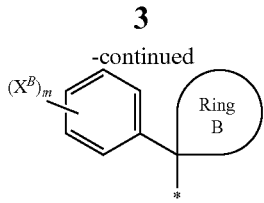

wherein the asterisk (*) denotes the point of attachment to the rest of the compound and $U^1$ is selected from (1) H, (2) $C_{1-10}$alkyl, wherein said $C_{1-10}$alkyl is optionally substituted with 1 to 4 substituents independently selected from halogen, $C_{1-4}$alkyl, $C_{1-4}$haloalkyl, hydroxy and $C_{1-4}$alkoxy, (3) $C_{3-7}$ cycloalkyl, wherein said $C_{3-7}$ cycloalkyl is optionally substituted with 1 to 4 substituents independently selected from halogen, $C_{1-4}$alkyl, $C_{1-4}$haloalkyl, hydroxy and $C_{1-4}$alkoxy, (4) ArylA, (5) HetA, (6) HetB, (7) $C_{1-10}$alkyl substituted with ArylA, (8) $C_{1-10}$alkyl substituted with HetA, and (9) $C_{1-10}$alkyl substituted with HetB; and Ring B is selected from $C_{3-7}$ cycloalky and HetB, wherein $C_{3-7}$ cycloalkyl is optionally substituted with 1 to 4 substituents independently selected from halogen, OH, $C_{1-4}$alkyl, $C_{1-4}$fluorolkyl and $C_{1-4}$alkoxy;

$R^{6A}$ is selected from H or $C_{1-6}$ alkyl;

each $X^B$, each $X^C$, each $Y^B$ and each $Y^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) C(O)$NH_2$,
(25) C(O)N(H)—$C_{1-6}$ alkyl,
(26) C(O)N(—$C_{1-6}$ alkyl)$_2$,
(27) C(O)N(H)C(O)—$C_{1-6}$ alkyl,
(28) C(O)N(H)CH(O)
(29) $SO_2$H,
(30) $SO_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or —$CH_2$-HetA, optionally substituted with 1 to 5 substituents selected from halogen and $C_{1-6}$ alkyl,
(33) trimethylsilyl, and
(34) $C_{2-6}$alkenyl,
wherein $C_{1-6}$ alkyl in each instance of (1), (3) (5), (6), (9), (10), (16), (17), (18), (21), (23), (25), (26), (27), (30),
(31) and (32) above is optionally substituted with 1 to 6 substituents as allowed by valence selected from the group consisting of:
(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) $NO_2$,
(k) $NH_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) $SO_2$—$C_{1-6}$ alkyl;
T is O, S, S(O), or $SO_2$;
m is an integer equal to 0, 1, 2, or 3;
n is an integer equal to 0, 1, 2, or 3;
$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or $SO_2$—$R^K$;
$R^8$ is H, $C_{1-6}$ alkyl, $C_{1-6}$ haloalkyl or $C_{3-6}$ cycloalkyl;
$R^K$ is:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) $C_{1-6}$ alkyl substituted with C(O)O—$C_{1-6}$ alkyl,
(9) $C_{1-6}$ alkyl substituted with C(O)OH,
(10) $C_{1-6}$ alkyl substituted with C(O)—$C_{1-6}$ alkyl,
(11) N(H)—$C_{1-6}$ alkyl,
(12) N(—$C_{1-6}$ alkyl)$_2$,
(13) $C_{1-6}$ alkyl substituted with $NH_2$, N(H)—$C_{1-6}$ alkyl, or N(—$C_{1-6}$ alkyl)$_2$,
(14) AryA,
(15) $C_{1-6}$ alkyl substituted with AryA,
(16) O—$C_{1-6}$ alkyl substituted with AryA,
(17) HetA,
(18) $C_{1-6}$ alkyl substituted with HetA,
(19) O—$C_{1-6}$ alkyl substituted with HetA,
(20) HetB,
(21) O-HetB, or
(22) O—$C_{1-6}$ alkyl substituted with HetB;
each Aryl A is an aryl which is independently phenyl or naphthyl, wherein the phenyl or naphthyl is optionally substituted with $Y^B$ from one up to the maximum number of substitutable positions as allowed by valence;
each HetA is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with $Y^C$ from one up to the maximum number of substitutable positions as allowed by valence; and
each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with one or more substituents, up to the maximum number allowed by valance, each of which is independently halogen, CN, C$_{1-6}$ alkyl, OH, oxo, O—C$_{1-6}$ alkyl, C$_{1-6}$ haloalkyl, O—C$_{1-6}$ haloalkyl, C(O)NH$_2$, C(O)N(H)—C$_{1-6}$ alkyl, C(O)N(—C$_{1-6}$ alkyl)$_2$, C(O)H, C(O)—C$_{1-6}$ alkyl, CO$_2$H, CO$_2$—C$_{1-6}$ alkyl, SO$_2$H, or SO$_2$—C$_{1-6}$ alkyl.

Another embodiment of the invention encompasses compounds of Formula I as described in the genus above, wherein each X$^B$, each X$^C$, each Y$^B$ and each Y$^C$ are selected from the substituents (1) to (34) as described in the genus, except that C$_{1-6}$ alkyl in each instance of (1), (3) (5), (6), (9), (10), (16), (17), (18), (21), (23), (25), (26), (27), (30), (31) and (32) is unsubstituted.

Within the genus, the invention encompasses a first sub-genus of compounds of Formula I wherein R$^6$ is:

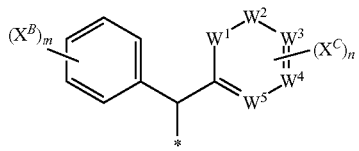

wherein W$^1$ to W$^5$ are independently CH or N, with the proviso that no more than three are N, and R$^{6A}$ is H. X$^B$ and X$^C$ may be substituted on any substitutable position including, for X$^C$, W$^1$ to W$^5$ when any of the aforementioned are CH.

Also within the genus, the invention encompasses a second sub-genus of compounds of Formula I of Formula Ia

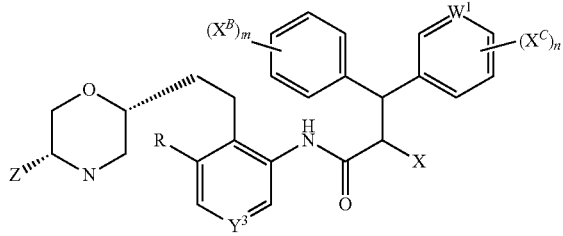

(Ia)

or a pharmaceutically acceptable salt thereof, wherein W$^1$ is CH or N, and all other variables are as provided in the genus. X$^B$ and X$^C$ may be substituted on any substitutable position including, for X$^C$, W$^1$ when W$^1$ is CH.

Within the second sub-genus, the invention encompasses a first class of compounds of Formula Ia wherein:
R is H or fluoro,
Y$^3$ is CH or N,
X$^B$ and X$^C$ are independently selected from F, Cl, Br, —OCH$_3$, —CF$_3$ and —OCF$_3$, and
m and n are independently 0, 1 or 2.

The invention encompasses a first sub-class of compounds of Formula Ia wherein X is selected from: H, —NH$_2$ and —N(H)—C(O)—OR$^8$, and all other variables are as provided in the second sub-genus or first class. The invention encompasses a group of compounds of Formula Ia wherein W$^1$ is CH, one X$^B$ group is present and substituted at the 4-position, one or two X$^C$ groups are present and substituted at the 3- or 3,5-positions respectively, and the X$^B$ group is a different group with respect to either X$^C$ group,
and all other variables are as provided in the second sub-genus, first class or first sub-class.

Also within the genus, the invention encompasses a third sub-genus of compounds of Formula I of Formula Ib

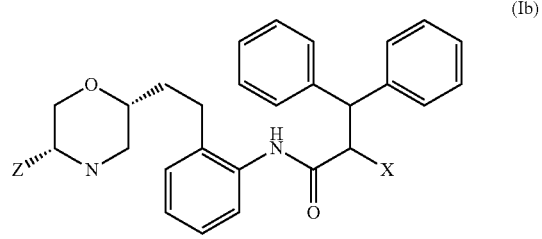

(Ib)

or a pharmaceutically acceptable salt thereof, wherein X is selected from: —NH$_2$ and —N(H)—C(O)—OR$^8$, and all other variables are defined as in the genus.

Within the third sub-genus, the invention encompasses a second class of compounds of Formula Ib wherein Z is selected from

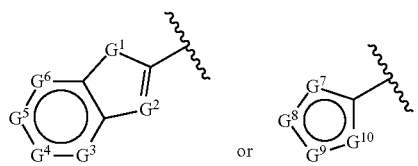

wherein
G$^1$ is selected from O, S, N(R$^9$) and C(R$^9$)(R$^{10}$);
G$^2$, G$^3$, G$^4$, G$^5$ and G$^6$ are independently selected from N and C(R$^9$);
G$^7$, G$^8$, G$^9$ and G$^{10}$ are independently selected from N and C(R$^9$), or O, S, N(R$^9$) and C(R$^9$)(R$^{10}$), in accordance with the valency;
wherein the selection of G$^1$ to G$^{10}$ results in a stable aromatic group Z,
and wherein R$^9$ and R$^{10}$ are independently selected from the group consisting of:
(1) C$_{1-6}$ alkyl,
(2) C$_{3-6}$ cycloalkyl,
(3) C$_{1-6}$ haloalkyl,
(4) OH,
(5) O—C$_{1-6}$ alkyl,
(6) O—C$_{1-6}$ haloalkyl,
(7) O—C$_{3-6}$ cycloalkyl,
(8) SH,
(9) S—C$_{1-6}$ alkyl,
(10) S—C$_{1-6}$ haloalkyl,
(11) S—C$_{3-6}$ cycloalkyl,
(12) halo,
(13) CN,
(14) NO$_2$,
(15) NH$_2$,
(16) N(H)—C$_{1-6}$ alkyl,
(17) N(—C$_{1-6}$ alkyl)$_2$,
(18) N(H)C(O)—C$_{1-6}$ alkyl,
(19) N(H)CH(O),
(20) CH(O),
(21) C(O)—C$_{1-6}$ alkyl,
(22) C(O)OH,
(23) C(O)O—C$_{1-6}$ alkyl,
(24) C(O)NH$_2$,

(25) C(O)N(H)—$C_{1-6}$ alkyl,
(26) C(O)N(—$C_{1-6}$ alkyl)$_2$,
(27) C(O)N(H)C(O)—$C_{1-6}$ alkyl,
(28) C(O)N(H)CH(O)
(29) SO$_2$H,
(30) SO$_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or —CH$_2$-HetA, optionally substituted with 1 to 5 substituents selected from halogen and $C_{1-6}$ alkyl,
(33) trimethylsilyl, and
(34) $C_{2-6}$alkenyl,
wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) NO$_2$,
(k) NH$_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) SO$_2$—$C_{1-6}$ alkyl,
or $R^9$ and $R^{10}$ on the same atom may be joined together to form carbonyl Another embodiment of the invention encompasses compounds of Formula Ib as described in the second class above, wherein $R^9$ and $R^{10}$ are selected from the substituents (1) to (34) as described in the second class, except that $C_{1-6}$ alkyl in each instance of (1), (3) (5), (6), (9), (10), (16), (17), (18), (21), (23), (25), (26), (27), (30), (31) and (32) is unsubstituted.

Within the second class, the invention encompasses a second sub-class of compounds of Formula Ib wherein $R^9$ and $R^{10}$ are independently selected from the group consisting of: $C_{1-4}$ alkyl, $C_{1-6}$ haloalkyl, OH, O—$C_{1-6}$ alkyl, halo, CN, SO$_2$—$C_{1-6}$ alkyl, phenyl and benzyl.

Within the second sub-class, the invention encompasses a group of compounds wherein Z is selected from benzimidazolyl, imidazolyl, triazolyl, tetrazolyl, oxadiazolyl, indolyl and pyrrolopyrdidinyl, wherein Z is optionally substituted from one up to the maximum number of substitutable positions as allowed by valence with one or more substituents selected from $C_{1-4}$ alkyl, $C_{1-6}$ haloalkyl, OH, O—$C_{1-6}$ alkyl, halo, CN, SO$_2$—$C_{1-6}$ alkyl, phenyl and benzyl.

The present invention includes compounds of Formula I above and pharmaceutically acceptable salts thereof.

Compounds of Formula Ia and Ib form a subset of the compounds included in Formula I. Any description which follows that refers to a compound of Formula I also applies to a compound of Formula Ia and Ib.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c), (d) or (e) or the combination of or (f) or (g).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

The term "aryl" refers to phenyl and naphthyl. The aryl of particular interest is phenyl.

The term "heteroaryl" refers to (i) a 5- or 6-membered heteroaromatic ring containing from 1 to 3 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention (see HetB) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^B$ or $X^C$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and encompasses both the keto and enol forms of a compound when conversion is possible.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for reduced likelihood of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (e.g., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following routes: orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in Remington's Pharmaceutical Sciences, 18$^{th}$ edition, edited by A. R. Gennaro, Mack Publishing Co., 1990 and in Remington—The Science and Practice of Pharmacy, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the inhibition of HIV replication, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |

TABLE A-continued

Antiviral Agents for Treating HIV infection or AIDS

| Name | Type |
|---|---|
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), or the 59$^{th}$ edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be used for these purposes.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Abbreviations employed herein include the following: Bn=benzyl; BOC (or Boc)=t-butyloxycarbonyl; Boc$_2$O=di-t-butyl carbonate; BOP=benzotriazol-1-yloxytris-(dimethylamino)phosphonium; BSA=bovine serum albumin; CBS=Corey, Bakshi, Shibata chiral oxazaborolidine mediated ketone reduction; Cbz=benzyloxycarbonyl; DBU=1,8-diazabicyclo[5.4.0]undec-7-one; DCAD=di-(4-chlorobenzyl) azodicarboxylate; DCE=1,2-dichloroethane; DCM=dichloromethane; DEAD=diethyl azodicarboxylate; DIAD=diisopropylazodicarboxylate; Dibal-H=diisobutylaluminum hydride; DMAP=4-dimethylaminopyridine; DMF=dimethylformamide; DMSO=dimethyl sulfoxide; EDC=1-ethyl-3-(3-dimethylaminopropyl) carbodiimide; Et=ethyl; EtOAc=ethyl acetate; EtOH=ethanol; G-2G=Grubbs catalyst, 2$^{nd}$ generation; HOAt=1-hydroxy-7-azabenzotriazole; HPLC=high performance liquid chromatography; HSU=hydroxysuccinimide; i-PrOH=isopropanol; LAH=lithium aluminum hydride; LC-MS=liquid chromatography-mass spectroscopy; Me=methyl; MeOH=methanol; MOC=methoxycarbonyl; Ms=mesyl or methanesulfonyl; NMR=nuclear magnetic resonance; Ph=phenyl; RCM=ring closing metathesis; Piv=pivaloyl; PPTS=pyridinium p-toluene sulfonate; PyBrOP=bromo-tris-pyrrolidinophosphonium hexafluorophosphate; SCX=strong cation exchange resin; STP=standard temperature and pressure (i.e., 25° C. & 1 atmosphere); TBS=tert-butyldimethylsilyl; TBDPS=tert-butyl(diphenyl) silyl; TBDPSCl=tert-butyl(dimethyl)silyl chloride; TEA=triethylamine; TFA=trifluoroacetic acid; THF=tetrahydrofuran; TLC=thin layer chromatography; TMAF=tetramethyl ammonium fluoride; TMSCHN$_2$=trimethylsilyl diazomethane; TPAP=tetrapropylammonium perruthenate; TPP=triphenylphosphine.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl optionally substituted with one or more X$^4$. In the examples that follow, when a nitrogen atom is depicted without the necessary hydrogen atoms to complete the valence, it is assumed those nitrogen atoms are present unless specifically depicted to the contrary.

Example 1

N-(2-{2-[(2R,5R)-5-(1H-benzimidazol-2-yl)morpholin-2-yl]ethyl}phenyl)-Nα-(methoxycarbonyl)-β-phenyl-L-phenylalaninamide

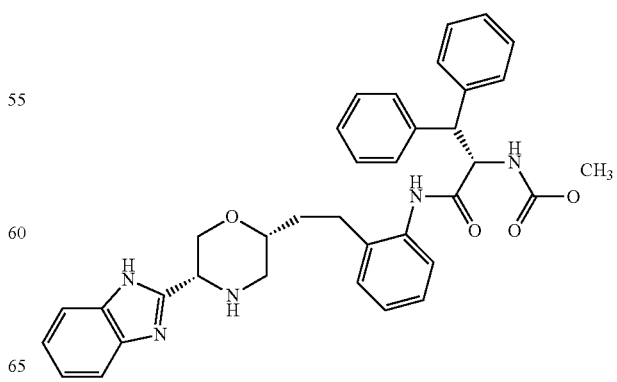

Step 1: methyl N-benzyl-D-serinate

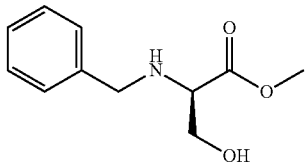

To (2R)-3-hydroxy-1-methoxy-1-oxopropan-2-aminium chloride (1 eq.) in MeOH (1.3 M) at 0° C. was added triethylamine (1 eq.). The reaction mixture was stirred for 10 minutes and benzaldehyde (1 eq) was added. The reaction mixture was stirred for 2 hours and $NaBH_4$ (1.5 eq.) was added portionwise to the reaction mixture over 30 min. The reaction mixture was stirred at rt for 5 hours and poured into a 1:1 mixture of saturated aqueous $NH_4Cl$ and EtOAc. The aqueous layer was extracted with EtOAc and the combined organic layers were washed with brine and water, dried over $Na_2SO_4$, filtered and concentrated. The crude product was used as such for the next step.

Step 2: methyl N-benzyl-O-[tert-butyl(dimethyl)silyl]-D-serinate

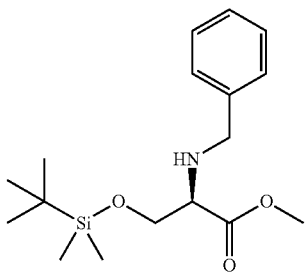 [SMILES: COC(=O)[C@@H](CO[Si](C)(C)C(C)(C)C)NCc1ccccc1]

To methyl N-benzyl-D-serinate (1 eq.) in $CH_2Cl_2$ (0.3 M) at rt were added triethylamine (1 eq) and DMAP (0.05 eq). The reaction mixture was cooled to 0° C. and TBS-Cl (1.1 eq) was added. The reaction mixture was stirred at rt for 16 hrs, water was added and the aqueous layer was extracted with $CH_2Cl_2$. The combined organic layers were washed with saturated aqueous $NH_4Cl$, dried over $Na_2SO_4$, filtered and concentrated. The crude product was used as such for the next step.

Step 3: (2S)-2-(benzylamino)-3-{[tert-butyl(dimethyl)silyl]oxy}propan-1-ol

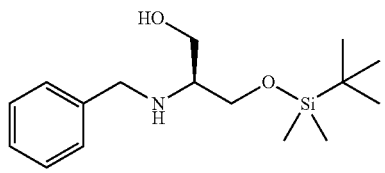 [SMILES: CC(C)(C)[Si](C)(C)OC[C@H](CO)NCc1ccccc1]

To methyl N-benzyl-O-[tert-butyl(dimethyl)silyl]-D-serinate (1 eq.) in THF (0.4 M) at rt were added 2M $LiBH_4$ in THF (1.2 eq.) and MeOH (1.2 eq). The mixture was stirred at rt for 16 hrs and quenched by the slow addition of saturated aqueous $NH_4Cl$. The aqueous layer was extracted with EtOAc. The combined organic layers were dried over $Na_2SO_4$, filtered and concentrated. The crude product was used as such for the next step.

Step 4: [(2S,5S)-4-benzyl-5-({[tert-butyl(dimethyl)silyl]oxy}methyl)morpholin-2-yl]methanol

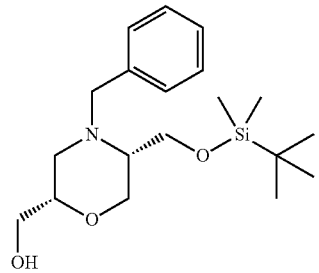 [SMILES: CC(C)(C)[Si](C)(C)OC[C@@H]1CO[C@H](CO)CN1Cc1ccccc1]

To (2S)-2-(benzylamino)-3-{[tert-butyl(dimethyl)silyl]oxy}propan-1-ol (1 eq) in Toluene (0.3 M) at rt was added (R)-(-)-epichlorohydrin (1.3 eq.) and Lithium perchlorate (1.3 eq) was then slowly added over 2 hours. The mixture was stirred at rt for 48 hrs and sodium methoxide (2.5 eq of a 25% solution of NaOMe in MeOH) was added. MeOH was then added to the reaction mixture to obtain a 4:1 ratio of toluene:MeOH as solvent. The reaction mixture was stirred for 48 hrs at rt and diluted with saturated aqueous $NH_4Cl$. The aqueous layer was extracted with EtOAc. The combined organic layers were washed with brine, dried over $Na_2SO_4$, filtered and concentrated. The crude product was purified by automated $SiO_2$ flash chromatography system using solvent gradient of 0% EtOAc/Hex to 25% EtOAc/Hex to afford the desired compound.

Step 5: tert-butyl (2S,5S)-5-({[tert-butyl(dimethyl)silyl]oxy}methyl)-2-(hydroxymethyl)morpholine-4-carboxylate

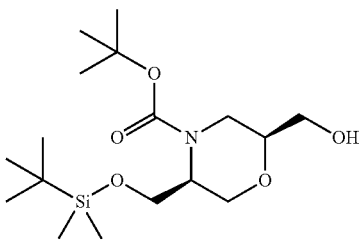 [SMILES: CC(C)(C)OC(=O)N1C[C@@H](CO)OC[C@H]1CO[Si](C)(C)C(C)(C)C]

To ethyl [(2S,5S)-4-benzyl-5-({[tert-butyl(dimethyl)silyl]oxy}methyl)morpholin-2-yl]methanol (1 eq.) in EtOH (0.4 M) at rt were added $Boc_2O$ (1.2 eq), triethylamine (1 eq) and 20% $Pd(OH)_2$ (0.2 eq.). The reaction was degassed and then shaken in a parr apparatus under 45 psi of $H_2$ for 16 hrs. The reaction mixture was filtered on celite and concentrated. The residue was diluted in EtOAc and the organic layer was washed with water and brine, dried over $Na_2SO_4$, filtered and concentrated. The crude product was used as such for the next step.

Step 6: tert-butyl (2S,5S)-5-({[tert-butyl(dimethyl)silyl]oxy}methyl)-2-formylmorpholine-4-carboxylate

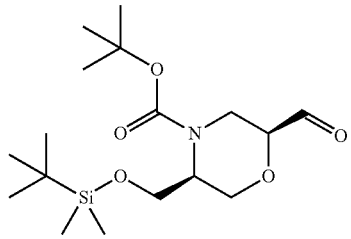 [SMILES: CC(C)(C)OC(=O)N1C[C@@H](C=O)OC[C@H]1CO[Si](C)(C)C(C)(C)C]

To a stirred solution of oxalyl chloride (2 eq) in DCM (0.3 M) at −78° C. was added a solution of DMSO (5 eq) in DCM (0.5M). The reaction mixture was stirred at −78° C. for 30 min. A solution of tert-butyl (2S,5S)-5-({[tert-butyl(dimethyl)silyl]oxy}methyl)-2-(hydroxymethyl)morpholine-4-carboxylate (1 eq) in CH$_2$Cl$_2$ (0.2M) was added dropwise and stirred at −40° C. for 1.5 hours. It was then cooled to −78° C. and triethylamine (7 eq) was added and the reaction mixture was stirred at 0° C. for 1 h. Water was added and the reaction mixture was warmed to rt for 30 min. The mixture was diluted with CH$_2$Cl$_2$, the organic layer was washed with water and brine, dried over Na$_2$SO$_4$, filtered and concentrated. The crude product was used as such for the next step.

Step 7: tert-butyl (2R,5S)-5-({[tert-butyl(dimethyl)silyl]oxy}methyl)-2-[(E)-2-(2-nitrophenyl)ethenyl]morpholine-4-carboxylate

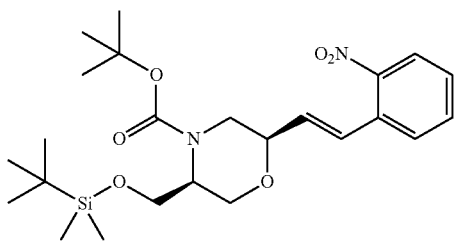 [SMILES: CC(C)(C)OC(=O)N1C[C@@H](/C=C/c2ccccc2[N+](=O)[O-])OC[C@H]1CO[Si](C)(C)C(C)(C)C]

To tert-butyl (2S,5S)-5-({[tert-butyl(dimethyl)silyl]oxy}methyl)-2-formylmorpholine-4-carboxylate (1 eq.) in DME (0.2 M) at rt were added (2-nitrobenzyl)(triphenyl)phosphonium bromide (1.1 eq.), potassium carbonate (2 eq.) and 18-C-6 (0.1 eq.). The reaction mixture was stirred at rt for 12 hrs, filtered on celite and the filtrate was concentrated under reduced pressure. The crude product was purified by automated SiO$_2$ flash chromatography system using solvent gradient of 10% to 60% EtOAc/Hex to afford the desired compound Step 8: tert-butyl (2R,5S)-2-[2-(2-aminophenyl)ethyl]-5-({[tert-butyl(dimethyl)silyl]oxy}methyl)morpholine-4-carboxylate

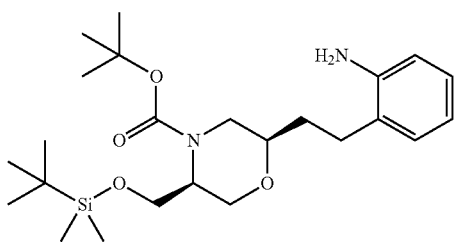 [SMILES: CC(C)(C)OC(=O)N1C[C@@H](CCc2ccccc2N)OC[C@H]1CO[Si](C)(C)C(C)(C)C]

To tert-butyl (2R,5S)-5-({[tert-butyl(dimethyl)silyl]oxy}methyl)-2-[(E)-2-(2-nitrophenyl)ethenyl]morpholine-4-carboxylate (1 eq.) in 2,2,2,-trifluoroethanol (0.4 M) at rt was added 20% Pd(OH)$_2$ (0.2 eq.). The reaction was degassed and then shaken under 1 atm of H$_2$ for 24 hrs. The reaction mixture was filtered on celite and concentrated to afford the desired compound.

Step 9: tert-butyl (2R,5S)-5-({[tert-butyl(dimethyl)silyl]oxy}methyl)-2-[2-(2-{[N-(methoxycarbonyl)-β-phenyl-L-phenylalanyl]amino}phenyl)ethyl]morpholine-4-carboxylate

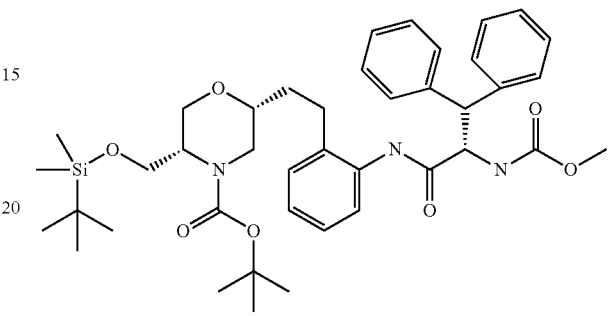

To tert-butyl (2R,5S)-2-[2-(2-aminophenyl)ethyl]-5-({[tert-butyl(dimethyl)silyl]oxy}methyl)morpholine-4-carboxylate (1 eq.) in DMF (0.15 M) at rt was added N-(methoxycarbonyl)-β-phenyl-L-phenylalanine (1.1 eq.), HATU (1.4 eq.) and 2,6-lutidine (3 eq.). The reaction mixture was stirred at rt for 16 h and diluted with EtOAc and saturated aqueous NaHCO$_3$. The aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 10% to 100% EtOAc/Hex to afford the desired compound.

Step 10: tert-butyl (2R,5R)-5-(hydroxymethyl)-2-[2-(2-{[N-(methoxycarbonyl)-β-phenyl-L-phenylalanyl]amino}phenyl)ethyl]morpholine-4-carboxylate

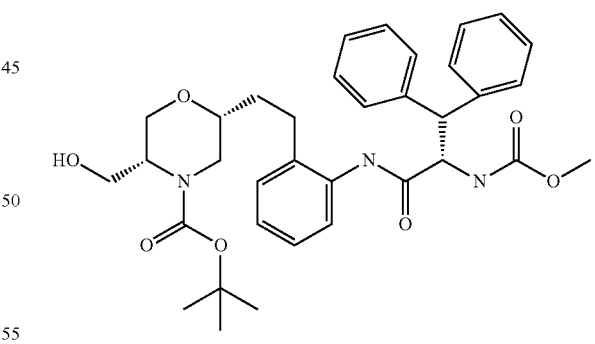

To tert-butyl (2R,5S)-5-({[tert-butyl(dimethyl)silyl]oxy}methyl)-2-[2-(2-{[N-(methoxycarbonyl)-β-phenyl-L-phenylalanyl]amino}phenyl)ethyl]morpholine-4-carboxylate in THF (0.1 M) at rt was added TBAF (1M in THF) (4 eq.). The mixture was stirred at rt for 2 hrs, diluted with EtOAc and saturated aqueous NH$_4$Cl, and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0-5% MeOH/CH$_2$Cl$_2$ to afford the desired compound.

Step 11: (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid

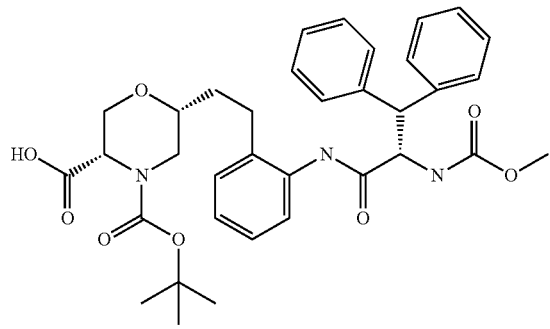 [SMILES: COC(=O)N[C@H](C(=O)Nc1ccccc1CC[C@@H]1CN(C(=O)OC(C)(C)C)[C@H](C(=O)O)CO1)C(c1ccccc1)c1ccccc1]

To tert-butyl (2R,5R)-5-(hydroxymethyl)-2-[2-(2-{[N-(methoxycarbonyl)-β-phenyl-L-phenylalanyl]amino}phenyl)ethyl]morpholine-4-carboxylate (1 eq) in DMF (0.1M) at rt were added PDC (10 eq) and 4 A molecular sieve (1 g/mmol of substrate). The reaction mixture was stirred at rt for 16 hrs. The reaction mixture was then filtered on a celite and the celite pad was washed with EtOAc and water. The filtrate was extracted with EtOAc. The combined organic layers were washed with brine, 1N aqueous HCl and brine, dried over Na$_2$SO$_4$, filtered and concentrated. The crude product was used as such for next step.

Step 12: tert-butyl (2R,5R)-5-(1H-benzimidazol-2-yl)-2-[2-(2-{[N-(methoxycarbonyl)-β-phenyl-L-phenylalanyl]amino}phenyl)ethyl]morpholine-4-carboxylate

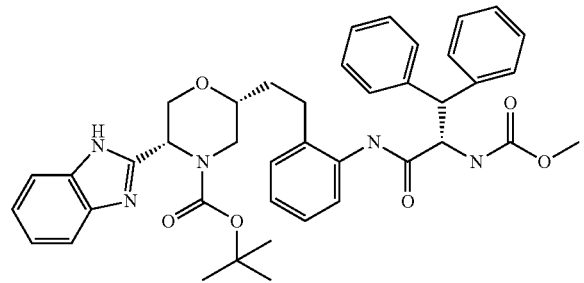 [SMILES: COC(=O)N[C@H](C(=O)Nc1ccccc1CC[C@@H]1CN(C(=O)OC(C)(C)C)[C@H](c2nc3ccccc3[nH]2)CO1)C(c1ccccc1)c1ccccc1]

To (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid (1 eq) in DMF (0.1 M) was added HATU (2 eq) and 2,6-lutidine (3 eq). The reaction mixture was stirred for 5 minutes and benzene-1,2-diamine (1.2 eq) was added. The reaction mixture was stirred at rt for 16 hrs, diluted with EtOAc and saturated aqueous NaHCO$_3$ and the aqueous layer was extracted with EtOAc. The combined organic layers were washed with brine and water, dried over Na$_2$SO$_4$, filtered and concentrated. The residue was diluted in acetic acid (0.3M) and heated at 60° C. for 2 hours and concentrated to dryness under reduced pressure. The crude product was purified by automated SiO$_2$ flash chromatography system using solvent gradient of 10% to 100% EtOAc/Hex to afford the desired compound.

Step 13: N-(2-{2-[(2R,5R)-5-(1H-benzimidazol-2-yl)morpholin-2-yl]ethyl}phenyl)-Nα-(methoxycarbonyl)-β-phenyl-L-phenylalaninamide Tert-butyl (2R,5R)-5-(1H-benzimidazol-2-yl)-2-[2-(2-{[N-(methoxycarbonyl)-β-phenyl-L-phenylalanyl]amino}phenyl)ethyl]morpholine-4-carboxylate in a 1:1 mixture of CH$_2$Cl$_2$/TFA (0.1 M) was stirred at rt for 1 hr. The reaction mixture was concentrated under reduced pressure and the residue was co-evaporated twice with heptane and triturated in Et$_2$O to afford the desired product as a TFA salt. Alternatively, the TFA salt, after concentration, could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH$_2$Cl$_2$ to afford the desired compound. Alternatively, the free base could be purified by filtration on SCX SPE cartridge made of pTSA-SiO$_2$ eluted first with MeOH to remove non basic impurities and eluted then with 10% NH$_4$OH/MeOH to elute the free base and afford the desired compound after concentration under reduced pressure.

M+1, +ESI=604.3

Examples 2 to 30 were prepared by following the same procedures as set forth in Example 1 with the use of the appropriate reagents.

| Ex. | | Compound name | Characteriz, data |
|---|---|---|---|
| 2 | | methyl N-[(1S)-1-benzhydryl-2-[[2-[2-[(2R,5R)-5-(1-methylbenzimidazol-2-yl)morpholin-2-yl]ethyl]phenyl]amino]-2-oxo-ethyl]carbamate | M + 1, + ESI = 618.2 |

-continued

| Ex. | Compound name | Characteriz. data |
|---|---|---|
| 3 | 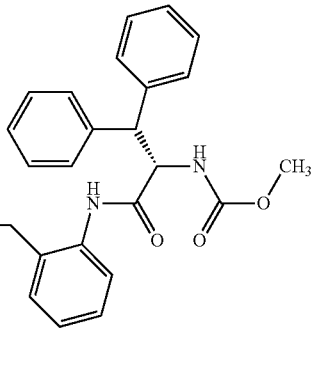 methyl N-[(1S)-1-benzhydryl-2-[[2-[2-[(2R,5R)-5-(7-methyl-1H-benzimidazol-2-yl)morpholin-2-yl]ethyl]phenyl]amino]-2-oxo-ethyl]carbamate | M + 1, + ESI = 618.2 |
| 4 | 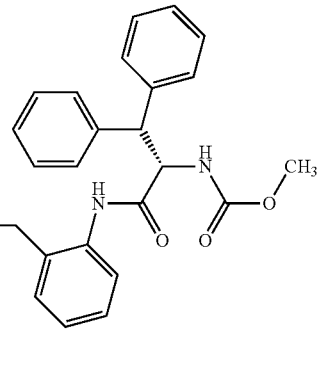 methyl N-[(1S)-1-benzhydryl-2-[[2-[2-[(2R,5R)-5-(6-methyl-1H-benzimidazol-2-yl)morpholin-2-yl]ethyl]phenyl]amino]-2-oxo-ethyl]carbamate | M + 1, + ESI = 618.2 |
| 5 | 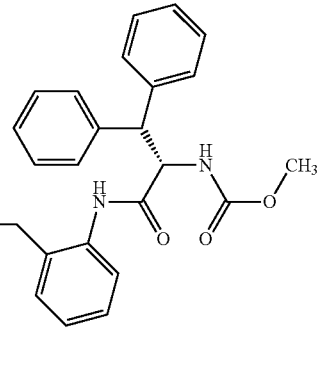 methyl N-[(1S)-1-benzhydryl-2-[[2-[2-[(2R,5R)-5-(3H-imidazo[4,5-c]pyridin-2-yl)morpholin-2-yl]ethyl]phenyl]amino]-2-oxo-ethyl]carbamate | M + 1, + ESI = 605.3 |

-continued

| Ex. | | Compound name | Characteriz. data |
|---|---|---|---|
| 6 | 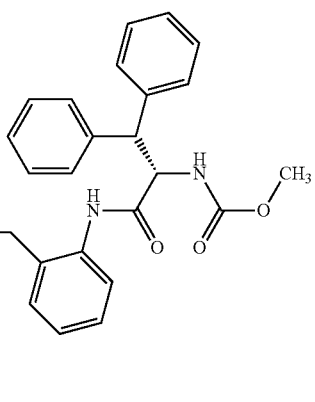 | methyl N-[(1S)-1-benzhydryl-2-[[2-[2-[(2R,5R)-5-(6-methoxy-1H-benzimidazol-2-yl)morpholin-2-yl]ethyl]phenyl]amino]-2-oxo-ethyl]carbamate | M + 1, + ESI = 634.2 |
| 7 | 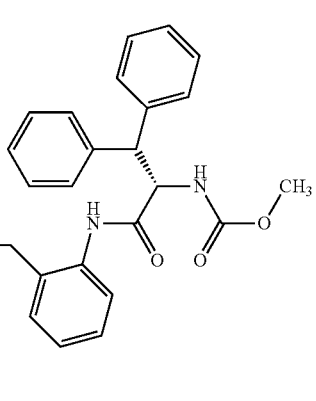 | methyl N-[(1S)-1-benzhydryl-2-[[2-[2-[(2R,5R)-5-(6-methylsulfonyl-1H-benzimidazol-2-yl)morpholin-2-yl]ethyl]phenyl]amino]-2-oxo-ethyl]carbamate | M + 1, + ESI = 682.2 |
| 8 | 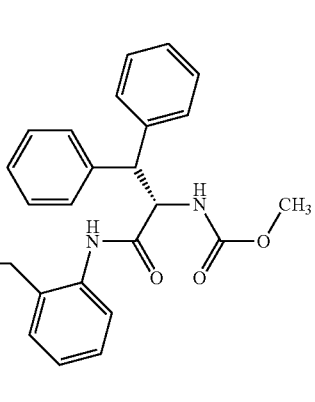 | methyl N-[(1S)-1-benzhydryl-2-oxo-2-[[2-[2-[(2R,5R)-5-[6-(trifluoromethyl)-1H-benzimidazol-2-yl]morpholin-2-yl]ethyl]phenyl]amino]ethyl]carbamate | M + 1, + ESI = 672.1 |
| 9 | 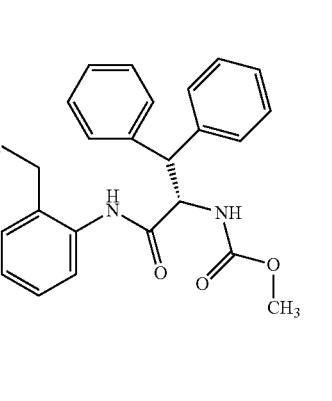 | methyl N-[(1S)-1-benzhydryl-2-[[2-[2-[(2R,5R)-5-(5,6-dimethyl-1H-benzimidazol-2-yl)morpholin-2-yl]ethyl]phenyl]amino]-2-oxo-ethyl]carbamate | M + 1, + ESI = 632.2 |

-continued

| Ex. | | Compound name | Characteriz. data |
|---|---|---|---|
| 10 | 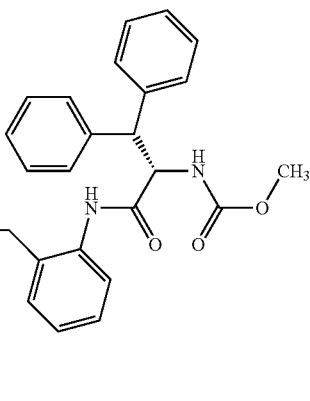 | methyl N-[(1S)-1-benzhydryl-2-[[2-[2-[(2R,5R)-5-(6-cyano-1H-benzimidazol-2-yl)morpholin-2-yl]ethyl]phenyl]amino]-2-oxo-ethyl]carbamate | M + 1, + ESI = 629.0 |
| 11 | 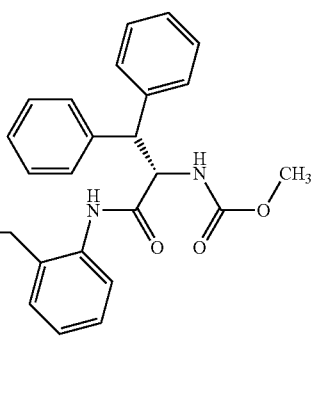 | methyl N-[(1S)-1-benzhydryl-2-[[2-[2-[(2R,5R)-5-(6-bromo-1H-benzimidazol-2-yl)morpholin-2-yl]ethyl]phenyl]amino]-2-oxo-ethyl]carbamate | M + 1, + ESI = 682.2 |
| 12 | 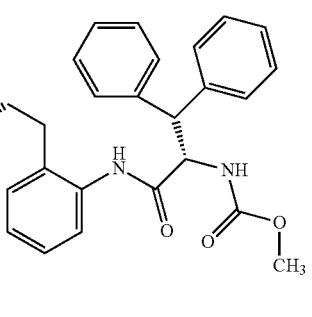 | methyl N-[(1S)-1-benzhydryl-2-[[2-[2-[(2R,5R)-5-(5,6-dichloro-1H-benzimidazol-2-yl)morpholin-2-yl]ethyl]phenyl]amino]-2-oxo-ethyl]carbamate | M + 1, + ESI = 672.1 |
| 13 | 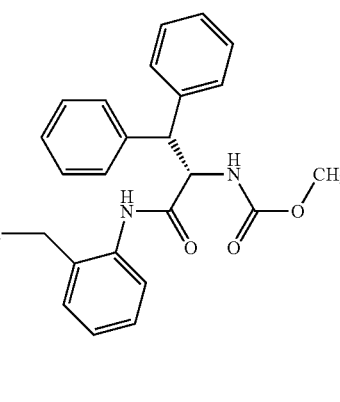 | methyl N-[(1S)-1-benzhydryl-2-[[2-[2-[(2R,5R)-5-(7-chloro-1H-benzimidazol-2-yl)morpholin-2-yl]ethyl]phenyl]amino]-2-oxo-ethyl]carbamate | M + 1, + ESI = 638.2 |

-continued

| Ex. | | Compound name | Characteriz, data |
|---|---|---|---|
| 14 | 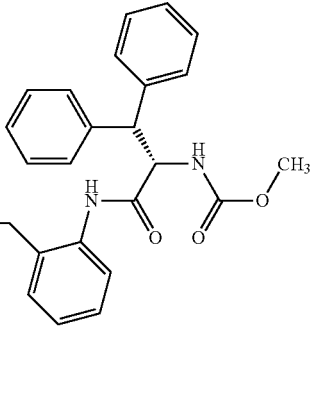 | methyl N-[(1S)-1-benzhydryl-2-[[2-[2-[(2R,5R)-5-(7-bromo-1H-benzimidazol-2-yl)morpholin-2-yl]ethyl]phenyl]amino]-2-oxo-ethyl]carbamate | M + 1, + ESI = 682.2 |
| 15 | 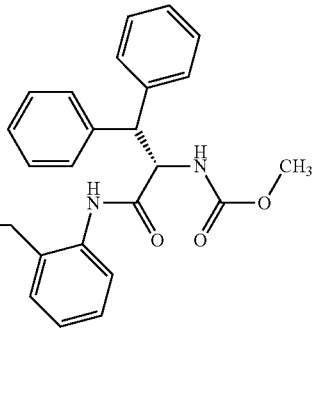 | methyl N-[(1S)-1-benzhydryl-2-[[2-[2-[(2R,5R)-5-(4-hydroxy-1H-benzimidazol-2-yl)morpholin-2-yl]ethyl]phenyl]amino]-2-oxo-ethyl]carbamate | M + 1, + ESI = 620.3 |
| 16 | 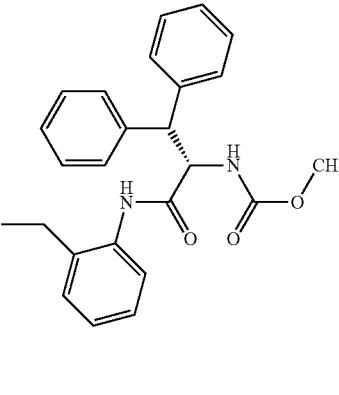 | methyl N-[(1S)-1-benzhydryl-2-[[2-[2-[(2R,5R)-5-(5,6-difluoro-1H-benzimidazol-2-yl)morpholin-2-yl]ethyl]phenyl]amino]-2-oxo-ethyl]carbamate | M + 1, + ESI = 640.3 |

-continued

| Ex. | | Compound name | Characteriz. data |
|---|---|---|---|
| 17 | 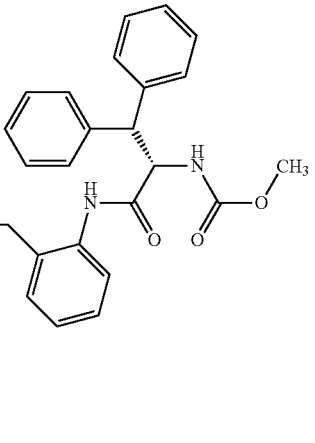 | methyl N-[(1S)-1-benzhydryl-2-oxo-2-[[2-[2-[(2R,5R)-5-(4,5,6-trifluoro-1H-benzimidazol-2-yl)morpholin-2-yl]ethyl]phenyl]amino]ethyl]carbamate | M + 1, + ESI = 658.3 |
| 18 | 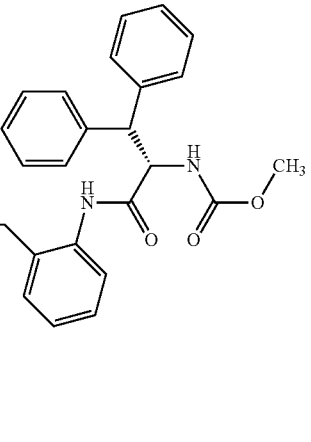 | methyl N-[(1S)-1-benzhydryl-2-[[2-[2-[(2R,5R)-5-(6-fluoro-1H-benzimidazol-2-yl)morpholin-2-yl]ethyl]phenyl]amino]-2-oxo-ethyl]carbamate | M + 1, + ESI = 622.3 |
| 19 | 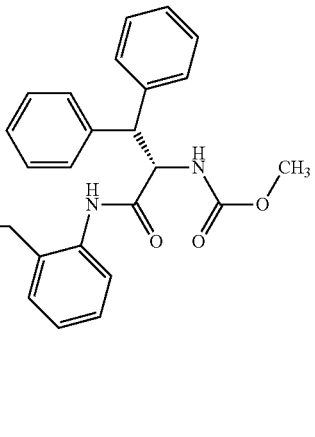 | methyl N-[(1S)-1-benzhydryl-2-[[2-[2-[(2R,5R)-5-(4-bromo-6-methyl-1H-benzimidazol-2-yl)morpholin-2-yl]ethyl]phenyl]amino]-2-oxo-ethyl]carbamate | M + 1, + ESI = 696.2 |

-continued

| Ex. | | Compound name | Characteriz. data |
|---|---|---|---|
| 20 | 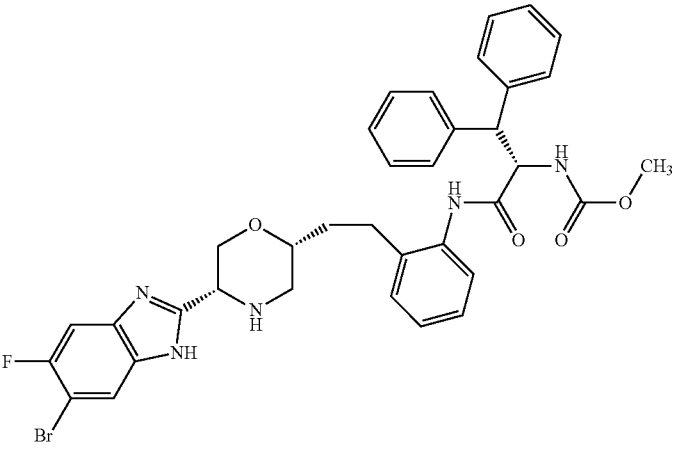 [SMILES: COC(=O)N[C@H](C(=O)Nc1ccccc1CC[C@@H]1CN[C@H](c2nc3cc(F)c(Br)cc3[nH]2)CO1)C(c1ccccc1)c1ccccc1] | methyl N-[(1S)-1-benzhydryl-2-[[2-[2-[(2R,5R)-5-(6-bromo-5-fluoro-1H-benzimidazol-2-yl)morpholin-4-ium-2-yl]ethyl]phenyl]amino]-2-oxo-ethyl]carbamate | M + 1, + ESI = 700.2 |
| 21 | 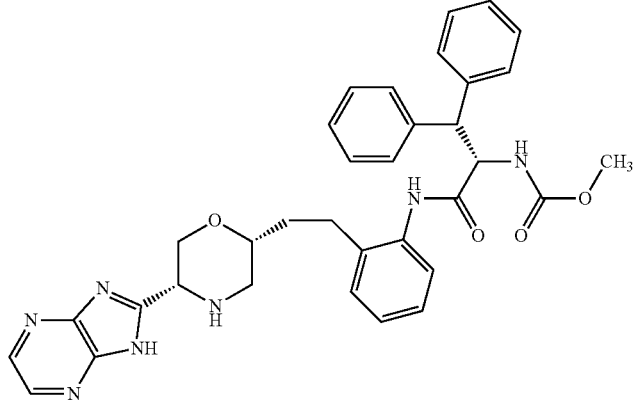 [SMILES: COC(=O)N[C@H](C(=O)Nc1ccccc1CC[C@@H]1CN[C@H](c2nc3nccnc3[nH]2)CO1)C(c1ccccc1)c1ccccc1] | methyl N-[(1S)-1-benzhydryl-2-[[2-[2-[(2R,5R)-5-(3H-imidazo[4,5-b]pyrazin-2-yl)morpholin-2-yl]ethyl]phenyl]amino]-2-oxo-ethyl]carbamate | M + 1, + ESI = 606.3 |
| 22 | 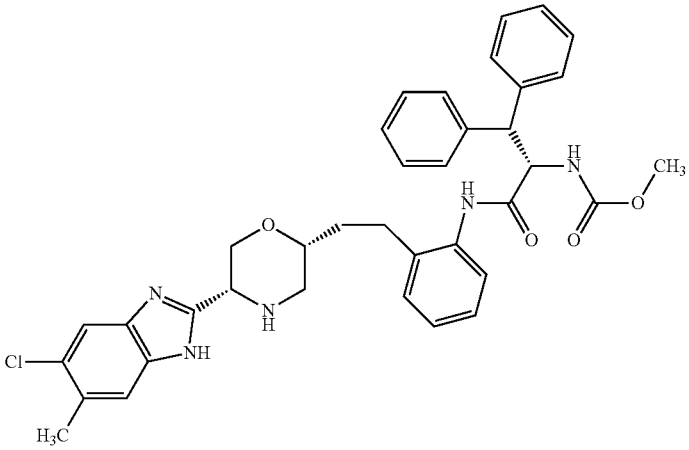 | methyl N-[(1S)-1-benzhydryl-2-[[2-[2-[(2R,5R)-5-(5-chloro-6-methyl-1H-benzimidazol-2-yl)morpholin-2-yl]ethyl]phenyl]amino]-2-oxo-ethyl]carbamate | M + 1, + ESI = 657.3 |

-continued

| Ex. | | Compound name | Characteriz. data |
|---|---|---|---|
| 23 | 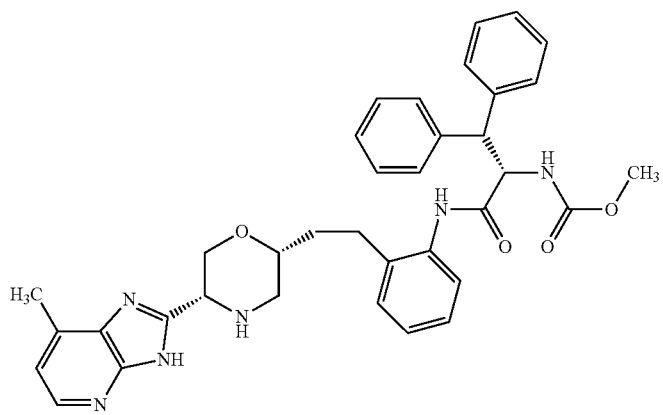 [SMILES: COC(=O)N[C@H](C(=O)Nc1ccccc1CC[C@@H]1CN[C@H](c2nc3c(C)ccnc3[nH]2)CO1)C(c1ccccc1)c1ccccc1] | methyl N-[(1S)-1-benzhydryl-2-[[2-[2-[(2R,5R)-5-(7-methyl-3H-imidazo[4,5-b]pyridin-2-yl)morpholin-2-yl]ethyl]phenyl]amino]-2-oxo-ethyl]carbamate | M + 1, + ESI = 619.3 |
| 24 | 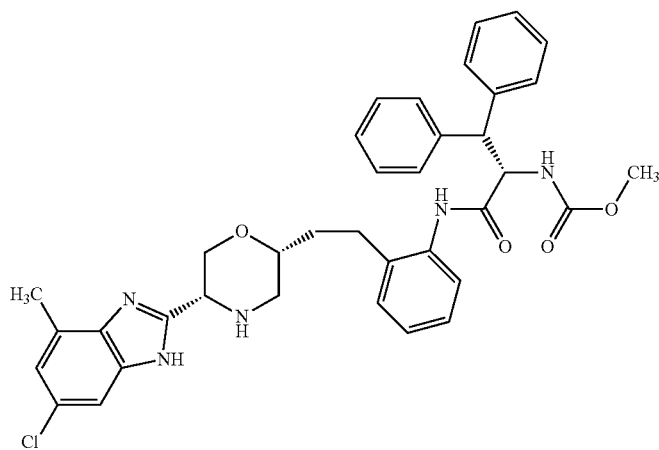 [SMILES: COC(=O)N[C@H](C(=O)Nc1ccccc1CC[C@@H]1CN[C@H](c2nc3c(C)cc(Cl)cc3[nH]2)CO1)C(c1ccccc1)c1ccccc1] | methyl N-[(1S)-1-benzhydryl-2-[[2-[2-[(2R,5R)-5-(6-chloro-4-methyl-1H-benzimidazol-2-yl)morpholin-2-yl]ethyl]phenyl]amino]-2-oxo-ethyl]carbamate | M + 1, + ESI = 652.3 |
| 25 | 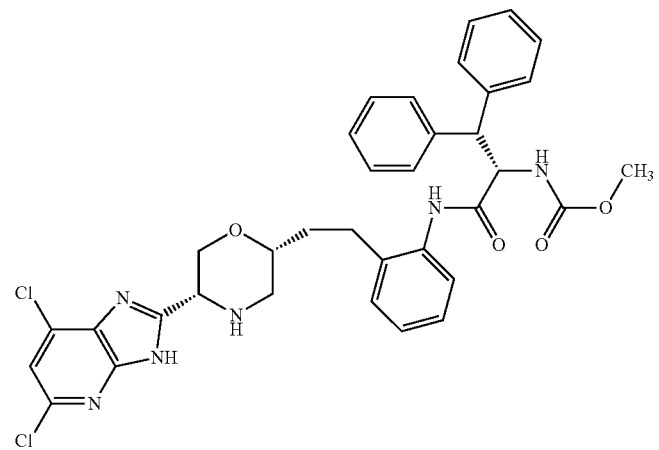 [SMILES: COC(=O)N[C@H](C(=O)Nc1ccccc1CC[C@@H]1CN[C@H](c2nc3c(Cl)cc(Cl)nc3[nH]2)CO1)C(c1ccccc1)c1ccccc1] | methyl N-[(1S)-1-benzhydryl-2-[[2-[2-[(2R,5R)-5-(4,6-dichloro-1H-benzimidazol-2-yl)morpholin-2-yl]ethyl]phenyl]amino]-2-oxo-ethyl]carbamate | M + 1, + ESI = 672.2 |

-continued

| Ex. | | Compound name | Characteriz. data |
|---|---|---|---|
| 26 | 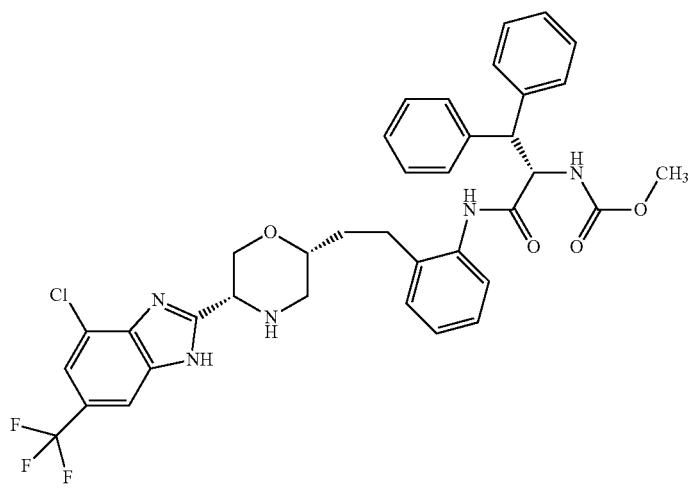 [SMILES: COC(=O)N[C@H](C(=O)Nc1ccccc1CC[C@@H]1CN[C@H](c2nc3c(Cl)cc(C(F)(F)F)cc3[nH]2)CO1)C(c1ccccc1)c1ccccc1] | methyl N-[(1S)-1-benzhydryl-2-[[2-[2-[(2R,5R)-5-[4-chloro-6-(trifluoromethyl)-1H-benzimidazol-2-yl]morpholin-2-yl]ethyl]phenyl]amino]-2-oxo-ethyl]carbamate | M + 1, + ESI = 706.2 |
| 27 | 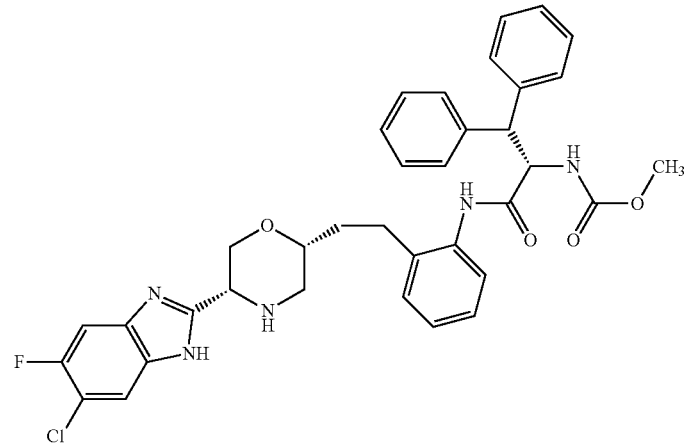 [SMILES: COC(=O)N[C@H](C(=O)Nc1ccccc1CC[C@@H]1CN[C@H](c2nc3cc(F)c(Cl)cc3[nH]2)CO1)C(c1ccccc1)c1ccccc1] | N-(2-{2-[(2R,5R)-5-(6-chloro-5-fluoro-1H-benzimidazol-2-yl)morpholin-2-yl]ethyl}phenyl)-Nα-(methoxycarbonyl)-b-phenyl-L-phenylalaninamide | M + 1, + ESI = 655.9 |
| 28 | 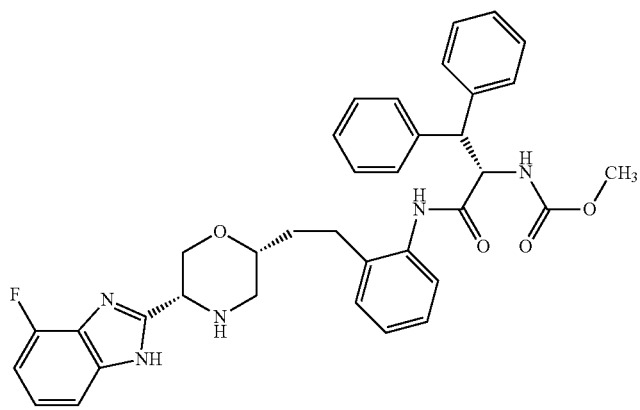 [SMILES: COC(=O)N[C@H](C(=O)Nc1ccccc1CC[C@@H]1CN[C@H](c2nc3c(F)cccc3[nH]2)CO1)C(c1ccccc1)c1ccccc1] | N-(2-{2-[(2R,5R)-5-(4-fluoro-1H-benzimidazol-2-yl)morpholin-2-yl]ethyl}phenyl)-Nα-(methoxycarbonyl)-b-phenyl-L-phenylalaninamide | M + 1, + ESI = 621.8 |

| Ex. | | Compound name | Characteriz. data |
|---|---|---|---|
| 29 | 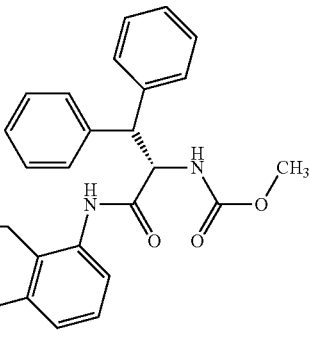 | N-(2-{2-[(2R,5R)-5-(5,6-dimethyl-1H-benzimidazol-2-yl)morpholin-2-yl]ethyl}-3-fluorophenyl)-Nα-(methoxycarbonyl)-b-phenyl-L-phenylalaninamide | M + 1, + ESI = 650.0 |

Example 30 methyl N-[(1S)-1-benzhydryl-2-[[4-[2-[(2R,5R)-5-(5,6-dimethyl-1H-benzimidazol-2-yl)morpholin-2-yl]ethyl]-3-pyridyl]amino]-2-oxo-ethyl]carbamate

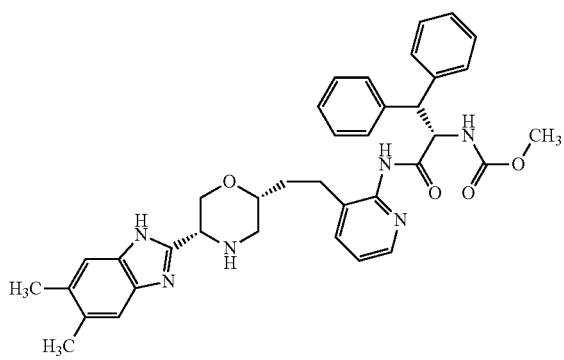

Step 1: tert-butyl (2R,5S)-5-({[tert-butyl(dimethyl)silyl]oxy}methyl)-2-ethynylmorpholine-4-carboxylate To a stirred solution of dimethyl (1-diazo-2-oxopropyl) phosphonate (2.1 eq) in THF (0.1 M) at −78° C. was added 4N sodium methoxide in MeOH (2.3 eq) over 10 minutes. The reaction mixture was stirred at −78° C. for 15 min. A solution of tert-butyl (2S,5S)-5-({[tert-butyl(dimethyl)silyl]oxy}methyl)-2-formylmorpholine-4-carboxylate (1 eq) in THF (0.3M) was slowly added over 20 minutes. The reaction mixture was stirred at −78° C. for 1.5 hours and then allowed to stand at rt overnight prior to be concentrated under reduced pressure. The residue was diluted with aqueous sodium hydrogen carbonate and EtOAc and the aqueous layer was extracted EtOAc. The combined organic layers were washed with brine, dried with MgSO₄ and concentrated under vacuum. The crude product was purified by automated SiO₂ flash chromatography system using solvent gradient of 0% to 60% EtOAc/Hex to afford the desired compound.

Step 2: tert-butyl (2R,5R)-2-ethynyl-5-(hydroxymethyl)morpholine-4-carboxylate

To tert-butyl (2R,5S)-5-({[tert-butyl(dimethyl)silyl]oxy}methyl)-2-ethynylmorpholine-4-carboxylate in THF (0.1 M) at rt was added TBAF (1M in THF) (4 eq.). The mixture was stirred at rt for 2 hrs, diluted with EtOAc and saturated aqueous NH₄Cl and the aqueous layer was extracted with EtOAc. The combined organic layers were washed with brine, dried over Na₂SO₄, filtered and concentrated. The crude product was purified by automated SiO₂ flash chromatography system using solvent gradient of 0-5% MeOH/CH₂Cl₂ to afford the desired compound.

Step 3: (3S,6R)-4-(tert-butoxycarbonyl)-6-ethynyl-morpholine-3-carboxylic acid

To tert-butyl (2R,5R)-2-ethynyl-5-(hydroxymethyl)morpholine-4-carboxylate (1 eq) in DMF (0.1M) at rt were added PDC (10 eq) and 4 A molecular sieve (1 g/mmol of substrate). The reaction mixture was stirred at rt for 16 hrs. The reaction mixture was then filtered on a celite and the celite pad was washed with EtOAc and water. The filtrate was extracted with EtOAc. The combined organic layers were washed with brine, IN aqueous HCl and brine, dried over Na₂SO₄, filtered and concentrated. The crude product was used as such for next step.

Step 4: tert-butyl (2R,5R)-5-(5,6-dimethyl-1H-benzimidazol-2-yl)-2-ethynylmorpholine-4-carboxylate To (3S,6R)-4-(tert-butoxycarbonyl)-6-ethynylmorpholine-3-carboxylic acid (1 eq) in DMF (0.1 M) was added HATU (2 eq) and 2,6-lutidine (3 eq). The reaction mixture was stirred for 5 minutes and 4,5-dimethylbenzene-1,2-diamine (1.2 eq) was added. The reaction mixture was stirred at rt for 16 hrs, diluted with EtOAc and saturated aqueous NaHCO₃ and the aqueous layer was extracted with EtOAc. The combined organic layers were washed with brine and water, dried over Na$_2$SO$_4$, filtered and concentrated. The residue was diluted in acetic acid (0.3M) and heated at 60° C. for 2 hours and concentrated to dryness under reduced pressure. The crude product was purified by automated SiO$_2$ flash chromatography system using solvent gradient of 10% to 100% EtOAc/Hex to afford the desired compound.

Step 5: tert-butyl (2R,5R)-2-[(2-aminopyridin-3-yl)ethynyl]-5-(5,6-dimethyl-1H-benzimidazol-2-yl)morpholine-4-carboxylate A solution of tert-butyl (2R,5R)-5-(5,6-dimethyl-1H-benzimidazol-2-yl)-2-ethynylmorpholine-4-carboxylate (1 eq) and 3-bromopyridin-2-amine (1.4 eq) in acetonitrile (0.1M) and triethylamine (25 eq) was flushed with nitrogen for 10 minutes. Then bis(triphenylphosphine)palladium(ii) chloride (0.1 eq) and copper(i) iodide (1.2 eq) were added and the mixture was flushed again with nitrogen for 10 minutes. The reaction mixture was stirred at 60° C. for 2 hours in the dark. It was concentrated to dryness and the residue was purified by automated SiO$_2$ flash chromatography system using solvent gradient of 0% to 10% MeOH/CH$_2$Cl2 to afford the desired compound.

Step 6: tert-butyl (2R,5R)-2-[2-(2-aminopyridin-3-yl)ethyl]-5-(5,6-dimethyl-1H-benzimidazol-2-yl)morpholine-4-carboxylate To tert-butyl (2R,5R)-2-[(2-aminopyridin-3-yl)ethynyl]-5-(5,6-dimethyl-1H-benzimidazol-2-yl)morpholine-4-carboxylate (1 eq.) in 2,2,2,-trifluoroethanol (0.4 M) at rt was added 10% Pd/C (0.2 eq.). The reaction was degassed and then shaken under 1 atm of H$_2$ for 24 hrs. The reaction mixture was filtered on celite and concentrated to afford the desired compound.

Step 7: tert-butyl (2R,5R)-5-(5,6-dimethyl-1H-benzimidazol-2-yl)-2-[2-(2-{[N-(methoxycarbonyl)-β-phenyl-L-phenylalanyl]amino}pyridin-3-yl)ethyl]morpholine-4-carboxylate To N-(methoxycarbonyl)-β-phenyl-L-phenylalanine (1.1 eq.) in DMF (0.15 M) at rt were added HATU (1.4 eq.) and 2,6-lutidine (3 eq.). The reaction mixture was stirred for 30 min and tert-butyl (2R,5R)-2-[2-(2-aminopyridin-3-yl)ethyl]-5-(5,6-dimethyl-1H-benzimidazol-2-yl)morpholine-4-carboxylate (1 eq) was added. The reaction mixture was stirred at 60° C. for 16 h and diluted with EtOAc and saturated aqueous NaHCO$_3$. The aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0% to 10% MeOH/CH$_2$Cl$_2$ to afford the desired compound. Alternatively, DMF could be replaced as solvent by pyridine to ease coupling involving less reactive amine.

Step 8: methyl N-[(1S)-1-benzhydryl-2-[[4-[2-[(2R,5R)-5-(5,6-dimethyl-1H-benzimidazol-2-yl)morpholin-2-yl]ethyl]-3-pyridyl]amino]-2-oxo-ethyl]carbamate Tert-butyl (2R,5R)-5-(5,6-dimethyl-1H-benzimidazol-2-yl)-2-[2-(2-{[N-(methoxycarbonyl)-β-phenyl-L-phenylalanyl]amino}pyridin-3-yl)ethyl]morpholine-4-carboxylate in a 1:1 mixture of CH$_2$Cl$_2$/TFA (0.1 M) was stirred at rt for 1 hr. The reaction mixture was concentrated under reduced pressure and the residue was co-evaporated twice with heptane and triturated in Et$_2$O to afford the desired product as a TFA salt. Alternatively, the TFA salt, after concentration, could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH$_2$Cl$_2$ to afford the desired compound. Alternatively, the free base could be purified by filtration on SCX SPE cartridge made of pTSA-SiO$_2$ eluted first with MeOH to remove non basic impurities and eluted then with 10% NH$_4$OH/MeOH to elute the free base and afford the desired compound after concentration under reduced pressure.

M+1, +ESI=633.3

The following examples (31 to 33) were synthesized from (3S,6R)-4-(tert-butoxycarbonyl)-6-ethynylmorpholine-3-carboxylic acid according to the procedures described in steps 4 to 8 from Example 30 and by using the appropriate reagents.

| Example | | Compound name | Characterization data |
|---|---|---|---|
| 31 | 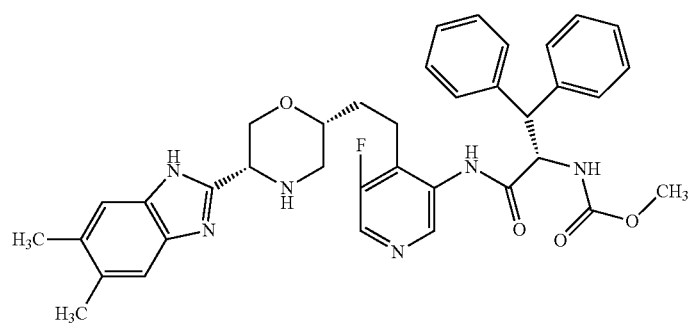 | methyl N-[(1S)-1-benzhydryl-2-[[4-[2-[(2R,5R)-5-(5,6-dimethyl-1H-benzimidazol-2-yl)morpholin-2-yl]ethyl]-5-fluoro-3-pyridyl]amino]-2-oxo-ethyl]carbamate | M + 1, + ESI = 651.2 |

-continued

| Example | | Compound name | Characterization data |
|---|---|---|---|
| 32 | 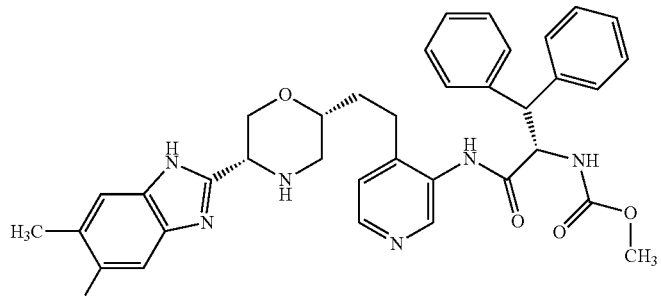 | methyl N-[(1S)-1-benzhydryl-2-[[4-[2-[(2R,5R)-5-(5,6-dimethyl-1H-benzimidazol-2-yl)morpholin-2-yl]ethyl]-3-pyridyl]amino]-2-oxo-ethyl]carbamate | M + 1, + ESI = 633.3 |
| 33 | 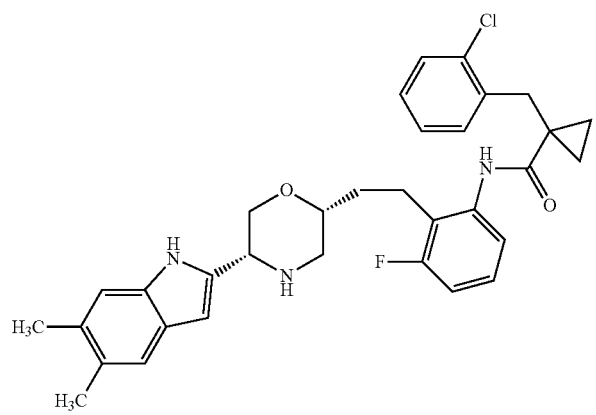 [SMILES: Cc1cc2cc([C@@H]3CO[C@H](CCc4c(F)cccc4NC(=O)C4(Cc5ccccc5Cl)CC4)CN3)[nH]c2cc1C] | 1-[(2-chlorophenyl)methyl]-N-[4-[2-[(2R,5R)-5-(5,6-dimethyl-1H-benzimidazol-2-yl)morpholin-2-yl]ethyl]-5-fluoro-3-pyridyl]cyclopropanecarboxamide | M + 1, + ESI = 562.2 |

Example 34

N-(4-{2-[(2R,5R)-5-(5,6-dimethyl-1H-benzimidazol-2-yl)morpholin-2-yl]ethyl}-2-oxo-1,2-dihydropyridin-3-yl)-β-phenyl-L-phenylalaninamide

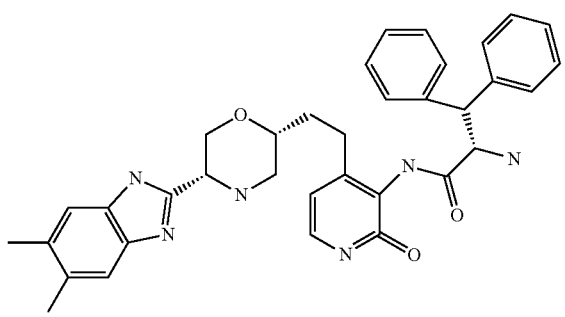

Step 1: tert-butyl (2R,5R)-5-(5,6-dimethyl-1H-benzimidazol-2-yl)-2-[2-(2-methoxy-3-{[N-(methoxycarbonyl)-β-phenyl-L-phenylalanyl]amino}pyridin-4-yl)ethyl]morpholine-4-carboxylate Tert-butyl (2R,5R)-5-(5,6-dimethyl-1H-benzimidazol-2-yl)-2-[2-(2-methoxy-3-{[N-(methoxycarbonyl)-β-phenyl-L-phenylalanyl]amino}pyridin-4-yl)ethyl]morpholine-4-carboxylate was prepared from tert-butyl (2R,5R)-5-(5,6-dimethyl-1H-benzimidazol-2-yl)-2-ethynylmorpholine-4-carboxylate according to the procedures described in steps 5 to 7 of Example 30 and using the appropriate reagents.

Step 2: N-(4-{2-[(2R,5R)-5-(5,6-dimethyl-1H-benzimidazol-2-yl)morpholin-2-yl]ethyl}-2-oxo-1,2-dihydropyridin-3-yl)-β-phenyl-L-phenylalaninamide To a solution of sodium iodide (7 eq.) in acetonitrile (0.03M) was added TMS-Cl (7 eq.). The reaction mixture was stirred for 15 minutes and then tert-butyl (2R,5R)-5-(5,6-dimethyl-1H-benzimidazol-2-yl)-2-[2-(2-methoxy-3-{[N-(methoxycarbonyl)-β-phenyl-L-phenylalanyl]amino}pyridin-4-yl)ethyl]morpholine-4-carboxylate (1 eq.) was added as a solution in acetonitrile (0.03M). The mixture was stirred at 60° C. for 60 minutes and then concentrated to dryness. The residue was purified by automated SiO₂ flash chromatography system using solvent gradient of 0% to 10% MeOH/CH₂Cl₂ containing 1% of NEt₃ to afford the desired compound.

M+1, +ESI=591.1

Example 35 methyl N-[(1S)-1-benzhydryl-2-[[4-[2-[(2R,5R)-5-(5,6-dimethyl-1H-benzimidazol-2-yl)morpholin-2-yl]ethyl]-2-oxo-1H-pyridin-3-yl]amino]-2-oxo-ethyl]carbamate

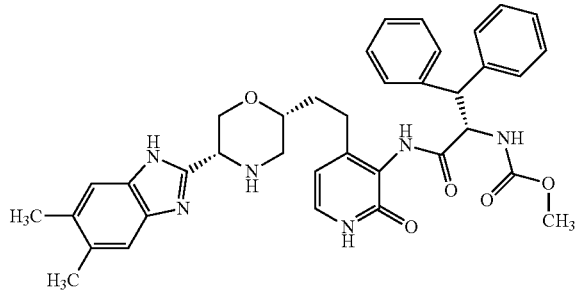

Step 1: methyl N-[(1S)-1-benzhydryl-2-[[4-[2-[(2R,5R)-5-(5,6-dimethyl-1H-benzimidazol-2-yl)morpholin-2-yl]ethyl]-2-oxo-1H-pyridin-3-yl]amino]-2-oxo-ethyl]carbamate To a solution of sodium iodide (7 eq.) in acetonitrile (0.03M) was added TMS-Cl (7 eq.). The reaction mixture was stirred for 15 minutes and then tert-butyl (2R,5R)-5-(5,6-dimethyl-1H-benzimidazol-2-yl)-2-[2-(2-methoxy-3-{[N-(methoxycarbonyl)-β-phenyl-L-phenylalanyl]amino}pyridin-4-yl)ethyl]morpholine-4-carboxylate (1 eq.) was added as a solution in acetonitrile (0.03M). The mixture was stirred at rt for 60 minutes and then concentrated to dryness. The residue was purified by automated SiO$_2$ flash chromatography system using solvent gradient of 0% to 10% MeOH/CH$_2$Cl$_2$ containing 1% of NEt$_3$ to afford the desired compound.
M+1, +ESI=649.3

Example 36

Nα-(methoxycarbonyl)-N-[2-(2-{(2R,5R)-5-[(5-methyl-4H-1,2,4-triazol-3-yl)]morpholin-2-yl}ethyl)phenyl]-β-phenyl-L-phenylalaninamide

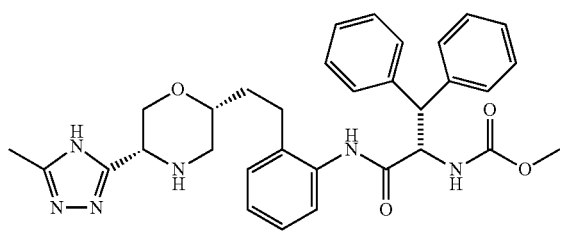

Step 1: tert-butyl (2R,5S)-5-(hydrazinylcarbonyl)-2-[2-(2-{[N-β(methoxycarbonyl)-β-phenyl-L-phenylalanyl]amino}phenyl)ethyl]morpholine-4-carboxylate To a solution of (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid (1 eq.) in methanol at rt was added diazomethane until gas evolution ceased. Solvent was evaporated and the residue dissolved in ethanol (0.2M) and hydrazine (2.5 eq.) was added. The reaction mixture was stirred at reflux for 16 hrs. Hydrazine was added (5 eq.) again and the reaction mixture was further stirred at reflux for 5 hours. The reaction mixture was concentrated to dryness and the residue was purified by automated silica gel flash chromatography system eluted with a gradient 80% to 100% of EtOAc/Hex to afford the desired compound.

Step 2: tert-butyl (2R,5R)-2-[2-(2-{[N-(methoxycarbonyl)-β-phenyl-L-phenylalanyl]amino}phenyl)ethyl]-5-[(5-methyl-4H-1,2,4-triazol-3-yl)]morpholine-4-carboxylate To a solution of tert-butyl (2R,5S)-5-(hydrazinylcarbonyl)-2-[2-(2-{[N-(methoxycarbonyl)-β-phenyl-L-phenylalanyl]amino}phenyl)ethyl]morpholine-4-carboxylate (1 eq.) in EtOH (0.5M) was added a solution of ethyl ethanimidoate (1 eq.) in MTBE. The reaction mixture was stirred at 55° C. for 4 hours. The reaction mixture was then evaporated and ethanol was added (0.125M). The mixture was then heated to 80° C. for 48 hrs. Reaction was then concentrated to dryness and the on silica gel and the residue was purified by automated silica gel flash chromatography system eluted with a gradient 70% to 100% of EtOAc/Hex to afford the desired compound.

Step 3: Nα-(methoxycarbonyl)-N-[2-(2-{(2R,5R)-5-[(5-methyl-4H-1,2,4-triazol-3-yl)]morpholin-2-yl}ethyl)phenyl]-β-phenyl-L-phenylalaninamide Nα-(methoxycarbonyl)-N-[2-(2-{(2R,5R)-5-[(5-methyl-4H-1,2,4-triazol-3-yl)]morpholin-2-yl}ethyl)phenyl]-β-phenyl-L-phenylalaninamide was prepared from tert-butyl (2R,5R)-2-[2-(2-{[N-(methoxycarbonyl)-β-phenyl-L-phenylalanyl]amino}phenyl)ethyl]-5-[(5-methyl-4H-1,2,4-triazol-3-yl)]morpholine-4-carboxylate by following procedure described in step 8 of Example 30.
M+1, +ESI=569.2

Example 37 methyl [(1S)-2-[(2-{2-[(2R,5R)-5-cyanomorpholin-2-yl]ethyl}phenyl)amino]-1-(diphenylmethyl)-2-oxoethyl]carbamate

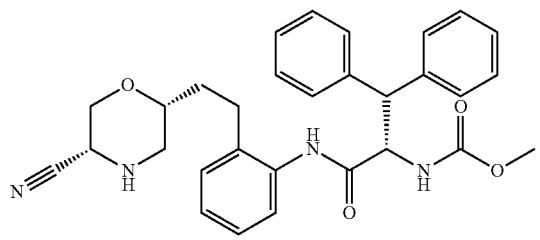 [SMILES: COC(=O)N[C@H](C(=O)Nc1ccccc1CC[C@@H]1CN[C@H](C#N)CO1)C(c1ccccc1)c1ccccc1]

Step 1: tert-butyl (2R,5R)-5-cyano-2-[2-(2-{[N-(methoxycarbonyl)-β-phenyl-L-phenylalanyl]amino}phenyl)ethyl]morpholine-4-carboxylate To a cold (−10° C.) solution of tert-butyl (2R,5S)-5-carbamoyl-2-[2-(2-{[N-(methoxycarbonyl)-β-phenyl-L-phenylalanyl]amino}phenyl)ethyl]morpholine-4-carboxylate (1 eq) in THF (0.1 M) was added trifluoroacetic anhydride (2 eq) and pyridine (4 eq). The reaction mixture was stirred for 1 h and diluted with EtOAc. The organic layer was washed with saturated aqueous NaHCO$_3$, dried over Na$_2$SO$_4$, filtered and concentrated. The residue was purified by automated silica gel flash chromatography system eluted with a gradient 0% to 60% of EtOAc/Hex to afford the desired compound.

Step 2: methyl [(1S)-2-[(2-{2-[(2R,5R)-5-cyano-morpholin-2-yl]ethyl}phenyl)amino]-1-(diphenylmethyl)-2-oxoethyl]carbamate Methyl [(1S)-2-[(2-{2-[(2R,5R)-5-cyanomorpholin-2-yl]ethyl}phenyl)amino]-1-(diphenylmethyl)-2-oxoethyl]carbamate was prepared from tert-butyl (2R,5R)-5-cyano-2-[2-(2-{[N-(methoxycarbonyl)-β-phenyl-L-phenylalanyl]amino}phenyl)ethyl]morpholine-4-carboxylate by following procedures described in step 13 of Example 1.
M+1, +ESI=486.4

Example 38

Nα-(methoxycarbonyl)-β-phenyl-N-(2-{2-[(2R,5R)-5-(1H-tetrazol-5-yl)morpholin-2-yl]ethyl}phenyl)-L-phenylalaninamide

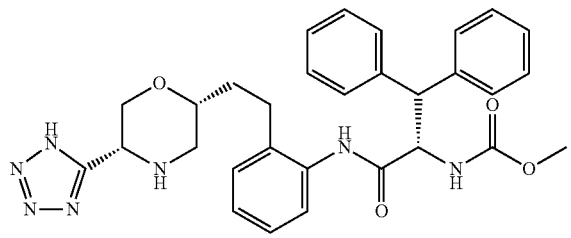 [SMILES: COC(=O)N[C@H](C(=O)Nc1ccccc1CC[C@@H]1CN[C@H](c2nnn[nH]2)CO1)C(c1ccccc1)c1ccccc1]

Step 1: Nα-(methoxycarbonyl)-β-phenyl-N-(2-{2-[(2R,5R)-5-(1H-tetrazol-5-yl)morpholin-2-yl]ethyl}phenyl)-L-phenylalaninamide To a stirred solution of tert-butyl (2R,5R)-5-cyano-2-[2-(2-{[N-(methoxycarbonyl)-β-phenyl-L-phenylalanyl]amino}phenyl)ethyl]morpholine-4-carboxylate (1 eq) in toluene (0.1 M) at rt was added azidotributyltin (10 eq). The reaction was heated at reflux for 16 h, cooled to rt and concentrated. The residue was purified by automated silica gel flash chromatography system eluted with a gradient 0% to 10% of MeOH/CH$_2$Cl$_2$ to afford tert-butyl (2R,5R)-2-[2-(2-{[N-(methoxycarbonyl)-β-phenyl-L-phenylalanyl]amino}phenyl)ethyl]-5-(1H-tetrazol-5-yl)morpholine-4-carboxylate which was then treated with TFA following the procedure described in step 13 of Example 1 to afford the desired compound.
M+1, +ESI=556.2

Examples 39 and 40 methyl [(1S)-2-[(2-{2-[(2R,5R)-5-(1-benzyl-1H-tetrazol-5-yl)morpholin-2-yl]ethyl}phenyl)amino]-1-(diphenylmethyl)-2-oxoethyl]carbamate and methyl [(1S)-2-[(2-{2-[(2R,5R)-5-(2-benzyl-2H-tetrazol-5-yl)morpholin-2-yl]ethyl}phenyl)amino]-1-(diphenylmethyl)-2-oxoethyl]carbamate

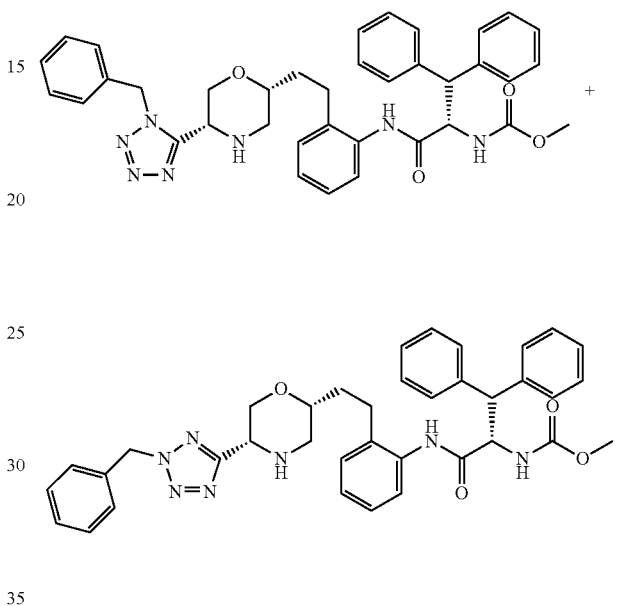

Step 1: Nα-(methoxycarbonyl)-β-phenyl-N-(2-{2-[(2R,5R)-5-(1H-tetrazol-5-yl)morpholin-2-yl]ethyl}phenyl)-L-phenylalaninamide To a solution of tert-butyl (2R,5R)-2-[2-(2-{[N-(methoxycarbonyl)-β-phenyl-L-phenylalanyl]amino}phenyl)ethyl]-5-(1H-tetrazol-5-yl)morpholine-4-carboxylate (1 eq) in DMF (0.1M) were added potassium carbonate (2 eq), potassium iodide (0.2 eq) and benzyl bromide (2 eq). The reaction mixture was stirred at rt for 2 h, diluted with EtOAc and the organic layer was washed successively with sat aqueous NH$_4$Cl and brine, dried over Na$_2$SO$_4$, filtered and concentrated. The residue was purified by automated silica gel flash chromatography system eluted with a gradient 0% to 60% of EtOAc/Hex to afford a mixture of tert-butyl (2R,5R)-5-(1-benzyl-1H-tetrazol-5-yl)-2-[2-(2-{[N-(methoxycarbonyl)-β-phenyl-L-phenylalanyl]amino}phenyl)ethyl]morpholine-4-carboxylate and tert-butyl (2R,5R)-5-(2-benzyl-2H-tetrazol-5-yl)-2-[2-(2-{[N-(methoxycarbonyl)-β-phenyl-L-phenylalanyl]amino}phenyl)ethyl]morpholine-4-carboxylate which were then treated with TFA following the procedure described in step 13 of Example 1 to afford the desired compounds.

M+1, +ESI=646.2 for both compounds

Example 41 methyl {(1S)-1-(diphenylmethyl)-2-[(2-{2-[(2R,5R)-5-(1,2,4-oxadiazol-3-yl)morpholin-2-yl]ethyl}phenyl)amino]-2-oxoethyl}carbamate

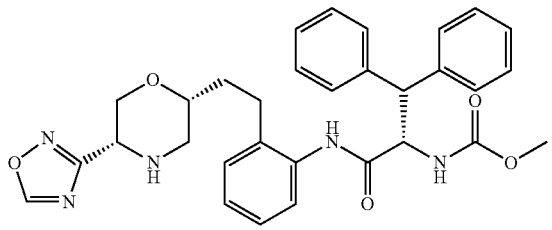 [SMILES: COC(=O)N[C@H](C(=O)Nc1ccccc1CC[C@@H]1CN[C@H](c2ncon2)CO1)C(c1ccccc1)c1ccccc1]

Step 1: tert-butyl (2R,5R)-5-[N'-(formyloxy)carbamimidoyl]-2-[2-(2-{[N-(methoxycarbonyl)-β-phenyl-L-phenylalanyl]amino}phenyl)ethyl]morpholine-4-carboxylate To a solution of from tert-butyl (2R,5R)-5-cyano-2-[2-(2-{[N-(methoxycarbonyl)-β-phenyl-L-phenylalanyl]amino}phenyl)ethyl]morpholine-4-carboxylate (1 eq) in absolute ethanol (0.1 M) was added hydroxylamine hydrochloride (1.5 eq) and triethylamine (2.2 eq). The reaction was heated at 70° C. for 4 h, allowed to cool to rt and concentrated. Water (0.4 ml) was added, and the resulting white precipitate was filtered and rinsed with water. The solid was collected and azeotropically dried with toluene. To a solution of formic acid (1 eq) in dichloromethane (0.1 M) was added PyBOP (1.1 eq) and diisopropylethylamine (2 eq). The reaction mixture was stirred for 5 min, and a solution of the crude N-hydroxyimidamide in dichloromethane (0.1 M) was added. The reaction was stirred at rt for 16 h, diluted with dichloromethane, and the organic layer was washed successively with saturated aqueous NH$_4$Cl and brine, dried over Na$_2$SO$_4$, filtered and concentrated. The residue was purified by automated silica gel flash chromatography system eluted with a gradient 0% to 100% of EtOAc/Hex to afford the desired product.

Step 2: methyl {(1S)-1-(diphenylmethyl)-2-[(2-{2-[(2R,5R)-5-(1,2,4-oxadiazol-3-yl)morpholin-2-yl]ethyl}phenyl)amino]-2-oxoethyl}carbamate A solution of tert-butyl (2R,5R)-5-[N'-(formyloxy)carbamimidoyl]-2-[2-(2-{[N-(methoxycarbonyl)-β-phenyl-L-phenylalanyl]amino}phenyl)ethyl]morpholine-4-carboxylate (1 eq) in DMF (0.1 M) was heated at 110° C. for 48 h, cooled to rt, diluted with EtOAc and the organic layer was successively washed with saturated aqueous NH$_4$Cl and brine, dried over Na$_2$SO$_4$, filtered and concentrated. The residue was purified by automated silica gel flash chromatography system eluted with a gradient 0% to 50% of EtOAc/Hex to afford tert-butyl (2R,5R)-2-[2-(2-{[N-(methoxycarbonyl)-β-phenyl-L-phenylalanyl]amino}phenyl)ethyl]-5-(1,2,4-oxadiazol-3-yl)morpholine-4-carboxylate which was then treated with TFA following the procedure described in step 13 of Example 1 to afford the desired compounds.

M+1, +ESI=556.5

Example 42 methyl {(1S)-1-(diphenylmethyl)-2-[(2-{2-[(2R,5R)-5-(1H-imidazol-2-yl)morpholin-2-yl]ethyl}phenyl)amino]-2-oxoethyl}carbamate

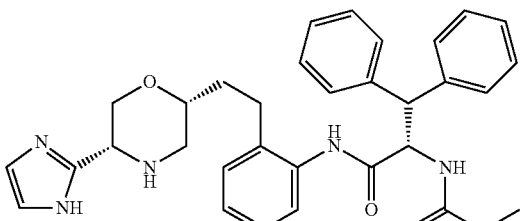

Step 1: methyl {(1S)-1-(diphenylmethyl)-2-[(2-{2-[(2R,5R)-5-(1H-imidazol-2-yl)morpholin-2-yl]ethyl}phenyl)amino]-2-oxoethyl}carbamate To a solution of tert-butyl (2R,5S)-5-formyl-2-[2-(2-{[N-(methoxycarbonyl)-β-phenyl-L-phenylalanyl]amino}phenyl)ethyl]morpholine-4-carboxylate (1 eq) were added a solution of ammonia in MeOH (10 eq)) and glyoxal trimer dihydrate (1 eq). The reaction was heated at 55° C. for 6 h and concentrated. The residue was purified by automated silica gel flash chromatography system eluted with a gradient 0% to 100% of EtOAc/Hex to afford tert-butyl (2R,5R)-5-(1H-imidazol-2-yl)-2-[2-(2-{[N-(methoxycarbonyl)-β-phenyl-L-phenylalanyl]amino}phenyl)ethyl]morpholine-4-carboxylate which was then treated with TFA following the procedure described in step 13 of Example 1 to afford the desired compounds.

M+1, +ESI=554.2

Example 43 methyl {(1S)-1-(diphenylmethyl)-2-[(2-{2-[(2R,5R)-5-(5-methyl-1H-imidazol-2-yl)morpholin-2-yl]ethyl}phenyl)amino]-2-oxoethyl}carbamate

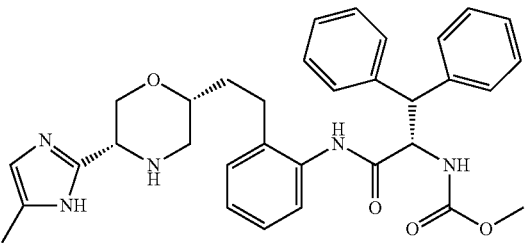

Step 1: methyl {(1S)-1-(diphenylmethyl)-2-[(2-{2-[(2R,5R)-5-(5-methyl-1H-imidazol-2-yl)morpholin-2-yl]ethyl}phenyl)amino]-2-oxoethyl}carbamate Methyl {(1S)-1-(diphenylmethyl)-2-[(2-{2-[(2R,5R)-5-(5-methyl-1H-imidazol-2-yl)morpholin-2-yl]ethyl}phenyl)amino]-2-oxoethyl}carbamate was prepared from tert-butyl (2R,5S)-5-formyl-2-[2-(2-{[N-(methoxycarbonyl)-β-phenyl-L-phenylalanyl]amino}phenyl)ethyl]morpholine-4-carboxylate by following the procedure described in Example 42 and using the appropriate reagents.

M+1, +ESI=568.3

Example 44

N-(2-{2-[(2R,5R)-5-(5-benzyl-1H-imidazol-2-yl)morpholin-2-yl]ethyl}phenyl)-Nα-(methoxycarbonyl)-β-phenyl-L-phenylalaninamide

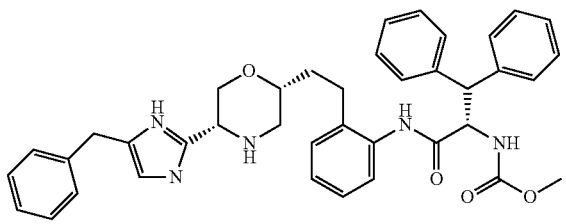

Step 1: tert-butyl (2R,5S)-5-{[(2S)-1-hydroxy-3-phenylpropan-2-yl]carbamoyl}-2-[2-(2-{[N-(methoxycarbonyl)-β-phenyl-L-phenylalanyl]amino}phenyl)ethyl]morpholine-4-carboxylate EDCI (1.3 eq) and HOBT (1.3 eq) were added to a stirred solution of (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid (1 eq) and 2,6-LUTIDINE (3 eq) in DMF (0.1M). After stirring for 5 min, L-phenylalanilol (1.15 eq) was added. The reaction was stirred at rt for 3 h, diluted with EtOAc, the organic layer was washed successively with saturated aqueous NH$_4$Cl and brine, dried over Na$_2$SO$_4$, filtered and concentrated. The residue was purified by automated silica gel flash chromatography system eluted with a gradient 0% to 100% of EtOAc/Hex.

Step 2: N-(2-{2-[(2R,5R)-5-(5-benzyl-1H-imidazol-2-yl)morpholin-2-yl]ethyl}phenyl)-Nα-(methoxycarbonyl)-β-phenyl-L-phenylalaninamide Oxalyl chloride (5 eq) was added dropwise to a solution of DMSO (10 eq) in dichloromethane (0.1 M) cooled −78° C. The mixture was stirred at −78° C. for 15 min. Tert-butyl (2R,5S)-5-{[(2S)-1-hydroxy-3-phenylpropan-2-yl]carbamoyl}-2-[2-(2-{[N-(methoxycarbonyl)-β-phenyl-L-phenylalanyl]amino}phenyl)ethyl]morpholine-4-carboxylate (1 eq) in dichloromethane (0.4M) was added dropwise and the mixture was stirred for 1 hr before adding triethylamine (10 eq). The reaction mixture warmed to 0° C. for 30 min, and then diluted with dichloromethane and water. The layers were separated, and the organic layer was successively washed with water and brine, dried over Na$_2$SO$_4$, filtered and concentrated. The crude aldehyde was diluted in acetic acid (0.2 M) and ammonium acetate (20 eq) was added. The reaction mixture was heated in a sealed vial at 100° C. for 1 h. The reaction mixture was cooled to rt, coevaporated with toluene, diluted with dichloromethane and the organic layer was successively washed with saturated aqueous NaHCO$_3$ and brine, passed through a phase separator from IST Biotage and concentrated. The residue was purified by automated silica gel flash chromatography system eluted with a gradient 0% to 100% of EtOAc/Hex to afford tert-butyl (2R,5R)-5-(5-benzyl-1H-imidazol-2-yl)-2-[2-(2-{[N-(methoxycarbonyl)-β-phenyl-L-phenylalanyl]amino}phenyl)ethyl]morpholine-4-carboxylate which was then treated with TFA following the procedure described in step 13 of Example 1 to afford the desired compound.

M+1, +ESI=644.2

Example 45

Nα-(methoxycarbonyl)-β-phenyl-N-(2-{2-[(2R,5R)-5-(5-phenyl-1H-imidazol-2-yl)morpholin-2-yl]ethyl}phenyl)-L-phenylalaninamide

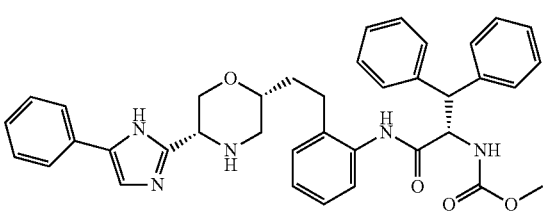 [SMILES: COC(=O)N[C@H](C(=O)Nc1ccccc1CC[C@@H]1CN[C@H](c2ncc(-c3ccccc3)[nH]2)CO1)C(c1ccccc1)c1ccccc1]

Step 1: Nα-(methoxycarbonyl)-β-phenyl-N-(2-{2-[(2R,5R)-5-(5-phenyl-1H-imidazol-2-yl)morpholin-2-yl]ethyl}phenyl)-L-phenylalaninamide Nα-(methoxycarbonyl)-β-phenyl-N-(2-{2-[(2R,5R)-5-(5-phenyl-1H-imidazol-2-yl)morpholin-2-yl]ethyl}phenyl)-L-phenylalaninamide was prepared (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid by following the procedure described in Example 44 and using the appropriate reagents.

M+1, +ESI=630.3

Example 46

Nα-(methoxycarbonyl)-β-phenyl-N-(2-{2-[(2R,5R)-5-(2-phenyl-1H-imidazol-5-yl)morpholin-2-yl]ethyl}phenyl)-L-phenylalaninamide

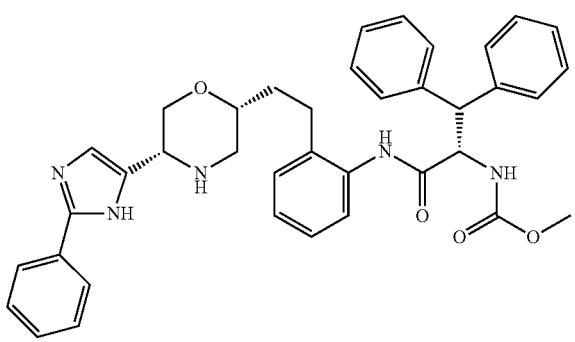 [SMILES: COC(=O)N[C@H](C(=O)Nc1ccccc1CC[C@@H]1CN[C@H](c2cnc(-c3ccccc3)[nH]2)CO1)C(c1ccccc1)c1ccccc1]

Step 1: Nα-(methoxycarbonyl)-β-phenyl-N-(2-{2-[(2R,5R)-5-(2-phenyl-1H-imidazol-5-yl)morpholin-2-yl]ethyl}phenyl)-L-phenylalaninamide To a solution of tert-butyl (2R,5S)-5-(bromoacetyl)-2-[2-(2-{[N-(methoxycarbonyl)-β-phenyl-L-phenylalanyl]amino}phenyl)ethyl]morpholine-4-carboxylate (1 eq, obtained from (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid through standard literature procedures) in DMF (0.1 M) was added potassium carbonate (2 eq) and benzamidine (1.3 eq). The reaction mixture was stirred at rt for 3 h, diluted with EtOAc and the organic layer was washed successively with water and brine, dried over Na2SO₄, filtered and concentrated. The residue was purified by automated silica gel flash chromatography system eluted with a gradient 0% to 10% of MeOH/CH₂Cl₂ to afford tert-butyl (2R,5R)-2-[2-(2-{[N-(methoxycarbonyl)-β-phenyl-L-phenylalanyl]amino}phenyl)ethyl]-5-(2-phenyl-1H-imidazol-5-yl)morpholine-4-carboxylate which was then treated with TFA following the procedure described in step 13 of Example 1 to afford the desired compound.

M+1, +ESI=630.3

Example 47

Nα-(methoxycarbonyl)-N-(2-{2-[(2R,5R)-5-(2-methyl-1H-imidazol-5-yl)morpholin-2-yl]ethyl}phenyl)-β-phenyl-L-phenylalaninamide

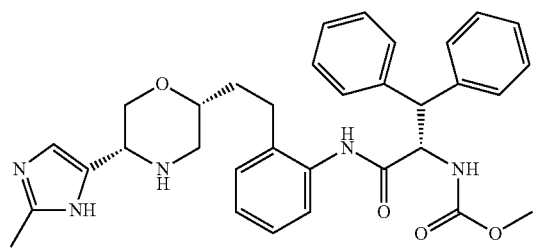

Step 1: Nα-(methoxycarbonyl)-N-(2-{2-[(2R,5R)-5-(2-methyl-1H-imidazol-5-yl)morpholin-2-yl]ethyl}phenyl)-β-phenyl-L-phenylalaninamide Nα-(methoxycarbonyl)-N-(2-{2-[(2R,5R)-5-(2-methyl-1H-imidazol-5-yl)morpholin-2-yl]ethyl}phenyl)-β-phenyl-L-phenylalaninamide was prepared tert-butyl (2R,5S)-5-(bromoacetyl)-2-[2-(2-{[N-(methoxycarbonyl)-β-phenyl-L-phenylalanyl]amino}phenyl)ethyl]morpholine-4-carboxylate by following the procedure described in Example 46 and using the appropriate reagents.

M+1, +ESI=568.3

Example 48

N-(2-{2-[(2R,5R)-5-(4,5-dimethyl-1H-imidazol-2-yl)morpholin-2-yl]ethyl}phenyl)-Nα-(methoxycarbonyl)-β-phenyl-L-phenylalaninamide

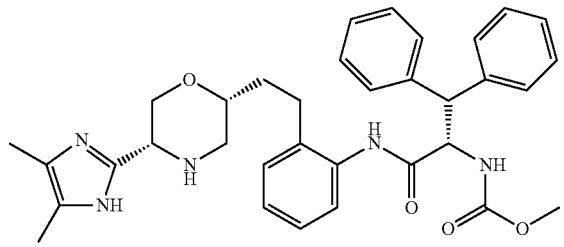

Step 1: N-(2-{2-[(2R,5R)-5-(4,5-dimethyl-1H-imidazol-2-yl)morpholin-2-yl]ethyl}phenyl)-Nα-(methoxycarbonyl)-β-phenyl-L-phenylalaninamide A solution of tert-butyl (2R,5S)-5-formyl-2-[2-(2-{[N-(methoxycarbonyl)-β-phenyl-L-phenylalanyl]amino}phenyl)ethyl]morpholine-4-carboxylate and 2,3-butadione (1.4 eq) in acetic acid (0.2M) was heated at 100° C. for 3 h, cooled to rt and coevaporated three times with toluene. The residue was dissolved in EtOAc, the organic layer was washed successively with saturated aqueous NaHCO₃ and brine, dried over Na₂SO₄, filtered and concentrated. The residue was purified by automated silica gel flash chromatography system eluted with a gradient 0% to 70% of EtOAc/Hex to afford tert-butyl (2R,5R)-5-(4,5-dimethyl-1H-imidazol-2-yl)-2-[2-(2-{[N-(methoxycarbonyl)-β-phenyl-L-phenylalanyl]amino}phenyl)ethyl]morpholine-4-carboxylate which was then treated with TFA following the procedure described in step 13 of Example 1 to afford the desired compound.

M+1, +ESI=582.3

Example 49

N-(2-{2-[(2R,5R)-5-ethynylmorpholin-2-yl]ethyl}phenyl)-Nα-(methoxycarbonyl)-β-phenyl-L-phenylalaninamide

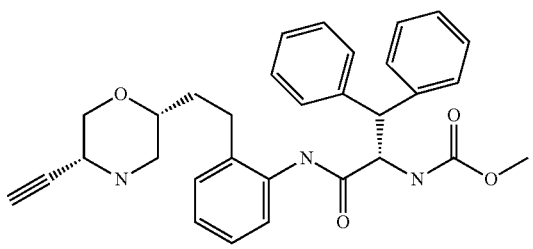 [SMILES: C#C[C@@H]1CO[C@H](CCc2ccccc2NC(=O)[C@@H](NC(=O)OC)C(c2ccccc2)c2ccccc2)CN1]

Step 1. tert-butyl (2R,5S)-2-[2-(2-aminophenyl)ethyl]-5-({[tert-butyl(dimethyl)silyl]oxy}methyl)morpholine-4-carboxylate Nitrogen gas was bubbled through a solution of tert-butyl (2R,5S)-5-({[tert-butyl(dimethyl)silyl]oxy}methyl)-2-[2-(2-nitrophenyl)ethenyl]morpholine-4-carboxylate (1.0 equiv) in methanol (0.2M) for five minutes. Palladium hydroxide 20% Wt (0.2 equiv) was added and the reaction mixture was stirred under a 1 atm. of hydrogen gas for 24 hours. Upon completion the mixture was filter through Celite™ and rinsed with methanol and dichloromethane. The filtrate was concentrated in vacuo. The crude product was used directly in the next step.

Step 2. tert-butyl (2R,5S)-2-(2-{2-[(tert-butoxycarbonyl)amino]phenyl}ethyl)-5-({[tert-butyl(dimethyl)silyl]oxy}methyl)morpholine-4-carboxylate The crude tert-butyl (2R,5S)-2-[2-(2-aminophenyl)ethyl]-5-({[tert-butyl(dimethyl)silyl]oxy}methyl)morpholine-4-carboxylate was dissolved in a 1:1 mixture of tetrahydrofuran and water (0.2M) and sodium bicarbonate (3.0 equiv) was added, followed by di-tert-butyl dicarbonate (1.0 equiv). The resulting mixture was stirred at room temperature for 48 hours. The reaction mixture was diluted with ethyl acetate and a saturated aqueous sodium bicarbonate solution. The aqueous layer was extracted with ethyl acetate three times. The organics were combined and dried over sodium sulfate. The solid was filtered off and the filtrate was concentrated in vacuo. The residue obtained was purified using an automated flash chromatography with a solvent gradient of 0% to 100% ethyl acetate and hexanes.

Step 3. tert-butyl (2R,5R)-2-(2-{2-[(tert-butoxycarbonyl)amino]phenyl}ethyl)-5-(hydroxymethyl)morpholine-4-carboxylate To a solution of tert-butyl (2R,5S)-2-(2-{2-[(tert-butoxycarbonyl)amino]phenyl}ethyl)-5-({[tert-butyl(dimethyl)silyl]oxy}methyl)morpholine-4-carboxylate (1.0 equiv) in tetrahydrofuran (0.3M) was added tetrabutyl ammonium fluoride (3.0 equiv). The reaction was stirred 2 hours and upon completion, a saturated aqueous solution of ammonium chloride was added. The aqueous phase was extracted three times with ethyl acetate. The organic layers were combined, washed with brine, dried over sodium sulfate. The solid was filtered off and the filtrate was concentrated in vacuo. The residue was purified by automated silica-gel flash chromatography using a solvent gradient of 0% to 100% ethyl acetate and hexanes.

Step 4. tert-butyl (2R,5S)-2-(2-{2-[(tert-butoxycarbonyl)amino]phenyl}ethyl)-5-formylmorpholine-4-carboxylate To a stirred solution of tert-butyl (2R,5R)-2-(2-{2-[(tert-butoxycarbonyl)amino]phenyl}ethyl)-5-(hydroxymethyl)morpholine-4-carboxylate (1.0 equiv) in dichloromethane (0.2M) at room temperature was added Dess-Martin periodinane (1.5 equiv) in one portion. After 1 hour, the reaction was completed and the mixture was cooled to 0° C. A 1M aqueous solution of sodium thiosulfate was added along with a saturated aqueous solution of sodium bicarbonate, the resulting mixture was stirred for 10 minutes. The phases were separated and the aqueous layer was extracted with dichloromethane. The organics were combined and dried over sodium sulfate. The solid was filtered off and the filtrate was concentrated in vacuo. The crude product was used without further purification in the next step.

Step 5. tert-butyl (2R,5R)-2-(2-{2-[(tert-butoxycarbonyl)amino]phenyl}ethyl)-5-ethynylmorpholine-4-carboxylate To a solution of tert-butyl (2R,5S)-2-(2-{2-[(tert-butoxycarbonyl)amino]phenyl}ethyl)-5-formylmorpholine-4-carboxylate (1.0 equiv) and dimethyl (1-diazo-2-oxopropyl)phosphonate (2.6 equiv) in anhydrous methanol (0.1M) at 0° C. was added potassium carbonate (3.5 equiv). The resulting mixture was stirred at room temperature for 30 minutes. Upon completion, the reaction mixture was diluted with diethyl ether and a saturated aqueous solution of sodium bicarbonate was added. The layers were separated and the aqueous layer was extracted three times with diethyl ether. The organics were combined and dried over sodium sulfate. The solid was filtered off and the filtrate was concentrated in vacuo. The residue was purified by automated silica-gel flash chromatography using a solvent gradient of 0% to 50% ethyl acetate and hexanes.

Step 6. 2-{2-[(2R,5R)-5-ethynylmorpholin-2-yl]ethyl}aniline

Tert-Butyl (2R,5R)-2-(2-{2-[(tert-butoxycarbonyl)amino]phenyl}ethyl)-5-ethynylmorpholine-4-carboxylate (1.0 equiv) was diluted in dichloromethane (1.0M). The resulting mixture was then treated with trifluoroacetic acid (16 equiv). The resulting mixture was stirred at room temperature for 2 hours, at which point the volatiles were removed in vacuo. The residual trifluoroacetic acid was removed with three successive co-evaporations with heptane. The trifluoroacetic acid salt obtained was dissolved in dichloromethane and neutralized using a saturated aqueous solution of sodium bicarbonate. The aqueous layer was extracted with dichloromethane and the organic layers were combined, dried over sodium sulfate, filtered and concentrated in vacuo. The crude product was used as it is in the next step.

Step 7. tert-butyl (2R,5R)-2-[2-(2-aminophenyl)ethyl]-5-ethynylmorpholine-4-carboxylate To 2-{2-[(2R,5R)-5-ethynylmorpholin-2-yl]ethyl}aniline (1.0 equiv) in solution in a 1:1 mixture of tetrahydrofuran and water (0.2 M) was added sodium bicarbonate (2.0 equiv) followed by di-tert-butyl dicarbonate (1.0 equiv) The resulting mixture was stirred at room temperature for 1 hour. The reaction mixture was diluted with ethyl acetate and a saturated aqueous sodium bicarbonate solution. The aqueous layer was extracted with ethyl acetate three times. The organics were combined and dried over sodium sulfate. The solid was filtered off and the filtrate was concentrated in vacuo. The residue obtained was purified using an automated flash chromatography with a solvent gradient of 0% to 100% ethyl acetate and hexanes.

Step 8. tert-butyl (2R,5R)-5-ethynyl-2-[2-(2-{N-(methoxycarbonyl)-β-phenyl-L-phenylalanyl]amino}phenyl)ethyl]morpholine-4-carboxylate N-(Methoxycarbonyl)-β-phenyl-L-phenylalanine (1.2 equiv), HATU (1.4 equiv) and 2,6-lutidine (2.8 equiv) were combined in N,N-dimethylformamide (0.1M) at room temperature, and stirred for 5 minutes. tert-Butyl (2R,5R)-2-[2-(2-aminophenyl)ethyl]-5-ethynylmorpholine-4-carboxylate (1.0 equiv) was then added and the reaction mixture was stirred at this temperature 72 hours. Upon reaction completion, the reaction was diluted with ethyl acetate and a saturated aqueous solution of sodium bicarbonate was added. The layers were separated and the aqueous layer was extracted three times with ethyl acetate. The organics were combined, washed with brine and dried over sodium sulfate. The solid was filtered off and the filtrate was concentrated in vacuo. Co-evaporation with heptane three times was used to remove any remaining traces of N,N-dimethylformamide. The crude product was purified using automated silica-gel flash chromatography using a solvent gradient of 0% to 100% of ethyl acetate and hexanes.

Step 9. N-(2-{2-[(2R,5R)-5-ethynylmorpholin-4-ium-2-yl]ethyl}phenyl)-Nα-(methoxycarbonyl)-β-phenyl-L-phenylalaninamide trifluoroacetate Tert-Butyl (2R,5R)-5-ethynyl-2-[2-(2-{N-(methoxycarbonyl)-β-phenyl-L-phenylalanyl]amino}phenyl)ethyl]morpholine-4-carboxylate (1.0 equiv) was diluted in dichloromethane (0.1M) and treated with trifluoroacetic acid (160 equiv). The resulting mixture was stirred at room temperature for 15 min, at which point the volatiles were removed in vacuo. The residual trifluoroacetic acid was removed with three successive co-evaporations with heptane. The trifluoroacetic acid salt obtained was triturated with diethyl ether to afford the pure desired compound.

M+1 (+ESI)=512.2

Example 50

N-(2-{2-[(2R,5R)-5-(1-benzyl-1H-1,2,3-triazol-4-yl)morpholin-2-yl]ethyl}phenyl)-Nα-(methoxycarbonyl)-β-phenyl-L-phenylalaninamide

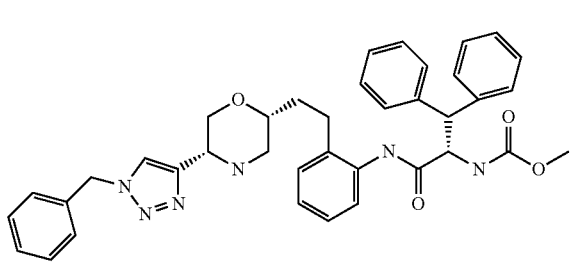 [SMILES: COC(=O)N[C@H](C(=O)Nc1ccccc1CC[C@@H]1CN[C@H](c2cn(Cc3ccccc3)nn2)CO1)C(c1ccccc1)c1ccccc1]

Step 1. tert-butyl (2R,5R)-5-(1-benzyl-1H-1,2,3-triazol-4-yl)-2-[2-(2-{[N-(methoxycarbonyl)-β-phenyl-L-phenylalanyl]amino}phenyl)ethyl]morpholine-4-carboxylate To a solution of tert-butyl (2R,5R)-5-ethynyl-2-[2-(2-{[N-(methoxycarbonyl)-β-phenyl-L-phenylalanyl]amino}phenyl)ethyl]morpholine-4-carboxylate (1.0 equiv) in tetrahydrofuran (0.1M) was added copper(I) iodide (1.5 equiv), Hünig's base (5.0 equiv) and benzyl azide (1.0 equiv). The resulting mixture was stirred in a sealed tube at 66° C. for 12 hours. Upon completion, the reaction mixture was concentrated in vacuo and the residue was directly purified using an automated silica-gel flash chromatography with a solvent gradient of 0% to 20% of methanol and dichloromethane using RediSep Rf Gold™ Columns Step 2. N-(2-{2-[(2R,5R)-5-(1-benzyl-1H-1,2,3-triazol-4-yl)morpholin-2-yl]ethyl}phenyl)-Nα-(methoxycarbonyl)-β-phenyl-L-phenylalaninamide Tert-Butyl (2R,5R)-5-(1-benzyl-1H-1,2,3-triazol-4-yl)-2-[2-(2-{[N-(methoxycarbonyl)-β-phenyl-L-phenylalanyl]amino}phenyl)ethyl]morpholine-4-carboxylate (1.0 equiv) was dissolved in dichloromethane (0.1M) and trifluoroacetic acid (150 equiv) was added. The reaction mixture was stirred at room temperature for 15 minutes. Upon completion, the volatiles were evaporated under reduced pressure. The residue was dissolved in dichloromethane and neutralized with a saturated aqueous solution of sodium bicarbonate. The aqueous layer was extracted with dichloromethane and the organic layers were combined and dried over sodium sulfate. The solid was filtered off and the filtrate was concentrated in vacuo. The residue obtained was purified using an automated silica-gel flash chromatography with a solvent gradient of 0% to 10% methanol and dichloromethane.

M+1 (+ESI)=645.3

Example 51

N-(2-{2-[(2R,5R)-5-(1-benzyl-1H-1,2,3-triazol-5-yl)morpholin-2-yl]ethyl}phenyl)-Nα-(methoxycarbonyl)-β-phenyl-L-phenylalaninamide

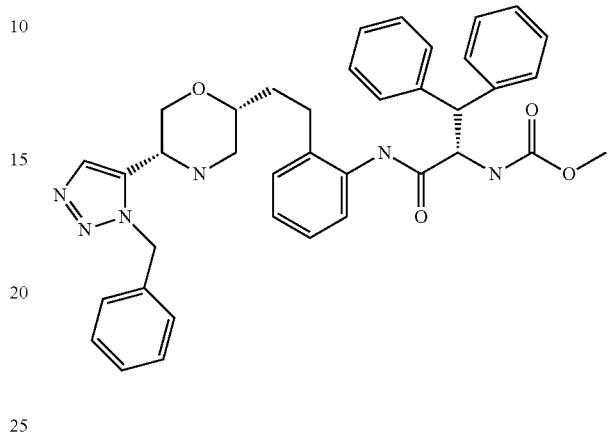

Step 1. tert-butyl (2R,5R)-5-(1-benzyl-1H-1,2,3-triazol-5-yl)-2-[2-(2-{[N-(methoxycarbonyl)-β-phenyl-L-phenylalanyl]amino}phenyl)ethyl]morpholine-4-carboxylate To a solution of tert-butyl (2R,5R)-5-ethynyl-2-[2-(2-{[N-(methoxycarbonyl)-β-phenyl-L-phenylalanyl]amino}phenyl)ethyl]morpholine-4-carboxylate (1.0 equiv) in benzene (0.3M) was added benzyl azide (1.5M) and chloro(1,5-cyclooctadiene)(pentamethylcyclopentadienyl)ruthenium(II). Nitrogen was bubbled through the solution for 5 minutes. The reaction tube was sealed and the mixture was stirred at 80° C. for 12 hours. Upon completion, the reaction mixture was concentrated in vacuo and the residue was directly purified using an automated silica-gel flash chromatography with a solvent gradient of 0% to 20% of methanol and dichloromethane using RediSep Rf Gold™ Columns.

Step 2. N-(2-{2-[(2R,5R)-5-(1-benzyl-1H-1,2,3-triazol-5-yl)morpholin-2-yl]ethyl}phenyl)-Nα-(methoxycarbonyl)-β-phenyl-L-phenylalaninamide Tert-butyl (2R,5R)-5-(1-benzyl-1H-1,2,3-triazol-5-yl)-2-[2-(2-{[N-(methoxycarbonyl)-β-phenyl-L-phenylalanyl]amino}phenyl)ethyl]morpholine-4-carboxylate (1.0 equiv) was dissolved in dichloromethane (0.1M) and trifluoroacetic acid (150 equiv) was added. The reaction mixture was stirred at room temperature for 15 minutes. Upon completion, the volatiles were evaporated under reduced pressure. The residue was dissolved in dichloromethane and neutralized with a saturated aqueous solution of sodium bicarbonate. The aqueous layer was extracted with dichloromethane and the organic layers were combined and dried over sodium sulfate. The solid was filtered off and the filtrate was concentrated in vacuo. The residue obtained was purified using an automated silica-gel flash chromatography with a solvent gradient of 0% to 10% methanol and dichloromethane.

M+1 (+ESI)=645.1

Example 52

Nα-(methoxycarbonyl)-β-phenyl-N-(2-{2-[(2R,5R)-5-(1H-1,2,3-triazol-5-yl)morpholin-2-yl]ethyl}phenyl)-L-phenylalaninamide

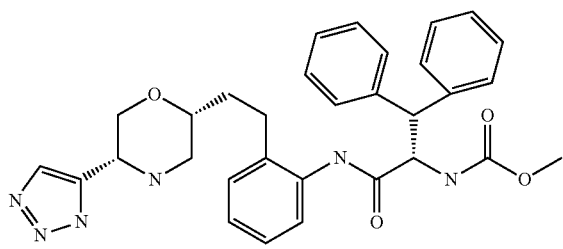 [SMILES: COC(=O)N[C@H](C(=O)Nc1ccccc1CC[C@@H]1CN[C@H](c2cnn[nH]2)CO1)C(c1ccccc1)c1ccccc1]

Step 1. Nα-(methoxycarbonyl)-β-phenyl-N-(2-{2-[(2R,5R)-5-(1H-1,2,3-triazol-5-yl)morpholin-2-yl]ethyl}phenyl)-L-phenylalaninamide To obtain the title compound, follow the procedure described in step 1 and 2 of Example 50, using trimethylsilylazide as the cycloaddition partner for the first step. The purification in the second step was done by reverse phase separation. Buffer NH₄HCO₃ 30 mM. Dimension [21×50 mm]. Column [Max-RP].Gradient (8.3 min) 25-50% (CH₃CN:H₂O).
M+1 (+ESI)=555.1

Example 53

N-(2-{2-[(2R,5R)-5-(1H-indol-2-yl)morpholin-2-yl]ethyl}phenyl)-Nα-(methoxycarbonyl)-β-phenyl-L-phenylalaninamide

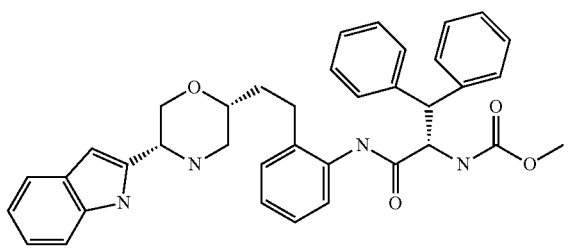 [SMILES: COC(=O)N[C@H](C(=O)Nc1ccccc1CC[C@@H]1CN[C@H](c2cc3ccccc3[nH]2)CO1)C(c1ccccc1)c1ccccc1]

Step 1. tert-butyl (2R,5R)-5-(1H-indol-2-yl)-2-[2-(2-{[N-(methoxycarbonyl)-β-phenyl-L-phenylalanyl]amino}phenyl)ethyl]morpholine-4-carboxylate A mixture of tert-butyl (2R,5R)-5-ethynyl-2-[2-(2-{[N-(methoxycarbonyl)-β-phenyl-L-phenylalanyl]amino}phenyl)ethyl]morpholine-4-carboxylate (1.0 equiv), 2-iodoaniline (1.2 equiv) and bis(triphenylphosphine)palladium(II) chloride (1.0 equiv) was suspended in triethylamine (18.0 equiv) and N,N-dimethylformamide (0.4M). Nitrogen gas was bubbled through the mixture for 5 minutes, then copper (I) iodide (4.0 equiv) was added in one portion. The reaction tube was sealed and the mixture was stirred at room temperature for 15 minutes. Upon completion, an aqueous solution of saturated ammonium chloride was added, along with ethyl acetate. The reaction mixture was stirred for 5 minutes, at which point the layers were separated and the aqueous layer was extracted with ethyl acetate. The organic layers were combined, washed with brine and dried over sodium sulfate. The solid was filtered off and the filtrate was concentrated in vacuo. The remaining N,N-dimethylformamide traces were removed with three successive co-evaporation with heptane. The crude product was purified using an automated silica-gel flash chromatography with a solvent gradient of 0% to 10% methanol in dichloromethane.

Step 2. N-(2-{2-[(2R,5R)-5-(1H-indol-2-yl)morpholin-2-yl]ethyl}phenyl)-Nα-(methoxycarbonyl)-β-phenyl-L-phenylalaninamide Tert-butyl (2R,5R)-5-(1H-indol-2-yl)-2-[2-(2-{[N-(methoxycarbonyl)-β-phenyl-L-phenylalanyl]amino}phenyl)ethyl]morpholine-4-carboxylate (1.0 equiv) was dissolved in dichloromethane (0.1M). Thioanisole (1.0 equiv) and trifluoroacetic acid (150 equiv) were successively added to the mixture. The reaction mixture was stirred at room temperature for 1 hour. Upon completion, the volatiles were evaporated under reduced pressure. The residue was dissolved in dichloromethane and neutralized with a saturated aqueous solution of sodium bicarbonate. The aqueous layer was extracted with dichloromethane and the organic layers were combined and dried over sodium sulfate. The solid was filtered off and the filtrate was concentrated in vacuo. The residue obtained was purified using an automated silica-gel flash chromatography with a solvent gradient of 0% to 10% methanol and dichloromethane.
M+1 (+ESI)=603.1

Example 54

Nα-(methoxycarbonyl)-N-(2-{2-[(2R,5R)-5-(5-methyl-1H-indol-2-yl)morpholin-2-yl]ethyl}phenyl)-β-phenyl-L-phenylalaninamide

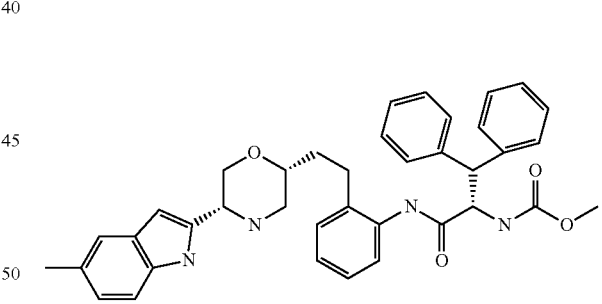

Step 1. Nα-(methoxycarbonyl)-N-(2-{2-[(2R,5R)-5-(5-methyl-1H-indol-2-yl)morpholin-2-yl]ethyl}phenyl)-β-phenyl-L-phenylalaninamide To obtain the title compound, follow the procedure described in step 1 and 2 of Example 53, using 2-iodo-4-methylaniline (1.2 equiv). The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.
M+1 (+ESI)=617.2

Example 55

Nα-(methoxycarbonyl)-3-phenyl-N-[2-(2-{(2R,5R)-5-[5-(trifluoromethyl)-1H-indol-2-yl]morpholin-2-yl}ethyl)phenyl]-L-phenylalaninamide

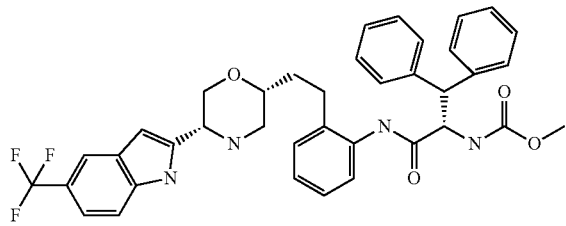 [SMILES: COC(=O)N[C@H](C(=O)Nc1ccccc1CC[C@@H]1CN[C@H](c2cc3cc(C(F)(F)F)ccc3[nH]2)CO1)C(c1ccccc1)c1ccccc1]

Step 1. Nα-(methoxycarbonyl)-β-phenyl-N-[2-(2-{(2R,5R)-5-[5-(trifluoromethyl)-1H-indol-2-yl]morpholin-2-yl}ethyl)phenyl]-L-phenylalaninamide To obtain the title compound, follow the procedure described in step 1 and 2 of Example 53, using 2-iodo-4-(trifluoromethyl)aniline (1.2 equiv). The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=671.2

Example 56

Nα-(methoxycarbonyl)-N-(2-{2-[(2R,5R)-5-(5-methoxy-1H-indol-2-yl)morpholin-2-yl]ethyl}phenyl)-β-phenyl-L-phenylalaninamide

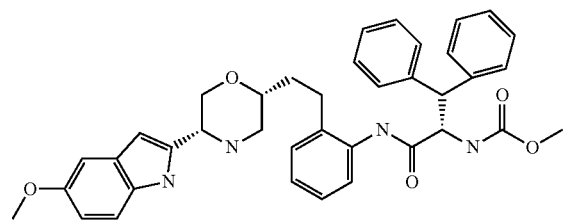

Step 1. Nα-(methoxycarbonyl)-N-(2-{2-[(2R,5R)-5-(5-methoxy-1H-indol-2-yl)morpholin-2-yl]ethyl}phenyl)-β-phenyl-L-phenylalaninamide To obtain the title compound, follow the procedure described in step 1 and 2 of Example 53, using 2-iodo-4-methoxyaniline (1.2 equiv). The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=633.3

Example 57

N-(2-{2-[(2R,5R)-5-(5-chloro-1H-indol-2-yl)morpholin-2-yl]ethyl}phenyl)-Nα-(methoxycarbonyl)-β-phenyl-L-phenylalaninamide

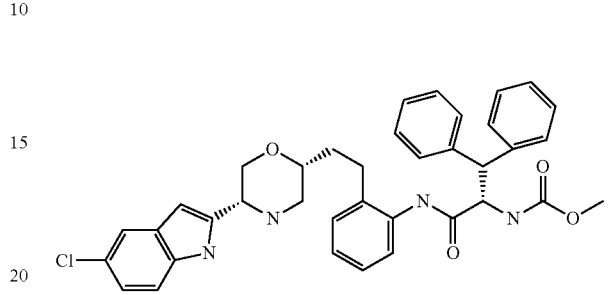

Step 1. N-(2-{2-[(2R,5R)-5-(5-chloro-1H-indol-2-yl)morpholin-2-yl]ethyl}phenyl)-Nα-(methoxycarbonyl)-β-phenyl-L-phenylalaninamide To obtain the title compound, follow the procedure described in step 1 and 2 of Example 53, using 4-chloro-2-iodoaniline (1.2 equiv). The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=637.2

Example 58

N-(2-{2-[(2R,5R)-5-(6-chloro-1H-indol-2-yl)morpholin-2-yl]ethyl}phenyl)-Nα-(methoxycarbonyl)-β-phenyl-L-phenylalaninamide

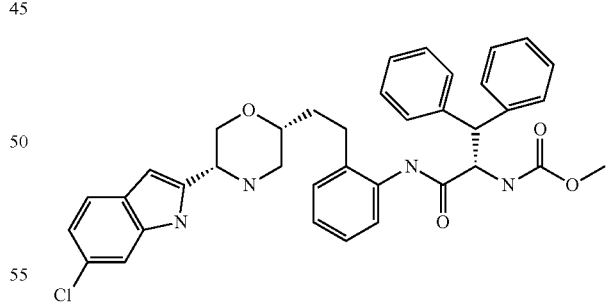

Step 1. N-(2-{2-[(2R,5R)-5-(6-chloro-1H-indol-2-yl)morpholin-2-yl]ethyl}phenyl)-Nα-(methoxycarbonyl)-β-phenyl-L-phenylalaninamide To obtain the title compound, follow the procedure described in step 1 and 2 of Example 53, using 5-chloro-2-iodoaniline (1.2 equiv). The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=637.2

Example 59

N-(2-{2-[(2R,5R)-5-(7-chloro-1H-indol-2-yl)morpholin-2-yl]ethyl}phenyl)-Nα-(methoxycarbonyl)-β-phenyl-L-phenylalaninamide

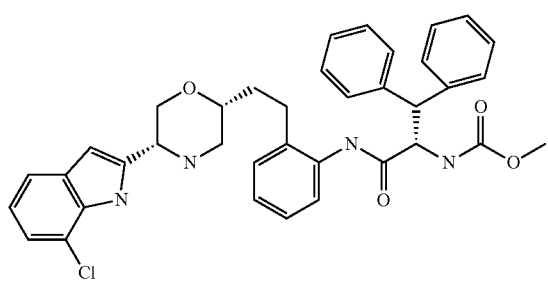 [SMILES: COC(=O)N[C@H](C(=O)Nc1ccccc1CC[C@@H]1CN[C@H](c2cc3cccc(Cl)c3[nH]2)CO1)C(c1ccccc1)c1ccccc1]

Step 1. N-(2-{2-[(2R,5R)-5-(7-chloro-1H-indol-2-yl)morpholin-2-yl]ethyl}phenyl)-Nα-(methoxycarbonyl)-β-phenyl-L-phenylalaninamide To obtain the title compound, follow the procedure described in step 1 and 2 of Example 53, using 2-chloro-6-iodoaniline (1.2 equiv). The residue obtained was purified using an automated silica-gel flash chromatography with a solvent gradient of 0% to 10% methanol and dichloromethane.

M+1 (+ESI)=637.2

Example 60

N-(2-{2-[(2R,5R)-5-(4-chloro-1H-indol-2-yl)morpholin-2-yl]ethyl}phenyl)-Nα-(methoxycarbonyl)-β-phenyl-L-phenylalaninamide

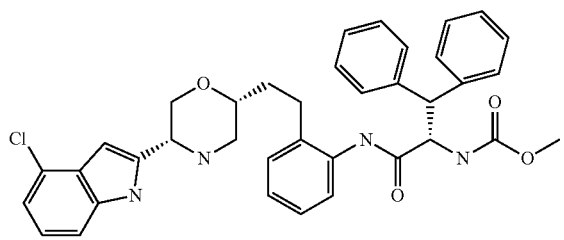 [SMILES: COC(=O)N[C@H](C(=O)Nc1ccccc1CC[C@@H]1CN[C@H](c2cc3c(Cl)cccc3[nH]2)CO1)C(c1ccccc1)c1ccccc1]

Step 1. N-(2-{2-[(2R,5R)-5-(4-chloro-1H-indol-2-yl)morpholin-2-yl]ethyl}phenyl)-Nα-(methoxycarbonyl)-β-phenyl-L-phenylalaninamide To obtain the title compound, follow the procedure described in step 1 and 2 of Example 53, using 3-chloro-2-iodoaniline (1.2 equiv). The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=637.2

Example 61

Nα-(methoxycarbonyl)-β-phenyl-N-(2-{2-[(2R,5R)-5-(1H-pyrrolo[3,2-c]pyridin-2-yl)morpholin-2-yl]ethyl}phenyl)-L-phenylalaninamide

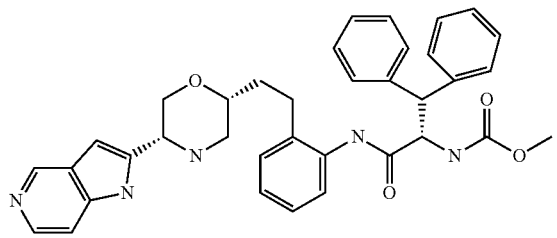 [SMILES: COC(=O)N[C@H](C(=O)Nc1ccccc1CC[C@@H]1CN[C@H](c2cc3cnccc3[nH]2)CO1)C(c1ccccc1)c1ccccc1]

Step 1. Nα-(methoxycarbonyl)-β-phenyl-N-(2-{2-[(2R,5R)-5-(1H-pyrrolo[3,2-c]pyridin-2-yl)morpholin-2-yl]ethyl}phenyl)-L-phenylalaninamide To obtain the title compound, follow the procedure described in step 1 and 2 of Example 53, using 3-iodopyridin-4-amine (1.2 equiv.) and no thioanisole in the second step. The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=604.2

Example 62

Nα-(methoxycarbonyl)-β-phenyl-N-(2-{2-[(2R,5R)-5-(1H-pyrrolo[2,3-b]pyridin-2-yl)morpholin-2-yl]ethyl}phenyl)-L-phenylalaninamide

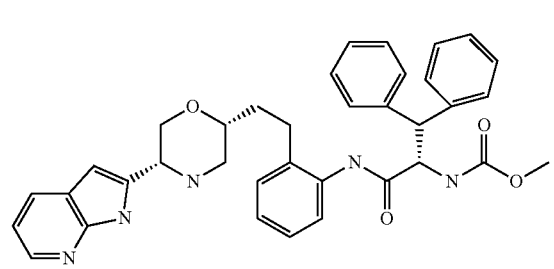 [SMILES: COC(=O)N[C@H](C(=O)Nc1ccccc1CC[C@@H]1CN[C@H](c2cc3cccnc3[nH]2)CO1)C(c1ccccc1)c1ccccc1]

Step 1. Nα-(methoxycarbonyl)-β-phenyl-N-(2-{2-[(2R,5R)-5-(1H-pyrrolo[2,3-b]pyridin-2-yl)morpholin-2-yl]ethyl}phenyl)-L-phenylalaninamide To obtain the title compound, follow the procedure described in step 1 and 2 of Example 53, using 3-iodopyridin-2-amine (1.2 equiv) and no thioanisole in the second step. The purification in the second step was done using SCX cartridge: the residue was dissolved in methanol, loaded onto the acidic silica and rinsed with methanol for five column volumes. The pure product was released with a five column volume of a solution of ammonium hydroxide 10% in methanol. The solution was concentrated in vacuo to afford the desired product.

M+1 (+ESI)=604.3

Example 63

(3S)—N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)-3-(3-fluoropyridin-4-yl)propanamide

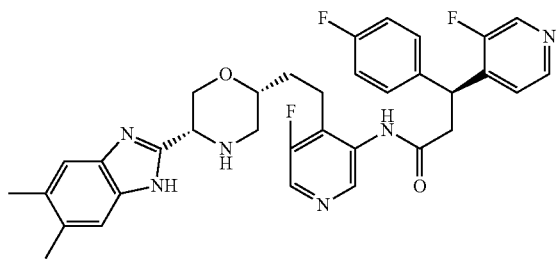 [SMILES: Cc1cc2nc([C@@H]3CO[C@H](CCc4c(F)cncc4NC(=O)C[C@@H](c4ccc(F)cc4)c4ccncc4F)CN3)[nH]c2cc1C]

Step 1: (R,E)-3-(3-(3-Fluoropyridin-4-yl)acryloyl)-4-phenyloxazolidin-2-one

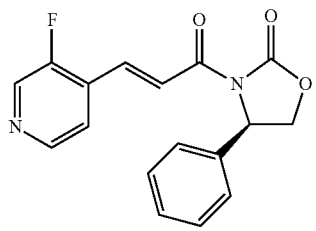 [SMILES: O=C(/C=C/c1ccncc1F)N1C(=O)OC[C@H]1c1ccccc1]

To a stirred solution of (R)-dimethyl (2-oxo-2-(2-oxo-5-phenyloxazolidin-3-yl)ethyl)phosphonate (3.20 g, 9.6 mmol), prepared as described in Example 64, in THF (100 mL) was added potassium tert-butoxide (9.60 mL, 1M in THF, 9.60 mmol) and mixture was stirred at room temperature for 20 min. The solution of 3-fluoroisonicotinaldehyde (1.00 g, 8.00 mmol) was added dropwise and reaction mixture was stirred at room temperature for 2 h. The reaction mixture was quenched with water, extracted with EtOAc (2×100 mL). The organic layer was washed with brine (100 mL), dried (Na$_2$SO$_4$), filtered and concentrated under reduced pressure. The residue was purified by 40 g SiO$_2$ column using a gradient elution of 0-50% EtOAc in hexanes. Fractions containing product were combined and the solvents were removed in vacuo to provide the product (2.30 g, 95%) as a white solid. MS: m/z=313 (M+H$^+$).

Step 2: (R)-3-((S)-3-(4-Fluorophenyl)-3-(3-fluoropyridin-4-yl)propanoyl)-4-phenyloxazolidin-2-one

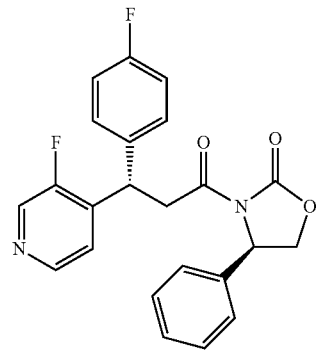 [SMILES: O=C(C[C@@H](c1ccc(F)cc1)c1ccncc1F)N1C(=O)OC[C@H]1c1ccccc1]

To a suspension of CuBr.Me$_2$S (1.98 g, 9.60 mmol) in THF (50.0 mL) was added dimethyl sulphide (10.0 mL) at −40° C. The reaction mixture was stirred for 5 min and 4-fluorophenylmagnesium bromide (12.8 mL, 1M in THF, 12.8 mmol) was added dropwise over a period of 15 min. The reaction mixture was stirred at same temperature for 30 min and then stirred at −20° C. for 20 min. A solution of (R,E)-3-(3-(3-fluoropyridin-4-yl)acryloyl)-4-phenyloxazolidin-2-one (2.00 g, 6.41 mmol) in THF (20.0 mL) was added dropwise at −20° C. and reaction mixture was stirred at −20° C. for 4 h. The reaction mixture was quenched with aqueous ammonium chloride solution (50.0 mL) and extracted with EtOAc (2×50.0 mL). The organic layer was washed with brine (100 mL), dried (Na$_2$SO$_4$), filtered and concentrated under reduced pressure. The residue was purified by 120 g SiO$_2$ column using a gradient elution of 0-40% EtOAc in hexanes. Fractions containing product were combined and the solvents were removed in vacuo to provide the product (1.60 g, 61%) as an off white solid. MS: m/z=409 (M+H$^+$).

Step 3: (S)-3-(4-Fluorophenyl)-3-(3-fluoropyridin-4-yl)propanoic acid

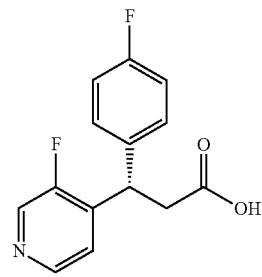 [SMILES: O=C(O)C[C@@H](c1ccc(F)cc1)c1ccncc1F]

To a precooled (0° C.) solution of (R)-3-((S)-3-(4-fluorophenyl)-3-(3-fluoropyridin-4-yl)propanoyl)-4-phenyloxazolidin-2-one (0.80 g, 2.05 mmol) in THF (15.0 mL) and water (5.00 mL) was added 30% hydrogen peroxide (1.30 mL) drop-wise and stirred for 10 min. A solution of LiOH (73 mg, 3.00 mmol) in water (2.00 mL) was added at 0° C. and reaction mixture was stirred at 0° C. for 2 h. The reaction mixture was quenched with saturated solution of sodium sulphite (100 mL), water (500 mL) and extracted with EtOAc (2×50.0 mL). The aqueous phase was acidified to pH 4 and extracted with EtOAc (2×50.0 mL). The combined EtOAc extracts were washed with brine (100 mL), dried (Na$_2$SO$_4$), filtered and concentrated under reduced pressure to provide product (0.40 g, 80%) as a white solid. MS: m/z=264 (M+H$^+$).

Step 4: (R)—N-(5-Fluoro-4-iodopyridin-3-yl)-3-(4-fluorophenyl)-3-(3-fluoropyridin-4-yl)propanamide

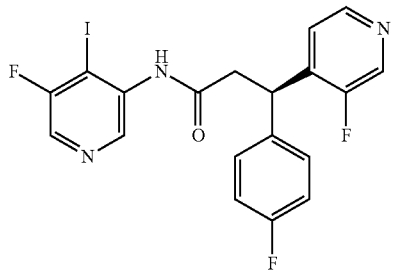 [SMILES: O=C(C[C@H](c1ccc(F)cc1)c1ccncc1F)Nc1cncc(F)c1I]

To a stirred solution of (S)-3-(4-fluorophenyl)-3-(3-fluoropyridin-4-yl)propanoic acid (0.75 g, 2.85 mmol) and 5-fluoro-4-iodopyridin-3-amine (0.68 g, 2.85 mmol) in pyridine (10.0 mL) at −20° C. was added POCl$_3$ (0.29 mL, 3.13 mmol) dropwise and reaction mixture was warmed to 0° C. over a period of 2 h. The reaction mixture was quenched with saturated aqueous solution of KH$_2$PO$_4$ (1.00 mL), extracted with EtOAc (3×20.0 mL) and combined organic extract were washed with brine (25.0 mL), dried (Na$_2$SO$_4$), filtered and concentrated under reduced pressure. The residue was purified by 40 g SiO$_2$ column using a gradient elution of 0-40% EtOAc in hexanes. Fractions containing product were combined and the solvents were removed in vacuo to provide the product (1.10 g, 84%) as a yellow gum. MS: m/z=484 (M+H$^+$).

Step 5: (2R,5S)-tert-Butyl 5-(((tert-butyldimethylsilyl)oxy)methyl)-2-((3-fluoro-5-((R)-3-(4-fluorophenyl)-3-(3-fluoropyridin-4-yl)propanamido)pyridin-4-yl)ethynyl)morpholine-4-carboxylate

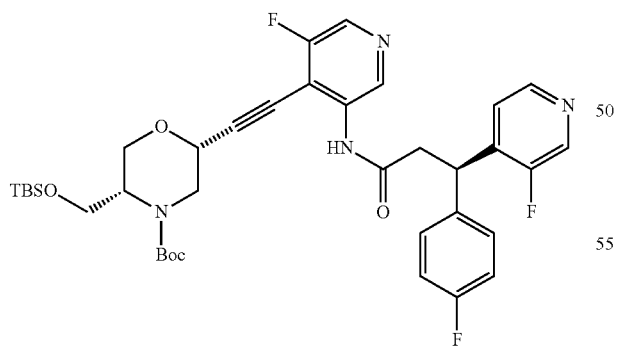

To a stirred solution of (R)—N-(5-fluoro-4-iodopyridin-3-yl)-3-(4-fluorophenyl)-3-(3-fluoropyridin-4-yl)propanamide (0.74 g, 1.54 mmol) and (2R,5S)-tert-butyl 5-(((tert-butyldimethylsilyl)oxy)methyl)-2-ethynylmorpholine-4-carboxylate (0.50 g, 1.40 mmol) in acetonitrile (20.0 mL) and mixture was degassed with Argon for 15 min. Added CuI (26 mg, 0.0.14 mmol), PdCl$_2$(PPh$_3$)$_2$ (68 mg, 0.098 mmol) and mixture was stirred at 70° C. for 6 h. The solvent was removed under reduced pressure and water (25.0 mL) was added to the residue. The mixture was extracted with EtOAc (3×25.0 mL) and combined organic extract were washed with brine (25.0 mL), dried (Na$_2$SO$_4$), filtered and concentrated under reduced pressure. The residue was purified by 40 g SiO$_2$ column using a gradient elution of 0-30% EtOAc in hexanes. Fractions containing product were combined and the solvents were removed in vacuo to provide the product (0.45 g, 45%) as a colourless gum. MS: m/z=711 (M+H$^+$).

Step 6: (2R,5S)-tert-Butyl 5-(((tert-butyldimethylsilyl)oxy)methyl)-2-(2-(3-fluoro-5-((S)-3-(4-fluorophenyl)-3-(3-fluoropyridin-4-yl)propanamido)pyridin-4-yl)ethyl)morpholine-4-carboxylate

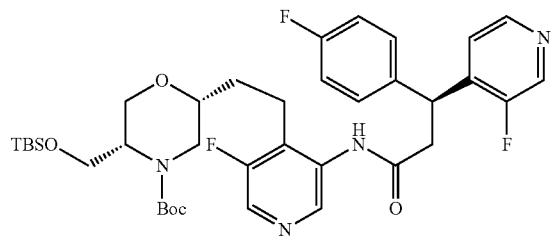 [SMILES: CC(C)(C)OC(=O)N1C[C@@H](CCc2c(F)cncc2NC(=O)C[C@@H](c2ccc(F)cc2)c2ccncc2F)OC[C@H]1CO[Si](C)(C)C(C)(C)C]

To a solution of (2R,5S)-tert-butyl 5-(((tert-butyldimethylsilyl)oxy)methyl)-2-((3-fluoro-5-((R)-3-(4-fluorophenyl)-3-(3-fluoropyridin-4-yl)propanamido)pyridin-4-yl)ethynyl)morpholine-4-carboxylate (0.42 g, 0.82 mmol) in EtOH (20.0 mL) was added Pd(OH)$_2$ (84 mg, 20% by wt) and mixture was stirred in parr shaker at 60 psi under H$_2$ atmosphere for 8 h. The mixture was filtered over pad of celite. The celite bed was washed with EtOAc (2×25.0 mL). The combined organic extract were washed with brine (25.0 mL), dried (Na$_2$SO$_4$), filtered and concentrated under reduced pressure to provide product (0.42 g, crude) as yellow gum. The crude product was directly used in the next step without purification. MS: m/z=715 (M+H$^+$).

Step 7: (2R,5R)-tert-Butyl 2-(2-(3-fluoro-5-((S)-3-(4-fluorophenyl)-3-(3-fluoropyridin-4-yl)propanamido)pyridin-4-yl)ethyl)-5-(hydroxymethyl)morpholine-4-carboxylate

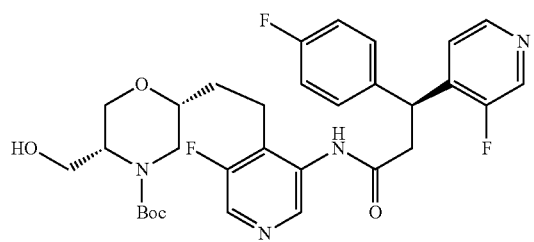 [SMILES: CC(C)(C)OC(=O)N1C[C@@H](CCc2c(F)cncc2NC(=O)C[C@@H](c2ccc(F)cc2)c2ccncc2F)OC[C@H]1CO]

To a solution of (2R,5S)-tert-butyl 5-(((tert-butyldimethylsilyl)oxy)methyl)-2-(2-(3-fluoro-5-((S)-3-(4-fluorophenyl)-3-(3-fluoropyridin-4-yl)propanamido)pyridin-4-yl)ethyl)morpholine-4-carboxylate (0.42 g, 0.58 mmol) in THF (5.00 mL) was added TBAF (0.88 mL, 1.0 M in THF, 0.88 mmol) and mixture was stirred at room temperature for 1 h.

The solvent was removed under reduced pressure. The residue was purified by 24 g SiO$_2$ column using a gradient elution of 0-20% MeOH in EtOAc. Fractions containing product were combined and the solvents were removed in vacuo to provide the product (0.28 mg, 81% over two steps) as a colourless gum. MS: m/z=601 (M+H$^+$).

Step 8: (2R,5S)-tert-Butyl 2-(2-(3-fluoro-5-((S)-3-(4-fluorophenyl)-3-(3-fluoropyridin-4-yl)propanamido)pyridin-4-yl)ethyl)-5-formylmorpholine-4-carboxylate

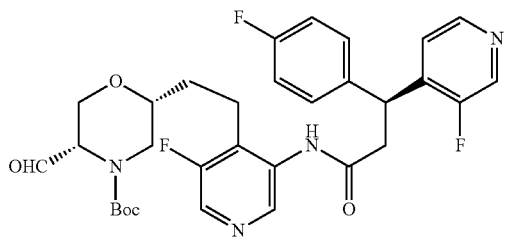 [SMILES: CC(C)(C)OC(=O)N1C[C@@H](CCc2c(F)cncc2NC(=O)C[C@@H](c2ccc(F)cc2)c2ccncc2F)OC[C@H]1C=O]

To a solution of (2R,5R)-tert-butyl 2-(2-(3-fluoro-5-((S)-3-(4-fluorophenyl)-3-(3-fluoropyridin-4-yl)propanamido)pyridin-4-yl)ethyl)-5-(hydroxymethyl)morpholine-4-carboxylate (0.280 g, 0.46 mmol) in CH$_2$Cl$_2$ (10.0 mL) was added Dess-Martin periodinane (0.34 g, 0.69 mmol) and mixture was stirred at 0° C. for 2 h. The reaction mixture was diluted with CH$_2$Cl$_2$ (50.0 mL) and quenched with saturated solution of Na$_2$S$_2$O$_3$ (10.0 mL) and NaHCO$_3$ solution (10.0 mL). The organic layer was separated washed with brine (25.0 mL), dried (Na$_2$SO$_4$), filtered and concentrated under reduced pressure to provide product (0.25 g, crude) as yellow gum. The crude product was directly used in the next step without purification.
MS: m/z=599 (M+H$^+$).

Step 9: (2R,5R)-tert-Butyl 5-(5,6-dimethyl-1H-benzo[d]imidazol-2-yl)-2-(2-(3-fluoro-5-((S)-3-(4-fluorophenyl)-3-(3-fluoropyridin-4-yl)propanamido)pyridin-4-yl)ethyl)morpholine-4-carboxylate

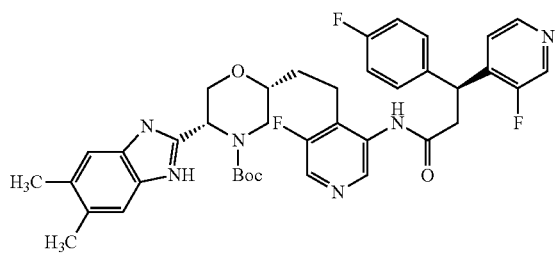 [SMILES: Cc1cc2nc([C@@H]3CO[C@H](CCc4c(F)cncc4NC(=O)C[C@@H](c4ccc(F)cc4)c4ccncc4F)CN3C(=O)OC(C)(C)C)[nH]c2cc1C]

A mixture of 4,5-dimethylbenzene-1,2-diamine (85.2 mg, 0.63 mmol) and Na$_2$H$_2$O$_5$ (0.13 g, 1.25 mmol) in DMA (10.0 mL) was heated at 100° C. and solution of (2R,5S)-tert-butyl 2-(2-(3-fluoro-5-((S)-3-(4-fluorophenyl)-3-(3-fluoropyridin-4-yl)propanamido)pyridin-4-yl)ethyl)-5-formylmorpholine-4-carboxylate (0.25 g, 0.40 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extracts were washed with brine (25.0 mL), dried (Na$_2$SO$_4$), filtered and concentrated under reduced pressure. The residue was purified by 24 g SiO$_2$ column using a gradient elution of 0-60% EtOAc in hexanes. Fractions containing product were combined and the solvents were removed in vacuo to provide the product (0.17 g, 52% over two steps) as off white solid. MS: m/z=715 (M+H$^+$).

Step 10: (3S)—N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)-3-(3-fluoropyridin-4-yl)propanamide To a solution of (2R,5R)-tert-butyl 5-(5,6-dimethyl-1H-benzo[d]imidazol-2-yl)-2-(2-(3-fluoro-5-((S)-3-(4-fluorophenyl)-3-(3-fluoropyridin-4-yl)propanamido)pyridin-4-yl)ethyl)morpholine-4-carboxylate (0.17 g, 0.23 mmol) in CH$_2$Cl$_2$ (10.0 mL) was added TFA (2.00 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (92 mg, 39%) as a white solid. MS: m/z=615 (M+H$^+$).

Example 64

(3S)-3-(3,5-difluorophenyl)-N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)propanamide

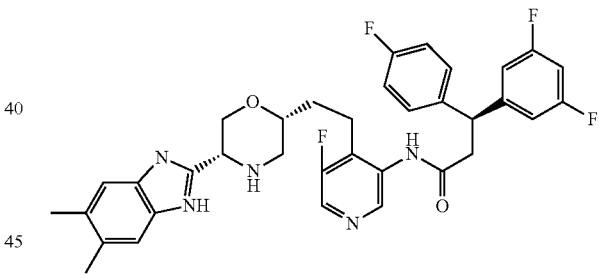

Step 1: (R)-3-(2-Bromoacetyl)-4-phenyloxazolidin-2-one

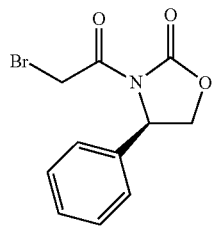

A solution of (R)-4-phenyloxazolidin-2-one (100 g, 613 mmol) in THF (2.00 L) under a nitrogen atmosphere was cooled to −78° C. in dry ice-acetone bath. To the stirred solution was added n-BuLi (337 mL, 2 M solution in cyclohexane, 675 mmol) dropwise over a period of 30 min, followed by the addition of 2-bromoacetyl bromide (123 g, 613 mmol) over 15 min. The resulting solution was stirred at 25° C. for 2 h. The reaction was quenched with aqueous NH₄Cl (500 mL), and the mixture was extracted with EtOAc (3×1.00 L). The combined organic extracts were washed with water (500 mL), brine (500 mL), dried (MgSO₄), filtered, and the solvent was removed under reduced pressure to get the product (175 g, crude) as a brown solid. The crude product was used directly in the next step without purification.

Step 2: (R)-Dimethyl [2-oxo-2-(2-oxo-4-phenyloxazolidin-3-yl)ethyl]phosphonate

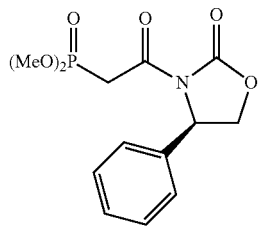

A solution of (R)-3-(2-bromoacetyl)-4-phenyloxazolidin-2-one (175 g, 616 mmol) and trimethyl phosphite (83.3 g, 671 mmol) in toluene (870 mL) was heated to reflux for 16 h. The reaction mixture was cooled to room temperature and the solvent was concentrated under reduced pressure to get a brown colored gum, which was triturated with 1:1 CH₂Cl₂ and hexanes (250 mL) to provide a brown solid. The solid was collected by filtration under reduced pressure and washed with CH₂Cl₂ (50.0 mL) to provide the product (98.8 g, 52% over two steps) as light brown solid.

Step 3: (R,E)-3-(3-(3,5-Difluorophenyl)acryloyl)-5-phenyloxazolidin-2-one

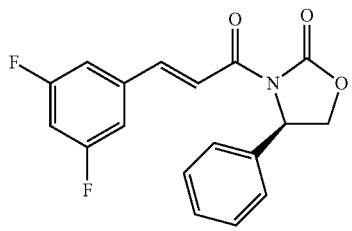

To a stirred solution of (R)-dimethyl (2-oxo-2-(2-oxo-5-phenyloxazolidin-3-yl)ethyl)phosphonate (2.79 g, 8.4 mmol) in THF (40.0 mL) was added potassium tert-butoxide (8.40 mL, 1 M in THF, 8.4 mmol) and mixture was stirred at room temperature for 20 min. A solution of 3,5-difluorobenzaldehyde (1.00 g, 7.04 mmol) in THF (30.0 mL) was added dropwise and reaction mixture was stirred at room temperature for 3 h. The reaction mixture was quenched with water (30.0 mL), extracted with EtOAc (2×100 mL). The organic layer was washed with brine (100 mL), dried (Na₂SO₄), filtered and concentrated under reduced pressure. The residue was purified by 40 g SiO₂ column using a gradient elution of 0-50% EtOAc in hexanes. Fractions containing product were combined and the solvents were removed in vacuo to provide the product (2.00 g, 86%) as a white solid. MS: m/z=330 (M+H⁺).

Step 4: (R)-3-((R)-3-(3,5-Difluorophenyl)-3-(4-fluorophenyl)propanoyl)-5-phenyloxazolidin-2-one

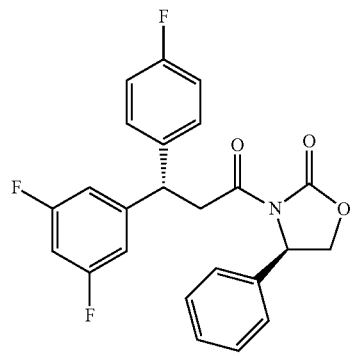 [SMILES: O=C(C[C@@H](c1ccc(F)cc1)c1cc(F)cc(F)c1)N1C(=O)OC[C@H]1c1ccccc1]

To a suspension of CuBr.Me₂S (1.80 g, 9.13 mmol) in THF (50.0 mL) was added dimethyl sulphide (10.0 mL) at −40° C. The reaction mixture was stirred for 5 min and 4-fluorophenylmagnesium bromide (12.1 mL, 1M in THF, 12.1 mmol) was added dropwise over a period of 15 min. The reaction mixture was stirred at same temperature for 30 min and then stirred at −20° C. for 20 min. The solution of (R,E)-3-(3-(3,5-difluorophenyl)acryloyl)-5-phenyloxazolidin-2-one (2.00 g, 6.09 mmol) was added dropwise at −20° C. and reaction mixture was stirred at −20° C. for 4 h. The reaction mixture was quenched with aqueous ammonium chloride solution and extracted with EtOAc (2×50.0 mL). The organic layer was washed with brine (100 mL), dried (Na₂SO₄), filtered and concentrated under reduced pressure. The residue was purified by 120 g SiO₂ column using a gradient elution of 0-30% EtOAc in hexanes. Fractions containing product were combined and the solvents were removed in vacuo to provide the product (2.20 g, 88%) as a white solid. MS: m/z=426 (M+H⁺).

Step 5: (R)-3-(3,5-Difluorophenyl)-3-(4-fluorophenyl)propanoic acid

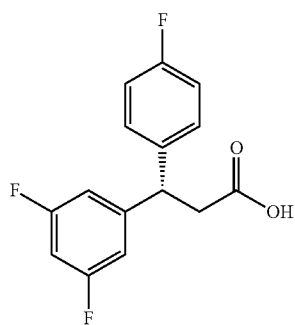 [SMILES: O=C(O)C[C@@H](c1ccc(F)cc1)c1cc(F)cc(F)c1]

To a precooled (0° C.) solution of (R)-3-((R)-3-(3,5-difluorophenyl)-3-(4-fluorophenyl)propanoyl)-5-phenyloxazolidin-2-one (2.50 g, 5.58 mmol) in THF (30.0 mL) and water (10.0 mL) was added 30% hydrogen peroxide (2.00 mL) drop-wise and stirred for 10 min. A solution of LiOH (0.21 g, 8.82 mmol) in water (3.00 mL) was added at 0° C.

and reaction mixture was stirred at 0° C. for 2 h. The reaction mixture was quenched with saturated solution of sodium sulphite (100 mL), water (500 mL) and extracted with EtOAc (2×50.0 mL). The aqueous phase was acidified to pH 3 and extracted with EtOAc (2×50.0 mL). The combined EtOAc extracts were washed with brine (100 mL), dried (Na$_2$SO$_4$), filtered and concentrated under reduced pressure to provide product (0.40 g, 86%) as a white solid. MS: m/z=281 (M+H$^+$).

Step 6: (R)-3-(3,5-Difluorophenyl)-N-(5-fluoro-4-iodopyridin-3-yl)-3-(4-fluorophenyl)propanamide

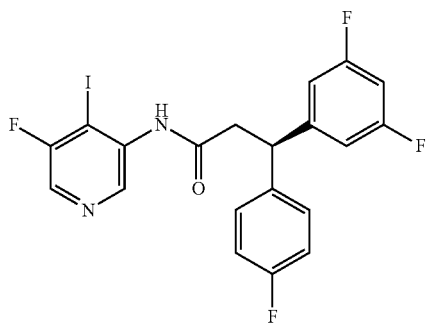 [SMILES: O=C(C[C@H](c1ccc(F)cc1)c1cc(F)cc(F)c1)Nc1cncc(F)c1I]

To a stirred solution of (R)-3-(3,5-difluorophenyl)-3-(4-fluorophenyl)propanoic acid (0.50 g, 1.78 mmol) and 5-fluoro-4-iodopyridin-3-amine (0.42 g, 1.78 mmol) in pyridine (5.00 mL) at −20° C. was added POCl$_3$ (0.18 mL, 1.95 mmol) dropwise and reaction mixture was warmed to 0° C. over a period of 2 h. The reaction mixture was quenched with saturated solution of KH$_2$PO$_4$ (1.00 mL), extracted with EtOAc (3×20.0 mL) and combined organic extract were washed with brine (25.0 mL), dried (Na$_2$SO$_4$), filtered and concentrated under reduced pressure. The residue was purified by 40 g SiO$_2$ column using a gradient elution of 0-40% EtOAc in hexanes. Fractions containing product were combined and the solvents were removed in vacuo to provide the product (0.73 g, 82%) as a colourless gum. MS: m/z=501 (M+H$^+$).

Step 7: (2R,5S)-tert-Butyl 5-(((tert-butyldimethylsilyl)oxy)methyl)-2-((3-((R)-3-(3,5-difluorophenyl)-3-(4-fluorophenyl)propanamido)-5-fluoropyridin-4-yl)ethynyl)morpholine-4-carboxylate

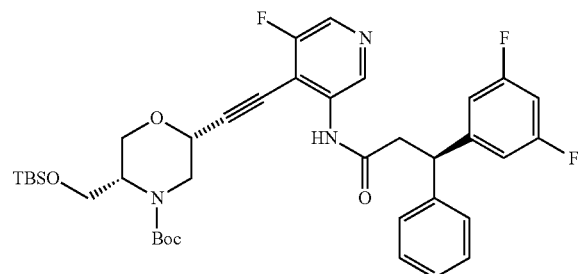

To a stirred solution of (R)-3-(3,5-difluorophenyl)-N-(5-fluoro-4-iodopyridin-3-yl)-3- (4-fluorophenyl)propanamide (1.54 g, 3.09 mmol) and (2R,5S)-5-(((tert-butyldimethylsilyl)oxy)methyl)-2-ethynylmorpholine (1.00 g, 2.81 mmol) in acetonitrile (20.0 mL) and mixture was degassed with Argon for 15 min. Added CuI (53 mg, 0.28 mmol), PdCl$_2$(PPh$_3$)$_2$ (138 mg, 0.19 mmol) and mixture was stirred at 70° C. for 6 h. The solvent was removed under reduced pressure and water (20.0 mL) was added to the residue. The mixture was extracted with EtOAc (3×20.0 mL) and combined organic extracts were washed with brine (25.0 mL), dried (Na$_2$SO$_4$), filtered and concentrated under reduced pressure. The residue was purified by 40 g SiO$_2$ column using a gradient elution of 0-30% EtOAc in hexanes. Fractions containing product were combined and the solvents were removed in vacuo to provide the product (1.20 g, 63%) as a colourless gum. MS: m/z=728 (M+H$^+$).

Step 8: (2R,5S)-tert-Butyl 5-(((tert-butyldimethylsilyl)oxy)methyl)-2-(2-(3-((S)-3-(3,5-difluorophenyl)-3-(4-fluorophenyl)propanamido)-5-fluoropyridin-4-yl)ethyl)morpholine-4-carboxylate

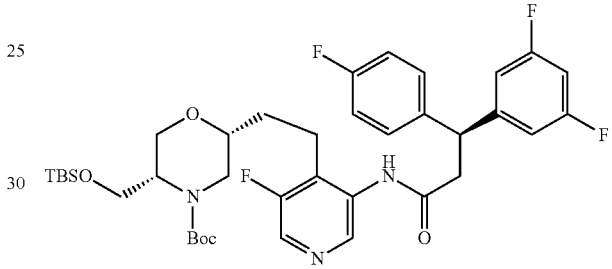

To a solution of (2R,5S)-tert-butyl 5-(((tert-butyldimethylsilyl)oxy)methyl)-2-((3-((R)-3-(3,5-difluorophenyl)-3-(4-fluorophenyl)propanamido)-5-fluoropyridin-4-yl)ethynyl)morpholine-4-carboxylate (0.60 g, 0.82 mmol) in EtOH (10.0 mL) was added Pd(OH)$_2$ (60 mg, 10% by wt) and mixture was stirred in parr shaker at 50 psi under H$_2$ atmosphere for 4 h. The mixture was filtered over pad of celite. The celite bed was washed with EtOAc (2×25.0 mL). The combined organic extract were washed with brine (25.0 mL), dried (Na$_2$SO$_4$), filtered and concentrated under reduced pressure to provide product (0.56 g, 93%) as yellow gum. The crude product was directly used in next step without purification. MS: m/z=732 (M+H$^+$).

Step 9: (2R,5R)-tert-Butyl-2-(2-(3-((S)-3-(3,5-difluorophenyl)-3-(4-fluorophenyl)propanamido)-5-fluoropyridin-4-yl)ethyl)-5-(hydroxymethyl)morpholine-4-carboxylate

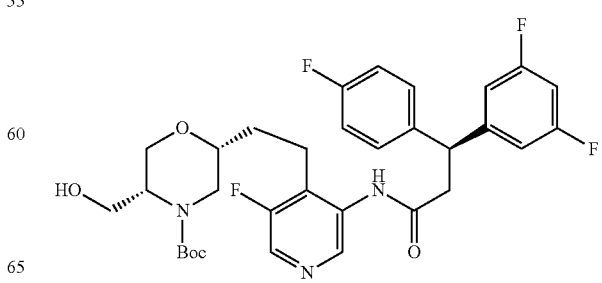

To a solution of (2R,5S)-tert-butyl 5-(((tert-butyldimethylsilyl)oxy)methyl)-2-(2-(3-((S)-3-(3,5-difluorophenyl)-3-(4-fluorophenyl)propanamido)-5-fluoropyridin-4-yl)ethyl)morpholine-4-carboxylate (0.33 g, 0.40 mmol) in THF (5.00 mL) was added TBAF (0.61 mL, 1.0 M in THF, 0.61 mmol) and mixture was stirred at room temperature for 1 h. The solvent was removed under reduced pressure. The residue was purified by 24 g SiO₂ column using a gradient elution of 0-60% EtOAc in hexanes. Fractions containing product were combined and the solvents were removed in vacuo to provide the product (0.27 g, 89%) as a colourless gum. MS: m/z=618 (M+H⁺).

Step 10: (2R,5S)-tert-Butyl 2-(2-(3-((S)-3-(3,5-difluorophenyl)-3-(4-fluorophenyl)propanamido)-5-fluoropyridin-4-yl)ethyl)-5-formylmorpholine-4-carboxylate

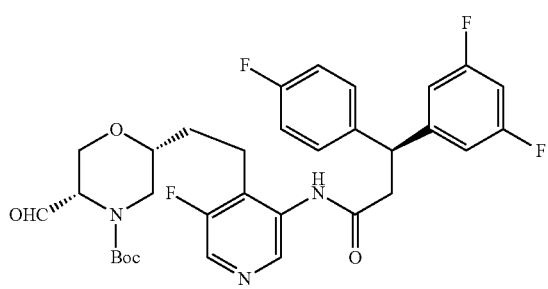 [SMILES: CC(C)(C)OC(=O)N1C[C@@H](CCc2c(F)cncc2NC(=O)C[C@@H](c2ccc(F)cc2)c2cc(F)cc(F)c2)OC[C@H]1C=O]

To a solution of (2R,5R)-tert-butyl 2-(2-(3-((S)-3-(3,5-difluorophenyl)-3-(4-fluorophenyl)propanamido)-5-fluoropyridin-4-yl)ethyl)-5-(hydroxymethyl)morpholine-4-carboxylate (0.25 g, 0.40 mmol) in CH₂Cl₂ (10.0 mL) was added Dess-Martin periodinane (0.26 g, 0.60 mmol) and mixture was stirred at 0° C. for 2 h. The reaction mixture was diluted with CH₂Cl₂ (50.0 mL) and quenched with saturated solution of Na₂S₂O₃ (10.0 mL) and NaHCO₃ solution (10.0 mL). The organic layer was separated, washed with brine (25.0 mL), dried (Na₂SO₄), filtered and concentrated under reduced pressure to provide product (0.25 g, crude) as yellow gum. The crude product was directly used for next step without purification. MS: m/z=616 (M+H⁺).

Step 11: (2R,5R)-tert-Butyl 2-(2-(3-((S)-3-(3,5-difluorophenyl)-3-(4-fluorophenyl)propanamido)-5-fluoropyridin-4-yl)ethyl)-5-(5,6-dimethyl-1H-benzo[d]imidazol-2-yl)morpholine-4-carboxylate

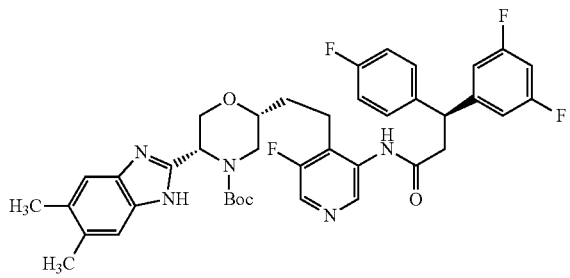 [SMILES: Cc1cc2nc([C@@H]3CO[C@H](CCc4c(F)cncc4NC(=O)C[C@@H](c4ccc(F)cc4)c4cc(F)cc(F)c4)CN3C(=O)OC(C)(C)C)[nH]c2cc1C]

A mixture of 4,5-dimethylbenzene-1,2-diamine (81 mg, 0.60 mmol) and Na₂S₂O₅ (0.12 g, 1.2 mmol) in DMA (10.0 mL) was heated at 100° C. and solution of (2R,5S)-tert-butyl 2-(2-(3-((S)-3-(3,5-difluorophenyl)-3-(4-fluorophenyl)propanamido)-5-fluoropyridin-4-yl)ethyl)-5-formylmorpholine-4-carboxylate (0.25 g, 0.40 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extract were washed with brine (25.0 mL), dried (Na₂SO₄), filtered and concentrated under reduced pressure. The residue was purified by 24 g SiO₂ column using a gradient elution of 0-60% EtOAc in hexanes. Fractions containing product were combined and the solvents were removed in vacuo to provide the product (95 mg, 37% over two steps) as off white solid. MS: m/z=732 (M+H⁺).

Step 12: (3S)-3-(3,5-difluorophenyl)-N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)propanamide To a solution of (2R,5R)-tert-butyl 2-(2-(3-((S)-3-(3,5-difluorophenyl)-3-(4-fluorophenyl)propanamido)-5-fluoropyridin-4-yl)ethyl)-5-(5,6-dimethyl-1H-benzo[d]imidazol-2-yl)morpholine-4-carboxylate (95 mg, 0.12 mmol) in CH₂Cl₂ (5.00 mL) was added TFA (1.00 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (51 mg, 53%) as a white solid. MS: m/z=632 (M+H⁺).

Example 65

(3S)—N-(4-{2-[(2R,5R)-5-(6-chloro-1H-benzimidazol-2-yl)morpholin-2-yl]ethyl}-5-fluoropyridin-3-yl)-3-(3,5-difluorophenyl)-3-(4-fluorophenyl)propanamide

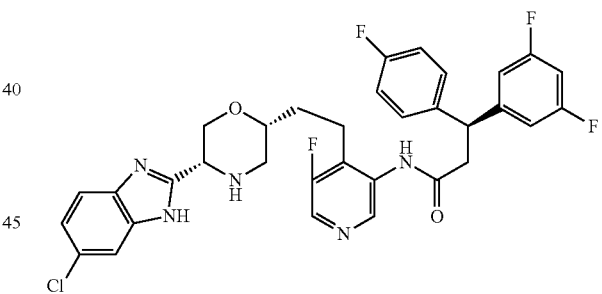

Step 1: (2R,5R)-tert-Butyl 5-(6-chloro-1H-benzo[d]imidazol-2-yl)-2-(2-(3-((S)-3-(3,5-difluorophenyl)-3-(4-fluorophenyl)propanamido)-5-fluoropyridin-4-yl)ethyl)morpholine-4-carboxylate

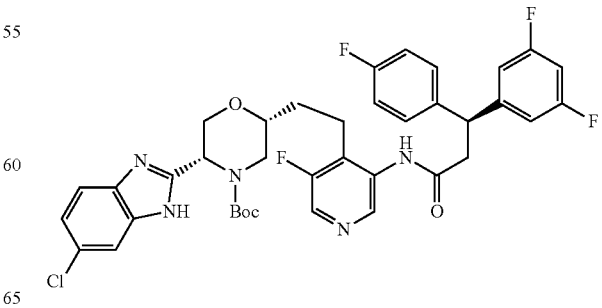

A mixture of 4-chlorobenzene-1,2-diamine (0.10 g, 0.60 mmol) and Na₂S₂O₅ (0.15 g, 1.2 mmol) in DMA (20.0 mL)

was heated at 100° C. and solution (2R,5S)-tert-butyl 2-(2-(3-((S)-3-(3,5-difluorophenyl)-3-(4-fluorophenyl)propanamido)-5-fluoropyridin-4-yl)ethyl)-5-formylmorpholine-4-carboxylate (0.30 g, 0.48 mmol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extracts were washed with brine (25.0 mL), dried (Na$_2$SO$_4$), filtered and concentrated under reduced pressure. The residue was purified by 24 g SiO$_2$ column using a gradient elution of 0-60% EtOAc in hexanes. Fractions containing product were combined and the solvents were removed in vacuo to provide the product (0.10 mg, 29% over two steps) as off white solid.
MS: m/z=738 (M+H$^+$).

Step 2: (3S)—N-(4-{2-[(2R,5R)-5-(6-chloro-1H-benzimidazol-2-yl)morpholin-2-yl]ethyl}-5-fluoropyridin-3-yl)-3-(3,5-difluorophenyl)-3-(4-fluorophenyl)propanamide To a solution of ((2R,5R)-tert-butyl 5-(6-chloro-1H-benzo[d]imidazol-2-yl)-2-(2-(3-((S)-3-(3,5-difluorophenyl)-3-(4-fluorophenyl)propanamido)-5-fluoropyridin-4-yl)ethyl)morpholine-4-carboxylate (0.10 g, 0.14 mmol) in CH$_2$Cl$_2$ (5.00 mL) was added TFA (1.00 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (70 mg, 54%) as a white solid. MS: m/z=638 (M+H$^+$).

Example 66

(3S)-3-(3,5-difluorophenyl)-N-(5-fluoro-4-{2-[(2R,5R)-5-(6-methyl-1H-benzimidazol-2-yl)morpholin-2-yl]ethyl}pyridin-3-yl)-3-(4-fluorophenyl)propanamide

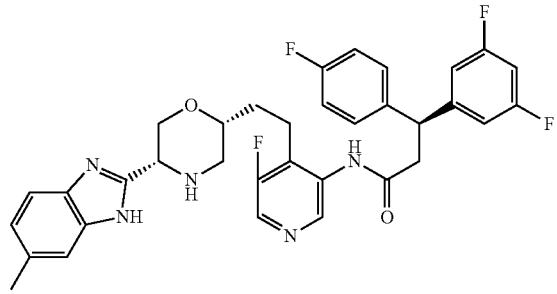 [SMILES: Cc1ccc2nc([C@@H]3CO[C@H](CCc4c(F)cncc4NC(=O)C[C@@H](c4ccc(F)cc4)c4cc(F)cc(F)c4)CN3)[nH]c2c1]

Step 1: (2R,5R)-tert-Butyl 2-(2-(3-((S)-3-(3,5-difluorophenyl)-3-(4-fluorophenyl)propanamido)-5-fluoropyridin-4-yl)ethyl)-5-(6-methyl-1H-benzo[d]imidazol-2-yl)morpholine-4-carboxylate

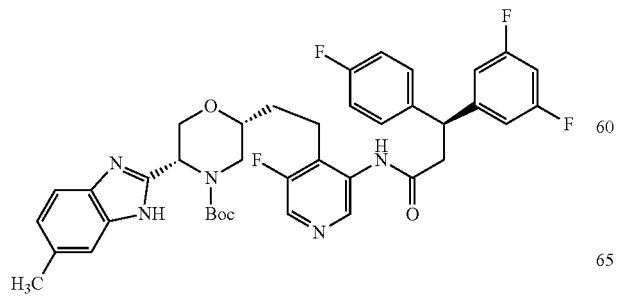

A mixture of 4-methylbenzene-1,2-diamine (22 mg, 0.18 mmol) and Na$_2$S$_2$O$_5$ (38 mg, 0.36 mmol) in DMA (10.0 mL) was heated at 100° C. and solution (2R,5S)-tert-butyl 2-(2-(3-((S)-3-(3,5-difluorophenyl)-3-(4-fluorophenyl)propanamido)-5-fluoropyridin-4-yl)ethyl)-5-formylmorpholine-4-carboxylate (75 mg, 0.12 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extracts were washed with brine (25.0 mL), dried (Na$_2$SO$_4$), filtered and concentrated under reduced pressure. The residue was purified by 24 g SiO$_2$ column using a gradient elution of 0-60% EtOAc in hexanes. Fractions containing product were combined and the solvents were removed in vacuo to provide the product (48 mg, 55%) as colourless gum. MS: m/z=718 (M+H$^+$).

Step 2: (3S)-3-(3,5-difluorophenyl)-N-(5-fluoro-4-{2-[(2R,5R)-5-(6-methyl-1H-benzimidazol-2-yl)morpholin-2-yl]ethyl}pyridin-3-yl)-3-(4-fluorophenyl)propanamide To a solution of (2R,5R)-tert-butyl 2-(2-(3-((S)-3-(3,5-difluorophenyl)-3-(4-fluorophenyl)propanamido)-5-fluoropyridin-4-yl)ethyl)-5-(6-methyl-1H-benzo[d]imidazol-2-yl)morpholine-4-carboxylate (48 mg, 0.06 mmol) in CH$_2$Cl$_2$ (5.00 mL) was added TFA (1.00 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (18 mg, 30%) as a white solid. MS: m/z=618 (M+H$^+$).

Example 67

(3R)-3-(4-chloro-3-fluorophenyl)-N-(4-{2-[(2R,5R)-5-(5,6-dimethyl-1H-benzimidazol-2-yl)morpholin-2-yl]ethyl}-5-fluoropyridin-3-yl)-3-(3-fluorophenyl)propanamide

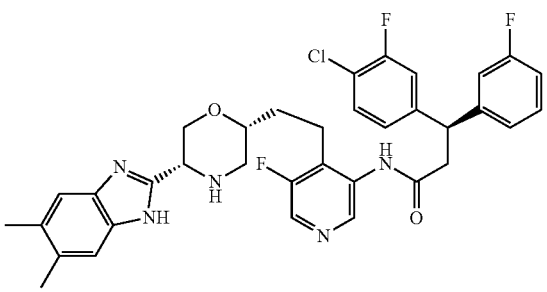 [SMILES: Cc1cc2nc([C@@H]3CO[C@H](CCc4c(F)cncc4NC(=O)C[C@H](c4cccc(F)c4)c4ccc(Cl)c(F)c4)CN3)[nH]c2cc1C]

Step 1: (S,E)-3-(3-(4-Chloro-3-fluorophenyl)acryloyl)-4-phenyloxazolidin-2-one

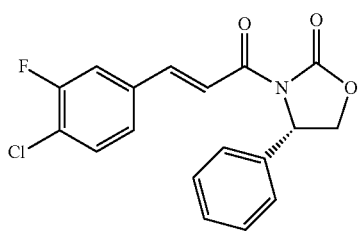 [SMILES: O=C(/C=C/c1ccc(Cl)c(F)c1)N1C(=O)OC[C@@H]1c1ccccc1]

To a stirred solution of (S)-dimethyl (2-oxo-2-(2-oxo-5-phenyloxazolidin-3-yl)ethyl)phosphonate (3.00 g, 9.03 mmol) in THF (20.0 mL) was added potassium tert-butoxide (1.01 mL, 1M in THF, 17.7 mmol) and mixture was stirred at room temperature for 20 min. A solution of 4-chloro-3-fluorobenzaldehyde (1.43 g, 9.03 mmol) was added drop-wise and reaction mixture was stirred at room temperature for 2 h. The reaction mixture was quenched with $H_2O$ (50.0 mL), extracted with EtOAc (2×100 mL). The organic layer was washed with brine (100 mL), dried ($Na_2SO_4$), filtered and concentrated under reduced pressure. The residue was purified by 120 g $SiO_2$ column using a gradient elution of 0-50% EtOAc in hexanes. Fractions containing product were combined and the solvents were removed in vacuo to provide the product (2.17 g, 70%) as a white solid. MS: m/z=346 (M+H$^+$).

Step 2: (S)-3-((R)-3-(4-Chloro-3-fluorophenyl)-3-(3-fluorophenyl)propanoyl)-4-phenyloxazolidin-2-one

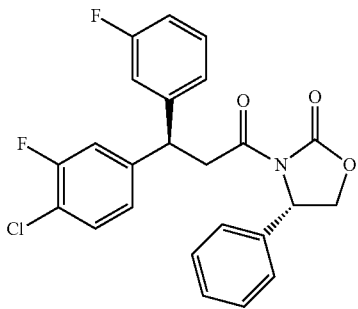 [SMILES: O=C(C[C@H](c1cccc(F)c1)c1ccc(Cl)c(F)c1)N1C(=O)OC[C@@H]1c1ccccc1]

To a suspension of CuBr.Me$_2$S (1.91 g, 9.34 mmol) in THF (20.0 mL) was added dimethyl sulphide (5.00 mL) at −40° C. The reaction mixture was stirred for 5 min and 3-fluorophenylmagnesium bromide (12.4 mL, 1 M in THF, 12.4 mmol) was added drop-wise over a period of 15 min. The reaction mixture was stirred at same temperature for 30 min and then stirred at −20° C. for 20 min. A solution of (S,E)-3-(3-(4-chloro-3-fluorophenyl)acryloyl)-4-phenyloxazolidin-2-one (2.15 g, 6.231 mmol) in THF (10.0 mL) was added drop wise at −20° C. and the reaction mixture was stirred at −20° C. for 4 h. The reaction mixture was quenched with aqueous ammonium chloride solution (25.0 mL) and extracted with EtOAc (2×50.0 mL). The combined organic extracts were washed with brine (100 mL), dried (Na$_2$SO$_4$), filtered and concentrated under reduced pressure. The residue was purified by 120 g SiO$_2$ column using a gradient elution of 0-40% EtOAc in hexanes. Fractions containing product were combined and the solvents were removed in vacuo to provide the product (2.24 g, 81%) as off white solid. MS: m/z=442 (M+H$^+$).

Step 3: (R)-3-(4-Chloro-3-fluorophenyl)-3-(3-fluorophenyl)propanoic acid

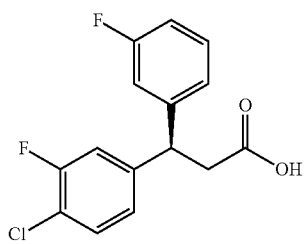 [SMILES: O=C(O)C[C@H](c1cccc(F)c1)c1ccc(Cl)c(F)c1]

To a precooled (0° C.) solution of (S)-3-((R)-3-(4-chloro-3-fluorophenyl)-3-(3-fluorophenyl)propanoyl)-4-phenyloxazolidin-2-one (2.24 g, 5.09 mmol) in THF (15.0 mL) and water (10.0 mL) was added 30% hydrogen peroxide (3.10 mL) drop-wise and stirred for 10 min. A solution of LiOH (0.27 g, 11.2 mmol) in water (2.00 mL) was added at 0° C. and the reaction mixture was stirred at 0° C. for 2 h. The reaction mixture was quenched with saturated solution of sodium sulphite (50.0 mL), water (50.0 mL) and extracted with EtOAc (2×50.0 mL). The aqueous phase was acidified to pH 4 and extracted with EtOAc (2×50.0 mL). The combined EtOAc extracts were washed with brine (100 mL), dried (Na$_2$SO$_4$), filtered and concentrated under reduced pressure to provide product (0.34 g, 68%) as a white solid. MS: m/z=297 (M+H$^+$).

Step 4: (2R,5S)-tert-Butyl 5-(((tert-butyldimethylsilyl)oxy)methyl)-2-(2-(3-((R)-3-(4-chloro-3-fluorophenyl)-3-(3-fluorophenyl)propanamido)-5-fluoropyridin-4-yl))ethyl)ethyl)morpholine-4-carboxylate

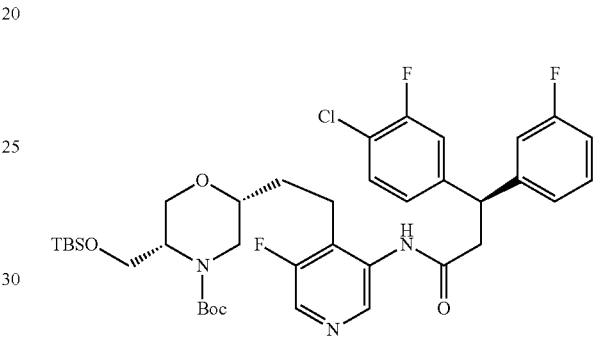

To a stirred solution of (R)-3-(4-chloro-3-fluorophenyl)-3-(3-fluorophenyl)propanoic acid (0.19 g, 0.64 mmol) and (2R,5S)-tert-butyl 2-(2-(3-amino-5-fluoropyridin-4-yl)ethyl)-5-(((tert-butyldimethylsilyl)oxy)methyl)morpholine-4-carboxylate (0.30 g, 0.64 mmol) in pyridine (10.0 mL) at −20° C. was added POCl$_3$ (0.06 mL, 0.70 mmol) drop-wise and the reaction mixture was warmed to 0° C. over a period of 2 h. The reaction mixture was quenched with saturated solution of KH$_2$PO$_4$ (1.00 mL), extracted with EtOAc (3×20.0 mL) and the combined organic extracts were washed with brine (25.0 mL), dried (Na$_2$SO$_4$), filtered and concentrated under reduced pressure. The residue was purified by 40 g SiO$_2$ column using a gradient elution of 0-40% EtOAc in hexanes. Fractions containing product were combined and the solvents were removed in vacuo to provide the product (0.24 g, 50%) as a colourless gum. MS: m/z=748 (M+H$^+$).

Step 5: (2R,5R)-tert-Butyl 2-(2-(3-((R)-3-(4-chloro-3-fluorophenyl)-3-(3-fluorophenyl)propanamido)-5-fluoropyridin-4-yl))ethyl)ethyl)-5-(hydroxymethyl)morpholine-4-carboxylate

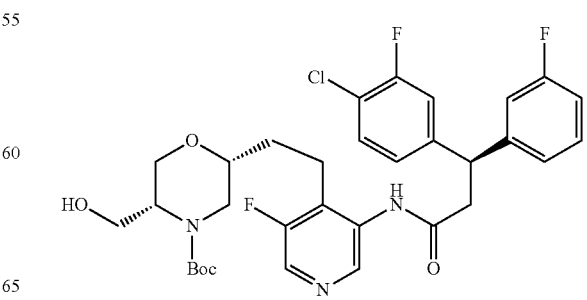

To a solution (2R,5S)-tert-butyl 5-(((tert-butyldimethyl-silyl)oxy)methyl)-2-(2-(3-((R)-3-(4-chloro-3-fluorophenyl)-3-(3-fluorophenyl)propanamido)-5-fluoropyridin-4-yl))ethyl)ethyl)morpholine-4-carboxylate (0.24 g, 0.32 mmol) in THF (5.00 mL) was added TBAF (0.48 mL, 1.0 M in THF, 0.48 mmol) and the mixture was stirred at room temperature for 1 h. The solvent was removed under reduced pressure. The residue was purified by 24 g SiO$_2$ column using a gradient elution of 0-100% EtOAc in hexanes. Fractions containing product were combined and the solvents were removed in vacuo to provide the product (0.19 g, 93%) as a colourless gum. MS: m/z=634 (M+H$^+$).

Step 6: (2R,5R)-tert-Butyl 2-(2-(3-((R)-3-(4-chloro-3-fluorophenyl)-3-(3-fluorophenyl)propanamido)-5-fluoropyridin-4-yl))ethyl)ethyl)-5-formylmorpholine-4-carboxylate

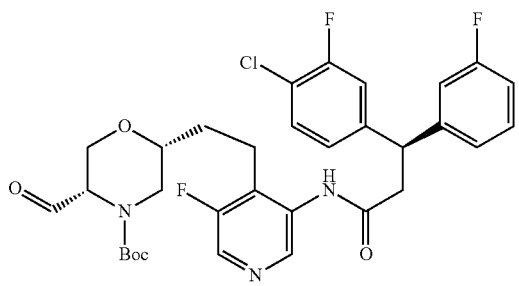 [SMILES: CC(C)(C)OC(=O)N1C[C@@H](CCc2c(F)cncc2NC(=O)C[C@H](c2cccc(F)c2)c2ccc(Cl)c(F)c2)OC[C@H]1C=O]

To a solution of (2R,5R)-tert-butyl 2-(2-(3-((R)-3-(4-chloro-3-fluorophenyl)-3-(3-fluorophenyl)propanamido)-5-fluoropyridin-4-yl)ethyl)ethyl)-5-(hydroxymethyl)morpholine-4-carboxylate (0.19 g, 0.30 mmol) in CH$_2$Cl$_2$ (10.0 mL) was added Dess-Martin periodinane (0.19 g, 0.45 mmol) and the mixture was stirred at 0° C. for 2 h. The reaction mixture was diluted with CH$_2$Cl$_2$ (30.0 mL) and quenched with saturated solution of Na$_2$S$_2$O$_3$ (10.0 mL) and NaHCO$_3$ solution (10.0 mL). The organic layer was separated washed with brine (25.0 mL), dried (Na$_2$SO$_4$), filtered and concentrated under reduced pressure to provide product (0.18 g, crude) as yellow gum. The crude product was directly used in the next step without purification. MS: m/z=632 (M+H$^+$).

Step 7: (2R,5R)-tert-Butyl 2-(2-(3-((R)-3-(4-chloro-3-fluorophenyl)-3-(3-fluorophenyl)propanamido)-5-fluoropyridin-4-yl)ethyl)ethyl)-5-(5,6-dimethyl-1H-benzo[d]imidazol-2-yl)morpholin-4-carboxylate

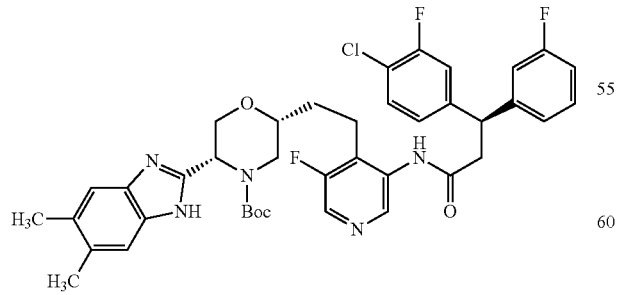

A mixture of 4,5-dimethylbenzene-1,2-diamine (35.4 mg, 0.26 mmol) and Na$_2$S$_2$O$_5$ (81.0 mg, 0.78 mmol) in DMA (10.0 mL) was heated at 100° C. and a solution of (2R,5R)-tert-butyl 2-(2-(3-((R)-3-(4-chloro-3-fluorophenyl)-3-(3-fluorophenyl)propanamido)-5-fluoropyridin-4-yl))ethyl)ethyl)-5-formylmorpholine-4-carboxylate (0.16 g, 0.26 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extract were washed with brine (25.0 mL), dried (Na$_2$SO$_4$), filtered and concentrated under reduced pressure. The residue was purified by 24 g SiO$_2$ column using a gradient elution of 0-60% EtOAc in hexanes. Fractions containing product were combined and the solvents were removed in vacuo to provide the product (45.0 mg, 23%) as off white solid.
MS: m/z=748 (M+H$^+$).

Step 8: (3R)-3-(4-chloro-3-fluorophenyl)-N-(4-{2-[(2R,5R)-5-(5,6-dimethyl-1H-benzimidazol-2-yl)morpholin-2-yl]ethyl}-5-fluoropyridin-3-yl)-3-(3-fluorophenyl)propanamide To a solution of (2R,5R)-tert-butyl 2-(2-(3-((R)-3-(4-chloro-3-fluorophenyl)-3-(3-fluorophenyl)propanamido)-5-fluoropyridin-4-yl)ethyl)-5-(5,6-dimethyl-1H-benzo[d]imidazol-2-yl)morpholin-4-carboxylate (45.0 mg, 0.06 mmol) in CH$_2$Cl$_2$ (1.00 mL) was added TFA (0.30 mL) and mixture was stirred at room temperature for 2 h. The solvent was removed under reduced pressure. The residue was purified by 24 g C18 column using a gradient elution of 10-80% acetonitrile in water. Fractions containing product were combined and the solvents were removed in vacuo and lyophilized to provide the product (25.0 mg, 47%) as a white solid. MS: m/z=648 (M+H$^+$).

Example 68

(3S)-3-(4-chloro-3-fluorophenyl)-N-(4-{2-[(2R,5R)-5-(5,6-dimethyl-1H-benzimidazol-2-yl)morpholin-2-yl]ethyl}-5-fluoropyridin-3-yl)-3-(5-fluoropyridin-3-yl)propanamide

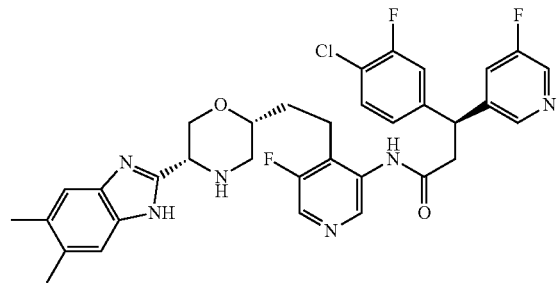 [SMILES: Cc1cc2nc([C@@H]3CO[C@H](CCc4c(F)cncc4NC(=O)C[C@H](c4cncc(F)c4)c4ccc(Cl)c(F)c4)CN3)[nH]c2cc1C]

Step 1: (R,E)-3-(3-(5-Fluoropyridin-3-yl)acryloyl)-4-phenyloxazolidin-2-one

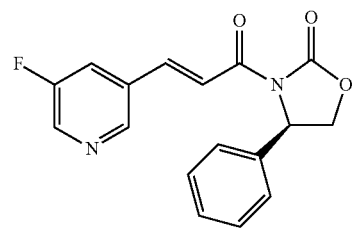 [SMILES: O=C(/C=C/c1cncc(F)c1)N1C(=O)OC[C@H]1c1ccccc1]

To a stirred solution of (R)-dimethyl (2-oxo-2-(2-oxo-5-phenyloxazolidin-3-yl)ethyl)phosphonate (43.5 g, 132 mmol) in THF (100 mL) was added potassium tert-butoxide (132 mL, 1M in THF, 132 mmol) and mixture was stirred at room temperature for 20 min. A solution of 3-fluoroisonicotinaldehyde (15.0 g, 120 mmol) in THF (30.0 mL) was added drop-wise and reaction mixture was stirred at room temperature for 2 h. The reaction mixture was quenched with $H_2O$ (75.0 mL), extracted with EtOAc (2×300 mL). The organic layer was washed with brine (300 mL), dried ($Na_2SO_4$), filtered and concentrated under reduced pressure. The residue was purified by 40 g $SiO_2$ column using a gradient elution of 0-50% EtOAc in hexanes. Fractions containing product were combined and the solvents were removed in vacuo to provide the product (32.5 g, 87%) as a white solid.

Step 2: (R)-3-((S)-3-(4-Chloro-3-fluorophenyl)-3-(5-fluoropyridin-3-yl)propanoyl)-4-phenyloxazolidin-2-one

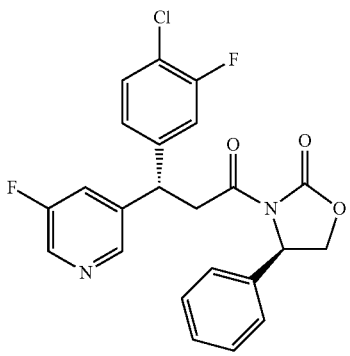 [SMILES: O=C(C[C@H](c1cncc(F)c1)c1ccc(Cl)c(F)c1)N1C(=O)OC[C@H]1c1ccccc1]

To a suspension of $CuBr.Me_2S$ (10.3 g, 47.92 mmol) in THF (100 mL) was added dimethyl sulphide (48.0 mL) at −40° C. The reaction mixture was stirred for 5 min and 4-chloro-3-fluorophenylmagnesium bromide (47.9 mL, 1M in THF, 47.9 mmol) was added dropwise over a period of 15 min. The reaction mixture was stirred at same temperature for 30 min and then stirred at −20° C. for 20 min. A solution (R,E)-3-(3-(5-fluoropyridin-3-yl)acryloyl)-4-phenyloxazolidin-2-one (10.0 g, 31.95 mmol) in THF (50.0 mL) was added drop-wise at −20° C. and the reaction mixture was stirred at −20° C. for 4 h. The reaction mixture was quenched with aqueous ammonium chloride solution (100 mL) and extracted with EtOAc (2×250 mL). The combined organic extracts were washed with brine (200 mL), dried ($Na_2SO_4$), filtered and concentrated under to provide the product (16.0 g, crude) as light yellow gum. The crude product was directly used in the next step without purification.

Step 3: (S)-3-(4-Chloro-fluorophenyl)-3-(5-fluoropyridin-3-yl)propanoic acid

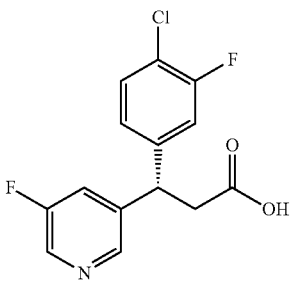 [SMILES: O=C(O)C[C@H](c1cncc(F)c1)c1ccc(Cl)c(F)c1]

To a precooled (0° C.) solution of (R)-3-((S)-3-(4-chloro-3-fluorophenyl)-3-(5-fluoropyridin-3-yl)propanoyl)-4-phenyloxazolidin-2-one (16.0 g, 36.2 mmol) in THF (80.0 mL) and water (40.0 mL) was added 30% hydrogen peroxide (26.0 mL) drop-wise and stirred for 10 min. A solution of LiOH (1.90 g, 79.6 mmol) in water (15.0 mL) was added at 0° C. and reaction mixture was stirred at 0° C. for 2 h. The reaction mixture was quenched with saturated solution of sodium sulphite (200 mL), water (200 mL) and extracted with EtOAc (2×100 mL). The aqueous phase was acidified to pH 4 and extracted with EtOAc (2×200 mL). The combined organic extracts were washed with brine (100 mL), dried ($Na_2SO_4$), filtered and concentrated under reduced pressure to provide product (6.80 g, 63%) as an off white solid.

Step 4: (2R,5S)-tert-Butyl 2-((3-Amino-5-fluoropyridin-4-yl)ethynyl)-5-(((tert-butyldimethylsilyl)oxy)methyl)morpholine-4-carboxylate

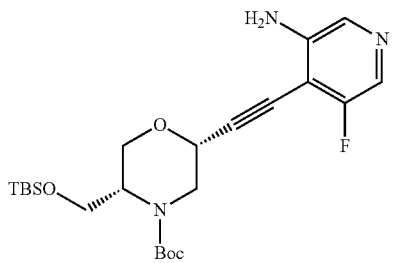 [SMILES: CC(C)(C)OC(=O)N1C[C@@H](C#Cc2c(N)cncc2F)OC[C@H]1CO[Si](C)(C)C(C)(C)C]

To a stirred solution of 5-fluoro-4-iodopyridin-3-amine (0.74 g, 3.09 mmol) and (2R,5S)-tert-butyl 5-(((tert-butyldimethylsilyl)oxy)methyl)-2-ethynylmorpholine-4-carboxylate (1.00 g, 2.81 mmol) in acetonitrile (15.0 mL) and the mixture was degassed with Argon for 10 min. Added CuI (54 mg, 0.28 mmol), $PdCl_2(PPh_3)_2$ (0.14 g, 0.196 mmol) and the mixture was stirred at 70° C. for 6 h. The solvent was removed under reduced pressure and water (25.0 mL) was added to the residue. The mixture was extracted with EtOAc (3×50.0 mL) and combined organic extracts were washed with brine (25.0 mL), dried ($Na_2SO_4$), filtered and concentrated under reduced pressure. The residue was purified by 40 g $SiO_2$ column using a gradient elution of 0-30% EtOAc in hexanes. Fractions containing product were combined and the solvents were removed in vacuo to provide the product (0.90 g, 69%) as a colourless gum. MS: m/z=466 (M+H$^+$).

Step 5: (2R,5S)-tert-Butyl 2-(2-(3-amino-5-fluoropyridin-4-yl)ethyl)-5-(((tert-butyldimethylsilyl)oxy)methyl)morpholine-4-carboxylate

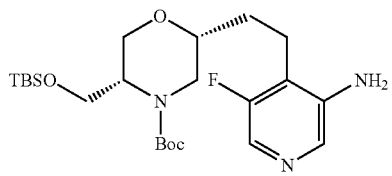 [SMILES: CC(C)(C)OC(=O)N1C[C@@H](CCc2c(N)cncc2F)OC[C@H]1CO[Si](C)(C)C(C)(C)C]

To a solution of (2R,5S)-tert-butyl 2-((3-amino-5-fluoropyridin-4-yl)ethynyl)-5-(((tert-butyldimethylsilyl)oxy)methyl)morpholine-4-carboxylate (0.90 g, 1.94 mmol) in EtOH (20.0 mL) was added Pd(OH)₂ (90.0 mg, 20% by wt) and the mixture was stirred under H₂ atmosphere for 3 h at 1 atm. The mixture was filtered over pad of celite. The celite bed was washed with EtOAc (2×25.0 mL). The combined organic extract were washed with brine (25.0 mL), dried (Na₂SO₄), filtered and concentrated under reduced pressure to provide product (0.90 g, crude) as yellow gum. The crude product was directly used in the next step without purification. MS: m/z=470 (M+H⁺).

Step 6: (2R,5S)-tert-Butyl 5-(((tert-butyldimethylsilyl)oxy)methyl)-2-(2-(3-((S)-3-(4-chloro-3-fluorophenyl)-3-(5-fluoropyridin-3-yl)propanamido)-5-fluoropyridin-4-yl)ethyl)morpholine-4-carboxylate

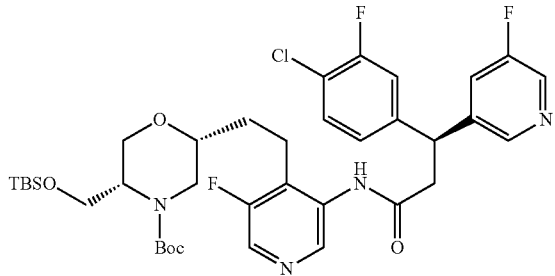 [SMILES: CC(C)(C)OC(=O)N1C[C@@H](CCc2c(F)cncc2NC(=O)C[C@H](c2cncc(F)c2)c2ccc(Cl)c(F)c2)OC[C@H]1CO[Si](C)(C)C(C)(C)C]

To a stirred solution of (S)-3-(4-chloro-fluorophenyl)-3-(5-fluoropyridin-3-yl)propanoic acid (0.19 g, 0.64 mmol) and (2R,5S)-tert-butyl 2-(2-(3-amino-5-fluoropyridin-4-yl)ethyl)-5-(((tert-butyldimethylsilyl)oxy)methyl)morpholine-4-carboxylate (0.30 g, 0.64 mmol) in pyridine (10.0 mL) at −20° C. was added POCl₃ (0.06 mL, 0.70 mmol) dropwise and reaction mixture was warmed to 0° C. over a period of 2 h. The reaction mixture was quenched with saturated solution of KH₂PO₄ (1.00 mL) and extracted with EtOAc (3×20.0 mL). The combined organic extracts were washed with brine (25.0 mL), dried (Na₂SO₄), filtered and concentrated under reduced pressure. The residue was purified by 40 g SiO₂ column using a gradient elution of 0-40% EtOAc in hexanes. Fractions containing product were combined and the solvents were removed in vacuo to provide the product (0.23 g, 48%) as a colourless gum.
MS: m/z=750 (M+H⁺).

Step 7: (2R,5S)-tert-Butyl 2-(2-(3-((S)-3-(4-chloro-3-fluorophenyl)-3-(5-fluoropyridin-3-yl)propanamido)-5-fluoropyridin-4-yl)ethyl)-5-(hydroxymethyl)morpholine-4-carboxylate

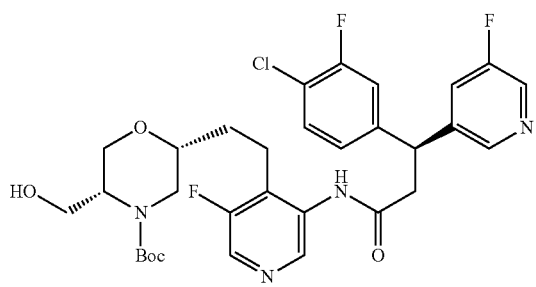 [SMILES: CC(C)(C)OC(=O)N1C[C@@H](CCc2c(F)cncc2NC(=O)C[C@H](c2cncc(F)c2)c2ccc(Cl)c(F)c2)OC[C@H]1CO]

To a solution of (2R,5S)-tert-butyl 5-(((tert-butyldimethylsilyl)oxy)methyl)-2-(2-(3-((S)-3-(4-chloro-3-fluorophenyl)-3-(5-fluoropyridin-3-yl)propanamido)-5-fluoropyridin-4-yl)ethyl)morpholine-4-carboxylate (0.23 g, 0.31 mmol) in THF (5.00 mL) was added TBAF (0.46 mL, 1.0 M in THF, 0.46 mmol) and the mixture was stirred at room temperature for 1 h. The solvent was removed under reduced pressure. The residue was purified by 24 g SiO₂ column using a gradient elution of 0-100% EtOAc in hexanes. Fractions containing product were combined and the solvents were removed in vacuo to provide the product (0.17 g, 87%) as a colourless gum. MS: m/z=636 (M+H⁺).

Step 8: (2R,5S)-tert-Butyl 2-(2-(3-((S)-3-(4-chloro-3-fluorophenyl)-3-(5-fluoropyridin-3-yl)propanamido)-5-fluoropyridin-4-yl)ethyl)-5-formylmorpholine-4-carboxylate

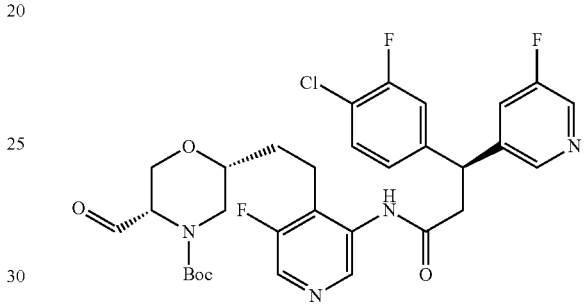

To a solution of (2R,5S)-tert-butyl 2-(2-(3-((S)-3-(4-chloro-3-fluorophenyl)-3-(5-fluoropyridin-3-yl)propanamido)-5-fluoropyridin-4-yl)ethyl)-5-(hydroxymethyl)morpholine-4-carboxylate (0.17 g, 0.26 mmol) in CH₂Cl₂ (10.0 mL) was added Dess-Martin periodinane (0.17 g, 0.40 mmol) and mixture was stirred at 0° C. for 2 h. The reaction mixture was diluted with CH₂Cl₂ (25.0 mL) and quenched with saturated solution of Na₂S₂O₃ (10.0 mL) and NaHCO₃ solution (10.0 mL). The organic layer was separated washed with brine (25.0 mL), dried (Na₂SO₄), filtered and concentrated under reduced pressure to provide product (0.17 g, crude) as yellow gum. The crude product was directly used in the next step without purification. MS: m/z=634 (M+H⁺).

Step 9: (2R,5S)-tert-Butyl 2-(2-(3-((S)-3-(4-chloro-3-fluorophenyl)-3-(5-fluoropyridin-3-yl)propanamido)-5-fluoropyridin-4-yl)ethyl)-5-(5,6-dimethyl-1H-benzo[d]imidazol-2-yl)morpholin-4-carboxylate

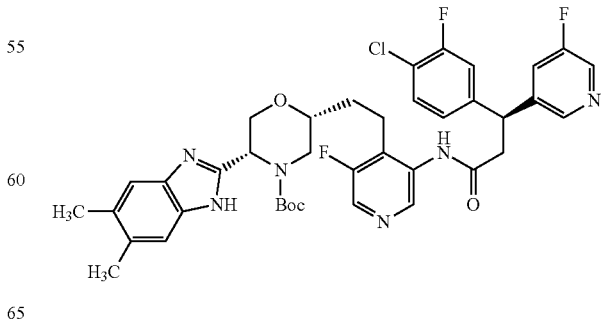

A mixture of 4,5-dimethylbenzene-1,2-diamine (55.0 mg, 0.40 mmol) and Na₂S₂O₅ (84.0 mg, 0.81 mmol) in DMA (10.0 mL) was heated at 100° C. and solution (2R,5S)-tert-butyl 2-(2-(3-((S)-3-(4-chloro-3-fluorophenyl)-3-(5-fluoropyridin-3-yl)propanamido)-5-fluoropyridin-4-yl)ethyl)-5-formylmorpholine-4-carboxylate (0.17 g, 0.27 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extracts were washed with brine (25.0 mL), dried (Na$_2$SO$_4$), filtered and concentrated under reduced pressure. The residue was purified by 4 g SiO$_2$ column using a gradient elution of 0-60% EtOAc in hexanes. Fractions containing product were combined and the solvents were removed in vacuo to provide the product (20.0 mg, 10%) as off white solid. MS: m/z=750 (M+H$^+$).

Step 10: (3S)-3-(4-chloro-3-fluorophenyl)-N-(4-{2-[(2R,5R)-5-(5,6-dimethyl-1H-benzimidazol-2-yl)morpholin-2-yl]ethyl}-5-fluoropyridin-3-yl)-3-(5-fluoropyridin-3-yl)propanamide To a solution of (2R,5S)-tert-butyl 2-(2-(3-((S)-3-(4-chloro-3-fluorophenyl)-3-(5-fluoropyridin-3-yl)propanamido)-5-fluoropyridin-4-yl)ethyl)-5-(5,6-dimethyl-1H-benzo[d]imidazol-2-yl)morpholin-4-carboxylate (20.0 mg, 0.03 mmol) in CH$_2$Cl$_2$ (1.00 mL) was added TFA (0.20 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (18.0 mg, 77%) as a white solid. MS: m/z=650 (M+H$^+$).

Example 69

(3R)—N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)-3-phenylpropanamide

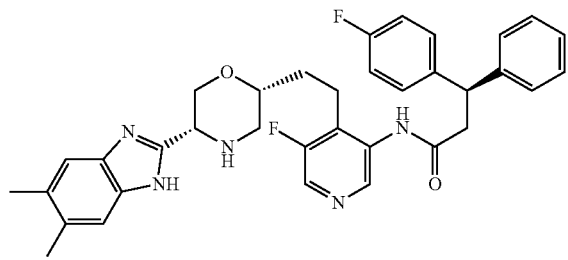 [SMILES: Cc1cc2nc([C@@H]3CO[C@H](CCc4c(F)cncc4NC(=O)C[C@H](c4ccccc4)c4ccc(F)cc4)CN3)[nH]c2cc1C]

Step 1: (2R,5R)-tert-Butyl 5-(5,6-dimethyl-1H-benzo[d]imidazol-2-yl)-2-(2-(3-fluoro-5-((R)-3-(4-fluorophenyl)-3-phenylpropanamido)pyridin-4-yl)ethyl)morpholine-4-carboxylate

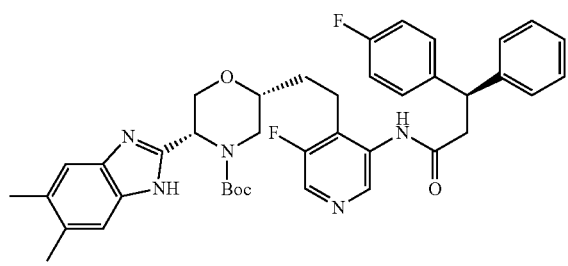 [SMILES: Cc1cc2nc([C@@H]3CO[C@H](CCc4c(F)cncc4NC(=O)C[C@H](c4ccccc4)c4ccc(F)cc4)CN3C(=O)OC(C)(C)C)[nH]c2cc1C]

A mixture of 4,5-dimethylbenzene-1,2-diamine (32.0 mg, 0.24 mmol) and Na$_2$S$_2$O$_5$ (50.0 mg, 0.48 mmol) in DMA (5.00 mL) was heated at 100° C. and a solution of (2R,5S)-tert-butyl-2-(2-(3-fluoro-5-((R)-3-(4-fluorophenyl)-3-phenylpropanamido)pyridin-4-yl)ethyl)-5-formylmorpholine-4-carboxylate (95.0 mg, 0.16 mol) in DMA (2.00 mL) was added drop-wise. The reaction mixture was stirred at 100° C. for 1 h. The mixture was cooled to room temperature, poured in water (10.0 mL) and extracted with EtOAc (3×25.0 mL). The combined organic extracts were washed with brine (25.0 mL), dried (Na$_2$SO$_4$), filtered and concentrated under reduced pressure. The residue was purified by 4 g SiO$_2$ column using a gradient elution of 0-60% EtOAc in hexanes. Fractions containing product were combined and the solvents were removed in vacuo to provide the product (22.0 mg, 19% over two steps) as colourless gum. MS: m/z=696 (M+H$^+$).

Step 2: (3R)—N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)-3-phenylpropanamide To a solution (2R,5R)-tert-butyl 5-(5,6-dimethyl-1H-benzo[d]imidazol-2-yl)-2-(2-(3-fluoro-5-((R)-3-(4-fluorophenyl)-3-phenylpropanamido)pyridin-4-yl)ethyl)morpholine-4-carboxylate (50.0 mg, 0.07 mmol) in CH$_2$Cl$_2$ (2.00 mL) was added TFA (1.00 mL) and the mixture was stirred at room temperature for 2 h. The solvent was removed under reduced pressure. The residue was purified by 24 g C18 column using a gradient elution of 10-50% acetonitrile in water. Fractions containing product were combined and the solvents were removed in vacuo and lyophilized to provide the product (12.0 mg, 20%) as a white solid. MS: m/z=596 (M+H$^+$).

Example 70

(3R)—N-(4-{2-[(2R,5R)-5-(5,6-difluoro-1H-benzimidazol-2-yl)morpholin-2-yl]ethyl}-5-fluoropyridin-3-yl)-3-(4-fluorophenyl)-3-phenylpropanamide

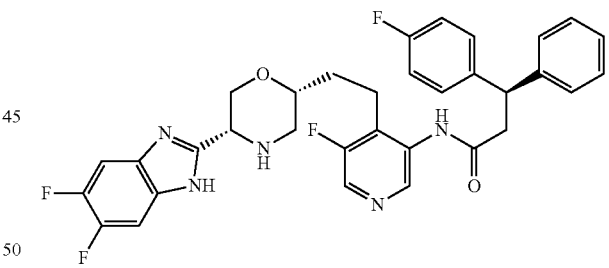

Step 1: (R,E)-3-(3-(4-Fluorophenyl)acryloyl)-4-phenyloxazolidin-2-one

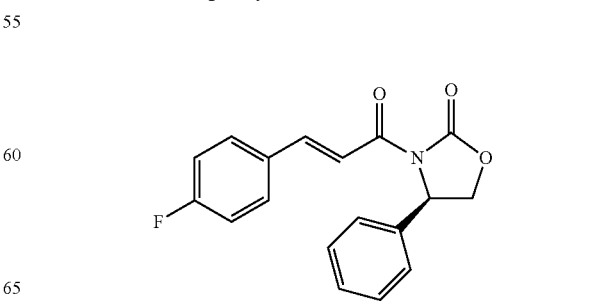

To a stirred solution of (R)-dimethyl (2-oxo-2-(2-oxo-5-phenyloxazolidin-3-yl)ethyl)phosphonate (5.86 g, 17.7 mmol), prepared as described in Example 64, in THF (100 mL) was added potassium tert-butoxide (17.7 mL, 1M in THF, 17.7 mmol) and mixture was stirred at room temperature for 20 min. A solution of 4-fluorobenzaldehyde (2.00 g, 16.1 mmol) in THF (10.0 mL) was added dropwise and reaction mixture was stirred at room temperature for 2 h. The reaction mixture was quenched with H$_2$O (10.0 mL), extracted with EtOAc (2×100 mL). The combined organic extracts were washed with brine (100 mL), dried (Na$_2$SO$_4$), filtered and concentrated under reduced pressure. The residue was purified by 120 g SiO$_2$ column using a gradient elution of 0-50% EtOAc in hexanes. Fractions containing product were combined and the solvents were removed in vacuo to provide the product (3.30 g, 56%) as a white solid. MS: m/z=312 (M+H$^+$).

Step 2: (R)-3-((S)-3-(4-Fluorophenyl)-3-phenylpropanoyl)-4-phenyloxazolidin-2-one

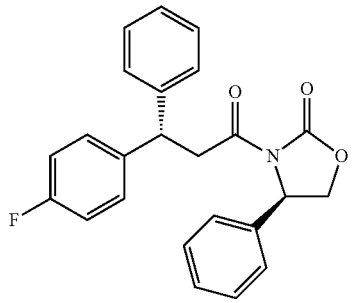 [SMILES: O=C(C[C@@H](c1ccccc1)c1ccc(F)cc1)N1C(=O)OC[C@H]1c1ccccc1]

To a suspension of CuBr.Me$_2$S (1.98 g, 9.64 mmol) in THF (50.0 mL) was added dimethyl sulphide (10.0 mL) at −40° C. The reaction mixture was stirred for 5 min and phenylmagnesium bromide (19.2 mL, 1M in THF, 19.2 mmol) was added drop-wise over a period of 15 min. The reaction mixture was stirred at same temperature for 30 min and then stirred at −20° C. for 20 min. A solution of (R,E)-3-(3-(4-fluorophenyl)acryloyl)-4-phenyloxazolidin-2-one (2.00 g, 6.43 mmol) in THF (10.0 mL) was added drop-wise at −20° C. and reaction mixture was stirred at −20° C. for 4 h. The reaction mixture was quenched with aqueous ammonium chloride solution and extracted with EtOAc (2×50.0 mL). The combined organic extracts were washed with brine (100 mL), dried (Na$_2$SO$_4$), filtered and concentrated under reduced pressure. The residue was purified by 120 g SiO$_2$ column using a gradient elution of 0-40% EtOAc in hexanes. Fractions containing product were combined and the solvents were removed in vacuo to provide the product (1.40 g, 56%) as an off white solid. MS: m/z=390 (M+H$^+$).

Step 3: (S)-3-(4-Fluorophenyl)-3-phenylpropanoic acid

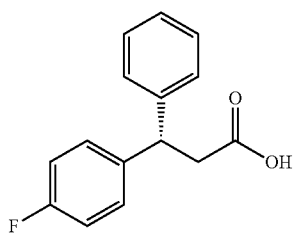 [SMILES: O=C(O)C[C@@H](c1ccccc1)c1ccc(F)cc1]

To a precooled (0° C.) solution of (R)-3-((S)-3-(4-fluorophenyl)-β-phenylpropanoyl)-4-phenyloxazolidin-2-one (0.80 g, 2.05 mmol) in THF (15.0 mL) and water (5.00 mL) was added 30% hydrogen peroxide (1.30 mL) drop-wise and stirred for 10 min. A solution of LiOH (73 mg, 3.0 mmol) in water (2.00 mL) was added at 0° C. and the reaction mixture was stirred at 0° C. for 2 h. The reaction mixture was quenched with saturated solution of sodium sulphite (25.0 mL), water (25.0 mL) and extracted with EtOAc (2×50.0 mL). The aqueous phase was acidified to pH 4 and extracted with EtOAc (2×50.0 mL). The combined organic extracts were washed with brine (50.0 mL), dried (Na$_2$SO$_4$), filtered and concentrated under reduced pressure to provide product (0.34 g, 68%) as a white solid. MS: m/z=245 (M+H$^+$).

Step 4: (2R,5S)-tert-Butyl 5-(((tert-butyldimethylsilyl)oxy)methyl)-2-(2-(3-fluoro-5-((R)-3-(4-fluorophenyl)-3-phenylpropanamido)pyridin-4-yl)ethyl)morpholine-4-carboxylate

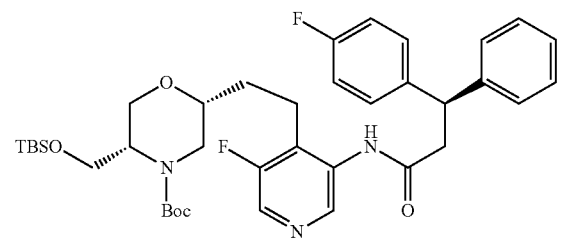 [SMILES: CC(C)(C)OC(=O)N1C[C@@H](CCc2c(F)cncc2NC(=O)C[C@H](c2ccccc2)c2ccc(F)cc2)OC[C@H]1CO[Si](C)(C)C(C)(C)C]

To a stirred solution of (S)-3-(4-fluorophenyl)-3-phenylpropanoic acid (0.34 g, 1.39 mmol) and (2R,5S)-tert-butyl 2-(2-(3-amino-5-fluoropyridin-4-yl)ethyl)-5-(((tert-butyldimethylsilyl)oxy)methyl)morpholine-4-carboxylate (0.64 g, 1.39 mmol) in pyridine (10.0 mL) at −20° C. was added POCl$_3$ (0.15 mL, 1.59 mmol) dropwise and reaction mixture was warmed to 0° C. over a period of 2 h. The reaction mixture was quenched with saturated aqueous solution of KH$_2$PO$_4$ (1.00 mL), extracted with EtOAc (3×20.0 mL). The combined organic extract were washed with brine (25.0 mL), dried (Na$_2$SO$_4$), filtered and concentrated under reduced pressure. The residue was purified by 40 g SiO$_2$ column using a gradient elution of 0-40% EtOAc in hexanes. Fractions containing product were combined and the solvents were removed in vacuo to provide the product (0.70 g, 72%) as a colourless gum. MS: m/z=696 (M+H$^+$).

Step 5: (2R,5R)-tert-Butyl 2-(2-(3-fluoro-5-((S)-3-(4-fluorophenyl)-3-(3-fluoropyridin-4-yl)propanamido)pyridin-4-yl)ethyl)-5-(hydroxymethyl)morpholine-4-carboxylate

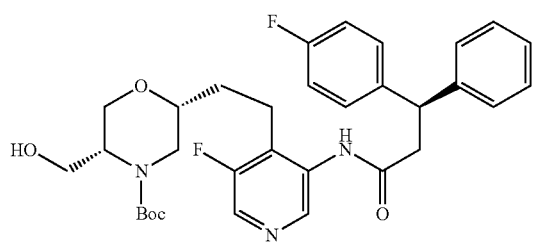 [SMILES: CC(C)(C)OC(=O)N1C[C@@H](CCc2c(F)cncc2NC(=O)C[C@H](c2ccccc2)c2ccc(F)cc2)OC[C@H]1CO]

To a solution of (2R,5S)-tert-butyl 5-(((tert-butyldimethylsilyl)oxy)methyl)-2-(2-(3-fluoro-5-((R)-3-(4-fluorophenyl)-3-phenylpropanamido)pyridin-4-yl)ethyl)morpholine-4-carboxylate (0.70 g, 1.00 mmol) in THF (10.0 mL) was added TBAF (1.51 mL, 1.00 M in THF, 1.51 mmol) and mixture was stirred at room temperature for 1 h. The solvent was removed under reduced pressure. The residue was purified by 24 g SiO₂ column using a gradient elution of 0-60% EtOAc in hexanes. Fractions containing product were combined and the solvents were removed in vacuo to provide the product (0.56 g, 95%) as a colourless gum. MS: m/z=582 (M+H⁺).

Step 6: (2R,5S)-tert-Butyl 2-(2-(3-fluoro-5-((R)-3-(4-fluorophenyl)-3-phenylpropanamido)pyridin-4-yl)ethyl)-5-formylmorpholine-4-carboxylate

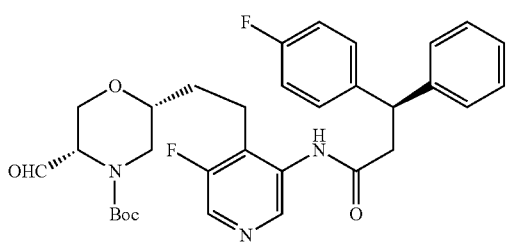

To a solution of (2R,5R)-tert-butyl 2-(2-(3-fluoro-5-((S)-3-(4-fluorophenyl)-3-(3-fluoropyridin-4-yl)propanamido)pyridin-4-yl)ethyl)-5-(hydroxymethyl)morpholine-4-carboxylate (0.50 g, 0.86 mmol) in CH₂Cl₂ (20.0 mL) was added Dess-Martin periodinane (0.55 g, 1.29 mmol) and mixture was stirred at 0° C. for 2 h. The reaction mixture was diluted with CH₂Cl₂ (20.0 mL) and quenched with saturated solution of Na₂S₂O₃ (15.0 mL) and NaHCO₃ solution (15.0 mL). The organic layer was separated and washed with brine (25.0 mL), dried (Na₂SO₄), filtered and concentrated under reduced pressure to provide product (0.50 g, crude) as yellow gum. The crude product was directly used in the next step without purification. MS: m/z=580 (M+H⁺).

Step 7: (2R,5R)-tert-Butyl 5-(5,6-Difluoro-1H-benzo[d]imidazol-2-yl)-2-(2-(3-fluoro-5-((R)-3-(4-fluorophenyl)-3-phenylpropanamido)pyridin-4-yl)ethyl)morpholine-4-carboxylate

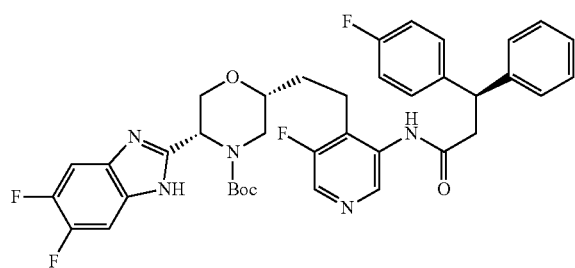 [SMILES: CC(C)(C)OC(=O)N1C[C@@H](CCc2c(F)cncc2NC(=O)C[C@H](c2ccccc2)c2ccc(F)cc2)OC[C@H]1c1nc2cc(F)c(F)cc2[nH]1]

A mixture of 4,5-difluorobenzene-1,2-diamine (67.1 mg, 0.46 mmol) and Na₂S₂O₅ (96.7 mg, 0.93 mmol) in DMA (7.00 mL) was heated at 100° C. and solution of (2R,5S)-tert-butyl 2-(2-(3-fluoro-5-((R)-3-(4-fluorophenyl)-3-phenylpropanamido)pyridin-4-yl)ethyl)-5-formylmorpholine-4-carboxylate (0.18 g, 0.31 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extract were washed with brine (25.0 mL), dried (Na₂SO₄), filtered and concentrated under reduced pressure. The residue was purified by 24 g SiO₂ column using a gradient elution of 0-60% EtOAc in hexanes. Fractions containing product were combined and the solvents were removed in vacuo to provide the product (50.0 mg, 23% over two steps) as colourless gum. MS: m/z=704 (M+H⁺).

Step 8: (3R)—N-(4-{2-[(2R,5R)-5-(5,6-difluoro-1H-benzimidazol-2-yl)morpholin-2-yl]ethyl}-5-fluoropyridin-3-yl)-3-(4-fluorophenyl)-3-phenylpropanamide To a solution of (2R,5R)-tert-butyl 5-(5,6-difluoro-1H-benzo[d]imidazol-2-yl)-2-(2-(3-fluoro-5-((R)-3-(4-fluorophenyl)-3-phenylpropanamido)pyridin-4-yl)ethyl)morpholine-4-carboxylate (50.0 mg, 0.071 mmol) in CH₂Cl₂ (2.00 mL) was added TFA (1.00 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (25.0 mg, 40%) as a white solid. MS: m/z=604 (M+H⁺).

Example 71

(3R)—N-(4-{2-[(2R,5R)-5-(1H-benzimidazol-2-yl)morpholin-2-yl]ethyl}-5-fluoropyridin-3-yl)-3-(4-fluorophenyl)-3-phenylpropanamide

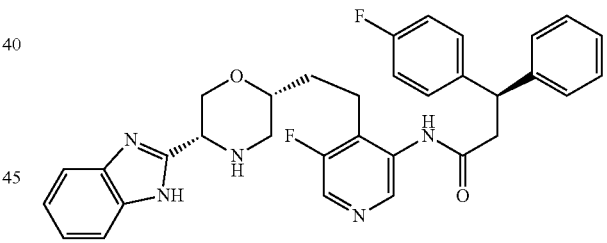

Step 1: (2R,5R)-tert-Butyl 5-(1H-Benzo[d]imidazol-2-yl)-2-(2-(3-fluoro-5-((R)-3-(4-fluorophenyl)-3-phenylpropanamido)pyridin-4-yl)ethyl)morpholine-4-carboxylate

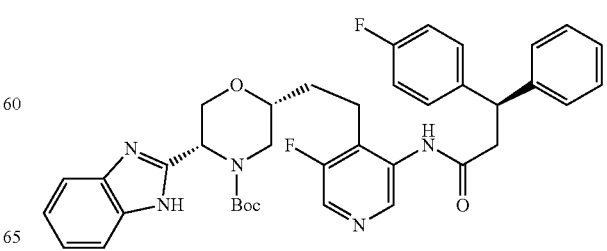

A mixture of benzene-1,2-diamine (55.0 mg, 0.51 mmol) and Na$_2$S$_2$O$_5$ (0.10 g, 1.02 mmol) in DMA (5.00 mL) was heated at 100° C. and a solution of (2R,5S)-tert-butyl 2-(2-(3-fluoro-5-((R)-3-(4-fluorophenyl)-3-phenylpropanamido)pyridin-4-yl)ethyl)-5-formylmorpholine-4-carboxylate (0.20 g, 0.34 mol) in DMA (2.00 mL) was added dropwise. The reaction mixture was stirred at 100° C. for 1 h. The mixture was cooled to room temperature, poured in water (10.0 mL) and extracted with EtOAc (3×25.0 mL). The combined organic extracts were washed with brine (25.0 mL), dried (Na$_2$SO$_4$), filtered and concentrated under reduced pressure. The residue was purified by 4 g SiO$_2$ column using a gradient elution of 0-60% EtOAc in hexanes. Fractions containing product were combined and the solvents were removed in vacuo to provide the product (25.0 mg, 10% over two steps) as colourless gum. MS: m/z=667 (M+H$^+$).

Step 2: (3R)—N-(4-{2-[(2R,5R)-5-(1H-benzimidazol-2-yl)morpholin-2-yl]ethyl}-5-fluoropyridin-3-yl)-3-(4-fluorophenyl)-3-phenylpropanamide To a solution of (2R,5R)-tert-butyl 5-(1H-benzo[d]imidazol-2-yl)-2-(2-(3-fluoro-5-((R)-3-(4-fluorophenyl)-3-phenylpropanamido)pyridin-4-yl)ethyl)morpholine-4-carboxylate (25.0 mg, 0.04 mmol) in CH$_2$Cl$_2$ (2.00 mL) was added TFA (1.00 mL) and mixture was stirred at room temperature for 2 h. The solvent was removed under reduced pressure. The residue was purified by 24 g C18 column using a gradient elution of 10-60% acetonitrile in water. Fractions containing product were combined and the solvents were removed in vacuo and lyophilized to provide the product (20.0 mg, 60%) as a white solid. MS: m/z=568 (M+H$^+$).

Example 72

N-(4-{2-[(2R,5R)-5-(1H-benzimidazol-2-yl)morpholin-2-yl]ethyl}-5-fluoropyridin-3-yl)-4-fluoro-β-(4-fluorophenyl)-Nα-(methoxycarbonyl)-L-phenylalaninamide

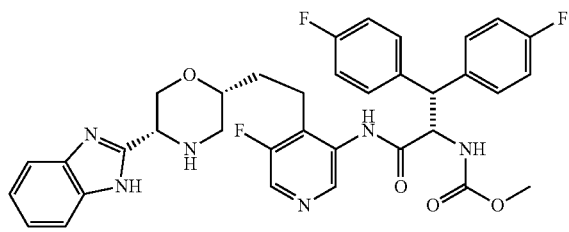 [SMILES: COC(=O)N[C@H](C(=O)Nc1cncc(F)c1CC[C@@H]1CN[C@H](c2nc3ccccc3[nH]2)CO1)C(c1ccc(F)cc1)c1ccc(F)cc1]

Step 1. (3S,6R)-6-(2-(3-((R)-3,3-Bis(4-fluorophenyl)-2-((methoxycarbonyl)amino)propanamido)-5-fluoropyridin-4-yl)ethyl)-4-(tert-butoxycarbonyl)morpholine-3-carboxylic acid

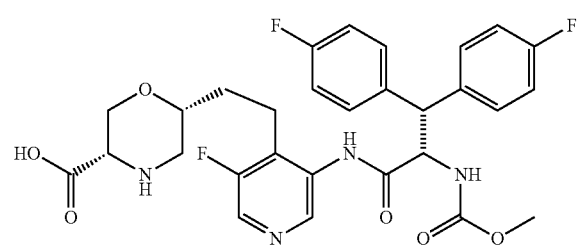 [SMILES: COC(=O)N[C@H](C(=O)Nc1cncc(F)c1CC[C@@H]1CN[C@H](C(=O)O)CO1)C(c1ccc(F)cc1)c1ccc(F)cc1]

To a solution of (2R,5R)-tert-butyl 2-(2-(3-((R)-3,3-bis(4-fluorophenyl)-2-((methoxycarbonyl)amino)propanamido)-5-fluoropyridin-4-yl)ethyl)-5-(hydroxymethyl)morpholine-4-carboxylate (0.503 g, 0.748 mmol) in DMF (3.74 ml) was added 0.85 g of 4 A sieves followed by PDC (2.81 g, 7.48 mmol). The reaction stirred at room temp overnight. The reaction was quenched with saturated aq. KH$_2$PO$_4$ and the mixture was extracted ethyl acetate (×3). The combined organic fractions were dried (MgSO$_4$), filtered and the solvent was evaporated under reduced pressure. Purification on silica gel (24 g) eluting with a gradient of 0-10% MeOH/DCM afforded the title compound (235 mg, 0.342 mmol, 46% yield) as a yellow solid, MS (ESI): m/z=687.5 (MH+).

Step 2. (2R,5R)-tert-Butyl 5-(1H-benzo[d]imidazol-2-yl)-2-(2-(3-((S)-3,3-bis(4-fluorophenyl)-2-((methoxycarbonyl)amino)propanamido)-5-fluoropyridin-4-yl)ethyl)morpholine-4-carboxylate

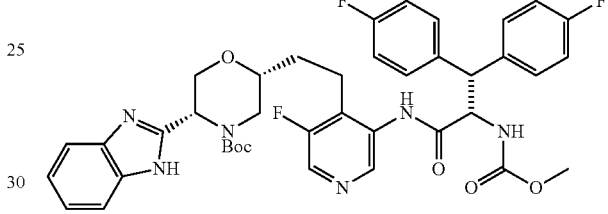

To a solution of (3S,6R)-6-(2-(3-((R)-3,3-bis(4-fluorophenyl)-2-((methoxycarbonyl)amino)propanamido)-5-fluoropyridin-4-yl)ethyl)-4-(tert-butoxycarbonyl)morpholine-3-carboxylic acid (0.078 g, 0.114 mmol) in DMF (0.568 ml) was added HATU (0.086 g, 0.227 mmol) and 2,6-lutidine (0.026 ml, 0.227 mmol). The reaction stirred for 5 min, followed by addition of O-phenylenediamine (0.015 g, 0.136 mmol). The reaction stirred for 2 hr at room temp. The reaction was quenched with saturated aq. NaHCO$_3$ and the mixture was extracted ethyl acetate (×3). The combined organic fractions were dried (MgSO$_4$), filtered and the solvent was evaporated under reduced pressure. The residue was dissolved in 1 mL AcOH and heated at 60° C. for 2 hrs. The reaction was quenched with saturated aq. NaHCO$_3$ and the mixture was extracted ethyl acetate (×3). The combined organic fractions were dried (MgSO$_4$), filtered and the solvent was evaporated under reduced pressure to afford the title compound (86 mg, 0.11 mmol, 100% yield), MS (ESI): m/z=759.5 (MH+); taken on crude.

Step 3. N-(4-{2-[(2R,5R)-5-(1H-benzimidazol-2-yl)morpholin-2-yl]ethyl}-5-fluoropyridin-3-yl)-4-fluoro-β-(4-fluorophenyl)-Nα-(methoxycarbonyl)-L-phenylalaninamide (2R,5R)-tert-Butyl 5-(1H-benzo[d]imidazol-2-yl)-2-(2-(3-((S)-3,3-bis(4-fluorophenyl)-2-((methoxycarbonyl)amino)propanamido)-5-fluoropyridin-4-yl)ethyl)morpholine-4-carboxylate (0.086 g, 0.113 mmol) was dissolved in 4M HCl in dioxane (0.850 ml). The reaction stirred at room temp for 2 hrs. The reaction was concentrated and the residue was purified by preparative HPLC Reverse phase (C-18), eluting with Acetonitrile/Water+0.1% TFA. The desired fractions were added to saturated aq. NaHCO$_3$ and the mixture was extracted ethyl acetate (×3). The combined organic fractions were dried (MgSO₄), filtered and the solvent was evaporated under reduced pressure to afford the title compound (41 mg, 0.062 mmol, 55% yield) as a colorless solid, MS (ESI): m/z=659.6 (MH+); 100% pure by LCMS.

Example 73

(3S)—N-(2-{2-[(2R,5R)-5-(1H-benzimidazol-2-yl)morpholin-2-yl]ethyl}-3-fluorophenyl)-3-(4-fluorophenyl)-3-(3-fluoropyridin-4-yl)propanamide

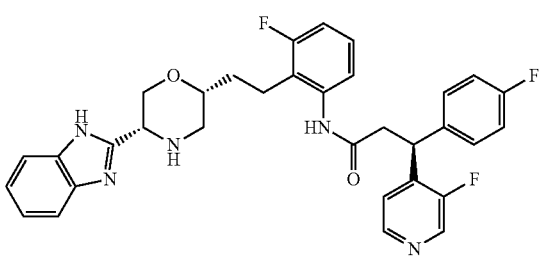 [SMILES: O=C(C[C@@H](c1ccc(F)cc1)c1ccncc1F)Nc1cccc(F)c1CC[C@@H]1CN[C@H](c2nc3ccccc3[nH]2)CO1]

Step 1: (2R,5R)-tert-butyl 2-((E)-2-fluoro-6-nitrostyryl)-5-(hydroxymethyl)morpholine-4-carboxylate

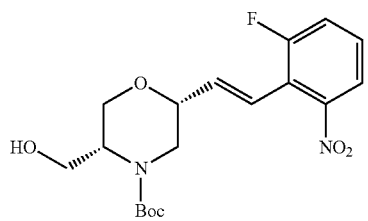 [SMILES: CC(C)(C)OC(=O)N1C[C@@H](/C=C/c2c(F)cccc2[N+](=O)[O-])OC[C@H]1CO]

To obtain the title compound, use the product from step 7 of Example 1 and follow the procedure described in step 10 of Example 1 (1 eq) and TBAF (1M in THF) (3 eq.). The mixture was stirred at rt for 2 hrs, diluted with EtOAc and saturated aqueous NaHCO₃ was added. The aqueous layer was extracted with EtOAc and the combined organic layers were washed with brine, dried over Na₂SO₄, filtered and concentrated. The crude product was purified by SiO₂ flash chromatography system using a solvent gradient of 0-100% EtOAc/CH₂Cl₂ to afford the desired compound.

Step 2: (3S,6R)-4-(tert-butoxycarbonyl)-6-((E)-2-fluoro-6-nitrostyryl)morpholine-3-carboxylic acid

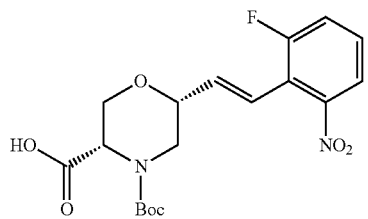 [SMILES: CC(C)(C)OC(=O)N1C[C@@H](/C=C/c2c(F)cccc2[N+](=O)[O-])OC[C@H]1C(=O)O]

To obtain the title compound, use the product from step 1 (1 eq) and follow the procedure described in step 11 of Example 1. The crude product was used as such for next step.

Step 3: (2R,5R)-tert-butyl 5-(1H-benzo[d]imidazol-2-yl)-2-((E)-2-fluoro-6-nitrostyryl)morpholine-4-carboxylate

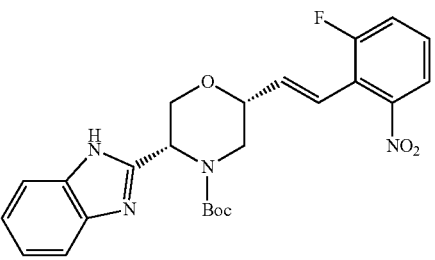 [SMILES: CC(C)(C)OC(=O)N1C[C@@H](/C=C/c2c(F)cccc2[N+](=O)[O-])OC[C@H]1c1nc2ccccc2[nH]1]

To obtain the title compound, use the product from step 2 (1 eq) and follow the procedure described in step 12 of Example 1. The crude product was purified by SiO₂ flash chromatography system using a solvent gradient of 0-100% EtOAc/CH₂Cl₂ to afford the desired compound as a solid.

Step 4: (2R,5R)-tert-butyl 2-(2-amino-6-fluorophenethyl)-5-(1H-benzo[d]imidazol-2-yl)morpholine-4-carboxylate

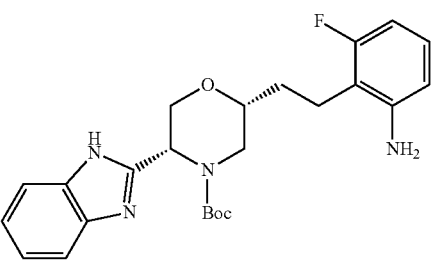 [SMILES: CC(C)(C)OC(=O)N1C[C@@H](CCc2c(N)cccc2F)OC[C@H]1c1nc2ccccc2[nH]1]

To obtain the title compound, use the product from step 3 (1 eq) and follow the procedure described in step 8 of Example 1. The crude product was purified by SiO₂ flash chromatography system using a solvent gradient of 0-100% EtOAc/CH₂Cl₂ to afford the desired compound.

Step 5: (2R,5R)-tert-butyl 5-(1H-benzo[d]imidazol-2-yl)-2-(2-fluoro-6-((S)-3-(4-fluorophenyl)-3-(3-fluoropyridin-4-yl)propanamido)phenethyl)morpholine-4-carboxylate

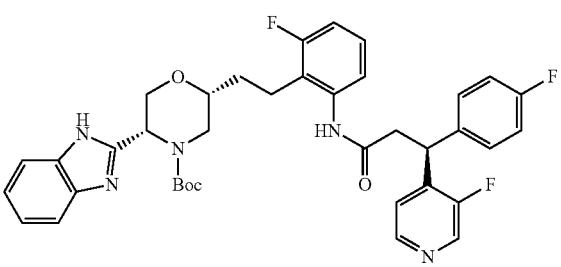 [SMILES: CC(C)(C)OC(=O)N1C[C@@H](CCc2c(F)cccc2NC(=O)C[C@@H](c2ccc(F)cc2)c2ccncc2F)OC[C@H]1c1nc2ccccc2[nH]1]

To obtain the title compound, use the product from step 4 (1 eq) and follow the procedure described in step 8 of Example 1 using (S)-3-(4-fluorophenyl)-3-(3-fluoropyridin-4-yl)propionic acid (1.5 eq). The crude product was purified by SiO₂ flash chromatography system using a solvent gradient of 0-100% EtOAc/CH₂Cl₂ to afford the desired compound as a white solid.

Step 6: (3S)—N-(2-{2-[(2R,5R)-5-(H-benzimidazol-2-yl)morpholin-2-yl]ethyl}-3-fluorophenyl)-3-(4-fluorophenyl)-3-(3-fluoropyridin-4-yl)propanamide To obtain the title compound, use the product from step 5 (1 eq) and follow the procedure described in step 13 of Example 1. The crude product was purified as described in step 13 of Example 1 to afford the desired compound as a white solid.
MS 586.2

Example 74

N-(4-{2-[(2R,5R)-5-(1H-benzimidazol-2-yl)morpholin-2-yl]ethyl}-5-fluoropyridin-3-yl)-4-fluoro-β-(4-fluorophenyl)-L-phenylalaninamide

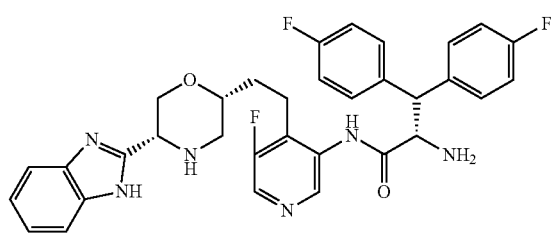 [SMILES: N[C@H](C(=O)Nc1cncc(F)c1CC[C@@H]1CN[C@H](c2nc3ccccc3[nH]2)CO1)C(c1ccc(F)cc1)c1ccc(F)cc1]

Step 1. (3S,6R)-4-(tert-Butoxycarbonyl)-6-(2-(3-((S)-2-((tert-butoxycarbonyl)amino)-3,3-bis(4-fluorophenyl)propanamido)-5-fluoropyridin-4-yl)ethyl)morpholine-3-carboxylic acid

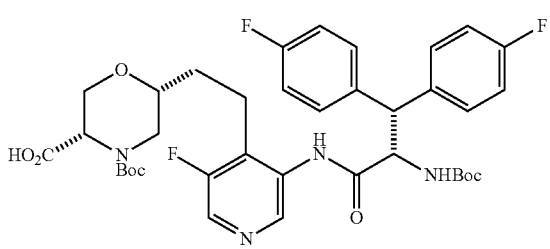 [SMILES: CC(C)(C)OC(=O)N[C@H](C(=O)Nc1cncc(F)c1CC[C@@H]1CN(C(=O)OC(C)(C)C)[C@H](C(=O)O)CO1)C(c1ccc(F)cc1)c1ccc(F)cc1]

PDC (5.32 g, 14.1 mmol) was added to a solution of (2R,5R)-tert-butyl 2-(2-(3-((S)-2-((tert-butoxycarbonyl)amino)-3,3-bis(4-fluorophenyl)propanamido)-5-fluoropyridin-4-yl)ethyl)-5-(hydroxymethyl)morpholine-4-carboxylate (1.01 g, 1.41 mmol) in DMF (7.07 ml) and 2 g of 4 Å molecular sieves and the reaction stirred at rt overnight. The reaction was quenched with aqueous potassium phosphate monobasic (saturated) and the mixture was extracted with ethyl acetate (×3). The combined organic fractions were dried (MgSO₄), filtered and the solvent was evaporated under reduced pressure. Purification on silica gel (80 g) eluting with a gradient 0-100% CHCl3 to 70:20:10 CHCl₃/ EtOAc/MeOH afforded the title compound (694 mg, 0.952 mmol, 67.4% yield) as a gum, MS (ESI): m/z=729.4 (MH+); 100% pure by LCMS.

Step 2. (2R,5R)-tert-Butyl 5-(1H-benzo[d]imidazol-2-yl)-2-(2-(3-((S)-2-((tert-butoxycarbonyl)amino)-3,3-bis(4-fluorophenyl)propanamido)-5-fluoropyridin-4-yl)ethyl)morpholine-4-carboxylate

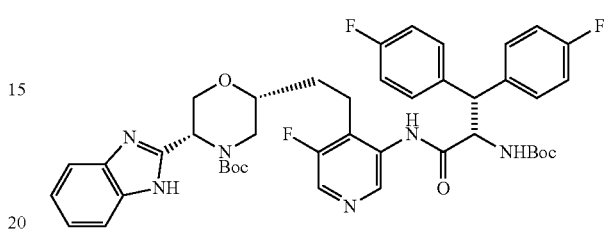

To a solution of (3S,6R)-4-(tert-Butoxycarbonyl)-6-(2-(3-((S)-2-((tert-butoxycarbonyl)amino)-3,3-bis(4-fluorophenyl)propanamido)-5-fluoropyridin-4-yl)ethyl)morpholine-3-carboxylic acid (66 mg, 0.091 mmol) in DMF (0.45 ml) was added HATU (0.069 g, 0.181 mmol) and 2,6-lutidine (0.021 ml, 0.181 mmol). The reaction stirred for 5 min, followed by addition of O-phenylenediamine (0.012 g, 0.109 mmol). The reaction stirred for 2 hr at room temp. The reaction was quenched with saturated aq. NaHCO₃ and the mixture was extracted ethyl acetate (×3). The combined organic fractions were dried (MgSO₄), filtered and the solvent was evaporated under reduced pressure. The residue was dissolved in 1 mL AcOH and heated at 60° C. for 2 hrs. The reaction was quenched with saturated aq. NaHCO₃ and the mixture was extracted ethyl acetate (×3). The combined organic fractions were dried (MgSO₄), filtered and the solvent was evaporated under reduced pressure. The residue was purified by preparative HPLC Reverse phase (C-18), eluting with 10-70% Acetonitrile/Water+0.1% TFA. The desired fractions were added to saturated aq. NaHCO₃ and the mixture was extracted ethyl acetate (×3). The combined organic fractions were dried (MgSO₄), filtered and the solvent was evaporated under reduced pressure to afford the title compound (49 mg, 0.061 mmol, 68% yield) as a colorless solid, MS (ESI): m/z=801.7 (MH+).

Step 3. N-(4-{2-[(2R,5R)-5-(1H-benzimidazol-2-yl)morpholin-2-yl]ethyl}-5-fluoropyridin-3-yl)-4-fluoro-β-(4-fluorophenyl)-L-phenylalaninamide (2R,5R)-tert-Butyl 5-(1H-benzo[d]imidazol-2-yl)-2-(2-(3-((S)-2-((tert-butoxycarbonyl)amino)-3,3-bis(4-fluorophenyl)propanamido)-5-fluoropyridin-4-yl)ethyl)morpholine-4-carboxylate (0.049 g, 0.061 mmol) was dissolved in 4M HCl solution in dioxane (0.459 ml, 1.836 mmol) and stirred at RT for 1 hr. The reaction was concentrated in vacuo to afford the title compound (45 mg, 0.060 mmol, 99% yield) as a colorless solid, MS (ESI): m/z=601.5 (MH+). MS 601.3

Example 75

N-(4-{2-[(2R,5R)-5-(5,6-difluoro-1H-benzimidazol-2-yl)morpholin-2-yl]ethyl}-5-fluoropyridin-3-yl)-4-fluoro-β-(4-fluorophenyl)-L-phenylalaninamide

Example 76

N-(4-{2-[(2R,5R)-5-(5,6-difluoro-1H-benzimidazol-2-yl)morpholin-2-yl]ethyl}-5-fluoropyridin-3-yl)-4-fluoro-β-(4-fluorophenyl)-Nα-(methoxycarbonyl)-L-phenylalaninamide

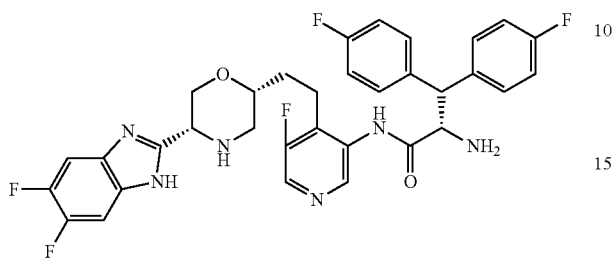

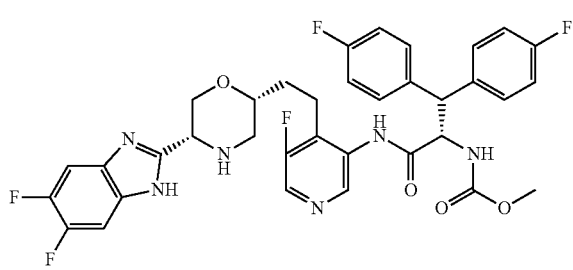 [SMILES: COC(=O)N[C@H](C(=O)Nc1cncc(F)c1CC[C@@H]1CN[C@H](c2nc3cc(F)c(F)cc3[nH]2)CO1)C(c1ccc(F)cc1)c1ccc(F)cc1]

The above example was prepared in an analogous fashion to Example 74 starting from (3S,6R)-4-(tert-butoxycarbonyl)-6-(2-(3-((S)-2-((tert-butoxycarbonyl)amino)-3,3-bis(4-fluorophenyl)propanamido)-5-fluoropyridin-4-yl)ethyl)morpholine-3-carboxylic acid and 1,2-diamino-4,5-difluorobenzene to afford the title compound as a colorless solid, MS (ESI): m/z=637.5 (MH+); 100% pure by LCMS.

The above example was prepared in an analogous fashion to Example 73 starting from (3S,6R)-6-(2-(3-((R)-3,3-bis(4-fluorophenyl)-2-((methoxycarbonyl)amino)propanamido)-5-fluoropyridin-4-yl)ethyl)-4-(tert-butoxycarbonyl)morpholine-3-carboxylic acid and 1,2-diamino-4,5-difluorobenzene to afford the title compound as a colorless solid, MS (ESI): m/z=695.5 (MH+); 100% pure by LCMS.

| Ex. | Structure | IUPAC Name | Exact Mass [M + H] ± |
|---|---|---|---|
| 77 | ![structure] | Nα-(methoxycarbonyl)-β-phenyl-N-(2-{2-[(2R,5R)-5-(1H-tetrazol-5-yl)morpholin-2-yl]ethyl}phenyl)-L-phenylalaninamide | 556.3 |
| 78 | ![structure] | N-(2-{2-[(2R,5S)-5-(5-benzyl-1,3,4-oxadiazol-2-yl)morpholin-2-yl]ethyl}phenyl)-Nalpha-(methoxycarbonyl)-β-phenyl-L-phenylalaninamide | 646.3 |

-continued

| Ex. | Structure | IUPAC Name | Exact Mass [M + H] ± |
|---|---|---|---|
| 79 | 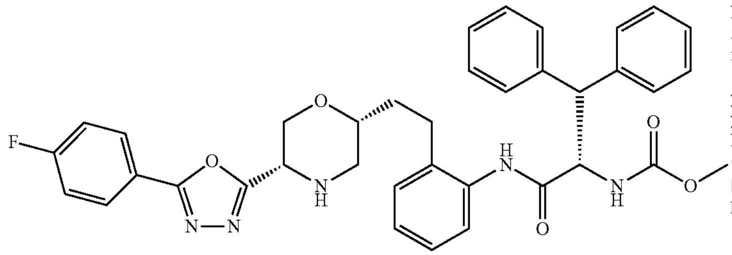 [SMILES: COC(=O)N[C@H](C(=O)Nc1ccccc1CC[C@@H]1CN[C@H](c2nnc(-c3ccc(F)cc3)o2)CO1)C(c1ccccc1)c1ccccc1] | N-[2-(2-{(2R,5S)-5-[5-(4-fluorophenyl)-1,3,4-oxadiazol-2-yl]morpholin-2-yl}ethyl)phenyl]-Nalpha-(methoxycarbonyl)-β-phenyl-L-phenylalaninamide | 650.3 |
| 80 | 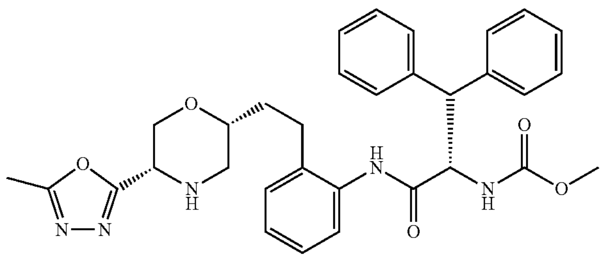 | Nalpha-(methoxycarbonyl)-N-(2-{2-[(2R,5S)-5-(5-methyl-1,3,4-oxadiazol-2-yl)morpholin-2-yl]ethyl}phenyl)-β-phenyl-L-phenylalaninamide | 570.3 |
| 81 | 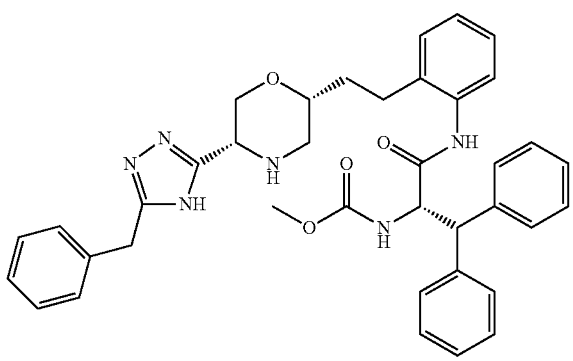 [SMILES: COC(=O)N[C@H](C(=O)Nc1ccccc1CC[C@@H]1CN[C@H](c2nnc(Cc3ccccc3)[nH]2)CO1)C(c1ccccc1)c1ccccc1] | N-(2-{2-[(2R,5R)-5-(5-benzyl-4H-1,2,4-triazol-3-yl)morpholin-2-yl]ethyl}phenyl)-Nalpha-(methoxycarbonyl)-β-phenyl-L-phenylalaninamide | 645.3 |
| 82 | 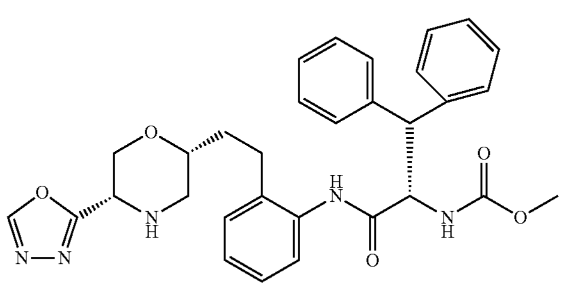 [SMILES: COC(=O)N[C@H](C(=O)Nc1ccccc1CC[C@@H]1CN[C@H](c2nnco2)CO1)C(c1ccccc1)c1ccccc1] | Nalpha-(methoxycarbonyl)-N-(2-{2-[(2R,5S)-5-(1,3,4-oxadiazol-2-yl)morpholin-2-yl]ethyl}phenyl)-β-phenyl-L-phenylalaninamide | 556.3 |

-continued

| Ex. | Structure | IUPAC Name | Exact Mass [M + H] ± |
|---|---|---|---|
| 83 | 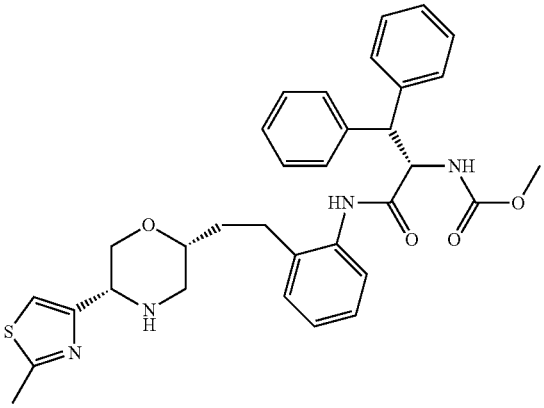 [SMILES: COC(=O)N[C@H](C(=O)Nc1ccccc1CC[C@@H]1CN[C@H](c2csc(C)n2)CO1)C(c1ccccc1)c1ccccc1] | Nalpha-(methoxycarbonyl)-N-(2-{2-[(2R,5R)-5-(2-methyl-1,3-thiazol-4-yl)morpholin-2-yl]ethyl}phenyl)-β-phenyl-L-phenylalaninamide | 585.3 |
| 84 | 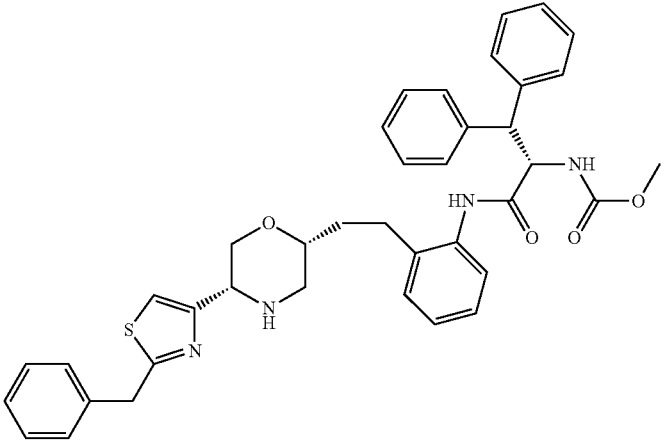 [SMILES: COC(=O)N[C@H](C(=O)Nc1ccccc1CC[C@@H]1CN[C@H](c2csc(Cc3ccccc3)n2)CO1)C(c1ccccc1)c1ccccc1] | N-(2-{2-[(2R,5R)-5-(2-benzyl-1,3-thiazol-4-yl)morpholin-2-yl]ethyl}phenyl)-Nalpha-(methoxycarbonyl)-β-phenyl-L-phenylalaninamide | 661.3 |
| 85 | 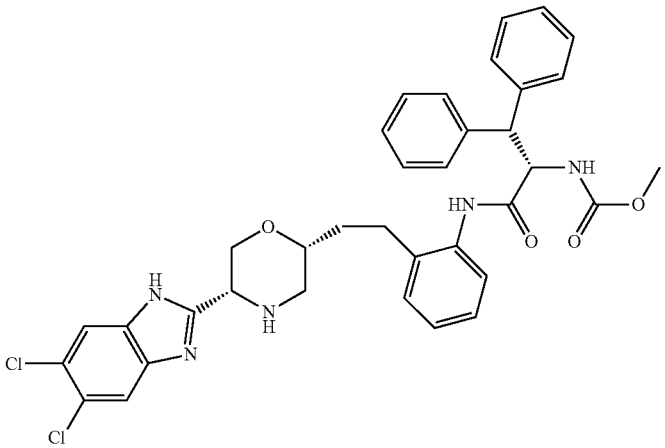 [SMILES: COC(=O)N[C@H](C(=O)Nc1ccccc1CC[C@@H]1CN[C@H](c2nc3cc(Cl)c(Cl)cc3[nH]2)CO1)C(c1ccccc1)c1ccccc1] | N-(2-{2-[(2R,5R)-5-(5,6-dichloro-1H-benzimidazol-2-yl)morpholin-2-yl]ethyl}phenyl)-Nalpha-(methoxycarbonyl)-β-phenyl-L-phenylalaninamide | 672.2 |
| 86 | 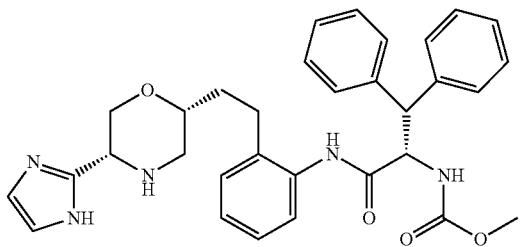 [SMILES: COC(=O)N[C@H](C(=O)Nc1ccccc1CC[C@@H]1CN[C@H](c2ncc[nH]2)CO1)C(c1ccccc1)c1ccccc1] | N-(2-{2-[(2R,5R)-5-(1H-imidazol-2-yl)morpholin-2-yl]ethyl}phenyl)-Nalpha-(methoxycarbonyl)-β-phenyl-L-phenylalaninamide | 554.3 |

| Ex. | Structure | IUPAC Name | Exact Mass [M + H] ± |
|---|---|---|---|
| 87 | 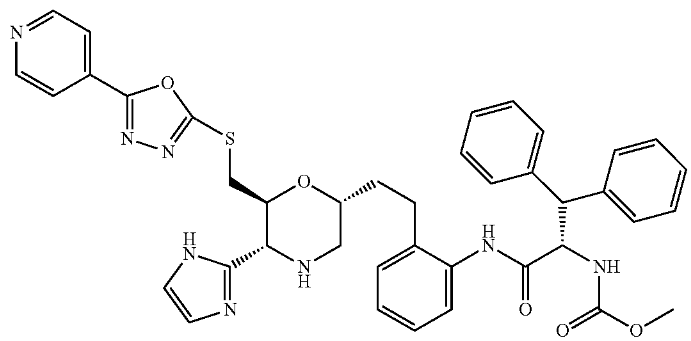 [SMILES: COC(=O)N[C@H](C(=O)Nc1ccccc1CC[C@@H]1CN[C@H](c2ncc[nH]2)[C@@H](CSc2nnc(-c3ccncc3)o2)O1)C(c1ccccc1)c1ccccc1] | N-(2-{2-[(2R,5R)-(1H-imidazol-2-yl)-6-{[(5-pyridin 4-yl-1,3,4-oxadiazol-2-yl)sulfanyl]methyl} morpholin-2-yl]ethyl}phenyl)-Nalpha-(methoxycarbonyl)-β-phenyl-L-phenylalaninamide | 745.3 |
| 88 | 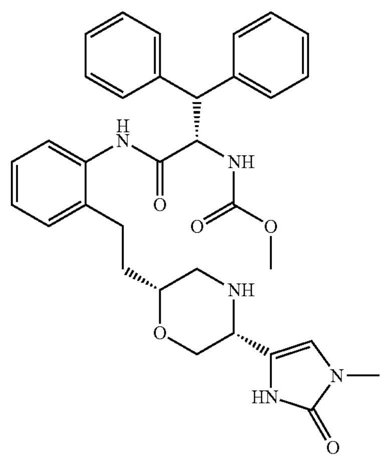 [SMILES: COC(=O)N[C@H](C(=O)Nc1ccccc1CC[C@@H]1CN[C@H](c2cn(C)c(=O)[nH]2)CO1)C(c1ccccc1)c1ccccc1] | Nalpha-(methoxycarbonyl)-N-(2-{2-[(2R,5R)-5-(1-methyl-2-oxo-2,3-dihydro-1H-imidazol-4-yl)morpholin-2-yl]ethyl}phenyl)-β-phenyl-L-phenylalaninamide | 584.3 |
| 89 | 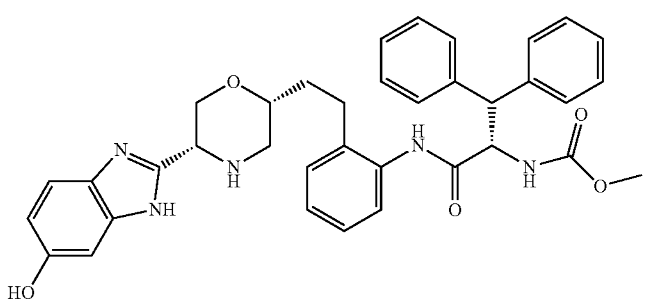 [SMILES: COC(=O)N[C@H](C(=O)Nc1ccccc1CC[C@@H]1CN[C@H](c2nc3ccc(O)cc3[nH]2)CO1)C(c1ccccc1)c1ccccc1] | N-(2-{2-[(2R,5R)-5-(5-hydroxy-3H-imidazo[4,5-b]pyridin-2-yl)morpholin-2-yl]ethyl}phenyl)-Nalpha-(methoxycarbonyl)-β-phenyl-L-phenylalaninamide | 621.3 |
| 90 | 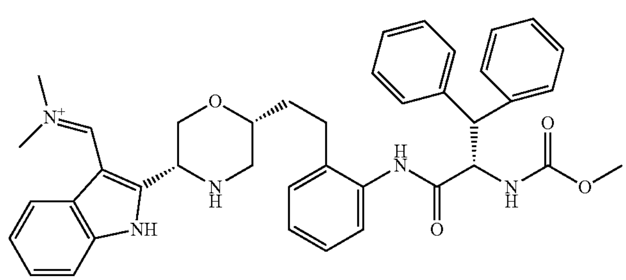 [SMILES: COC(=O)N[C@H](C(=O)Nc1ccccc1CC[C@@H]1CN[C@H](c2[nH]c3ccccc3c2C=[N+](C)C)CO1)C(c1ccccc1)c1ccccc1] | N-[(2-{(3R,6R)-6-[2-(2-{[N-(methoxycarbonyl)-β-phenyl-L-phenylalanyl]amino} phenyl)ethyl] morpholin-3-yl}-1H-indol-3-yl)methylidene]-N-methylmethanaminium | 659.3 |

-continued

| Ex. | Structure | IUPAC Name | Exact Mass [M + H] ± |
|---|---|---|---|
| 91 | 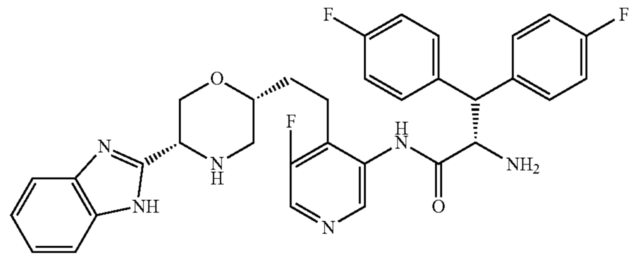 [SMILES: N[C@H](C(=O)Nc1cncc(F)c1CC[C@@H]1CN[C@H](c2nc3ccccc3[nH]2)CO1)C(c1ccc(F)cc1)c1ccc(F)cc1] | N-(4-{2-[(2R,5R)-5-(1H-benzimidazol-2-yl)morpholin-2-yl]ethyl}-5-fluoropyridin-3-yl)-4-fluoro-β-(4-fluorophenyl)-L-phenylalaninamide | 601.3 |
| 92 | 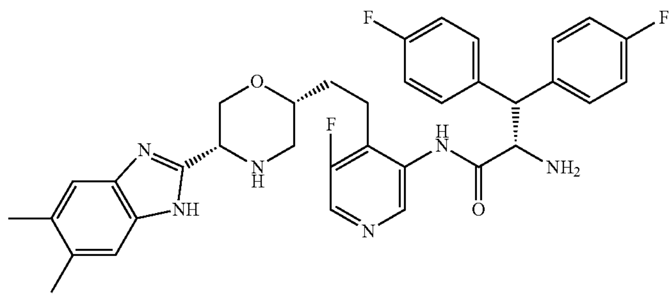 [SMILES: Cc1cc2nc([C@@H]3CO[C@H](CCc4c(F)cncc4NC(=O)[C@@H](N)C(c4ccc(F)cc4)c4ccc(F)cc4)CN3)[nH]c2cc1C] | N-(4-{2-[(2R,5R)-5-(5,6-dimethyl-1H-benzimidazol 2-yl)morpholin-2-yl]ethyl}-5-fluoropyridin-3-yl)-4-fluoro-β-(4-fluorophenyl)-L-phenylalaninamide | 629.3 |
| 93 | 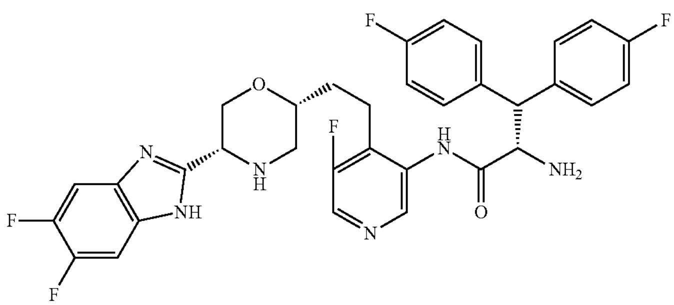 [SMILES: N[C@H](C(=O)Nc1cncc(F)c1CC[C@@H]1CN[C@H](c2nc3cc(F)c(F)cc3[nH]2)CO1)C(c1ccc(F)cc1)c1ccc(F)cc1] | N-(4-{2-[(2R,5R)-5-(5,6-difluoro-1H-benzimidazol-2-yl)morpholin-2-yl]ethyl}-5-fluoropyridin-3-yl)-4-fluoro-β-(4-fluorophenyl)-L-phenylalaninamide | 637.2 |
| 94 | 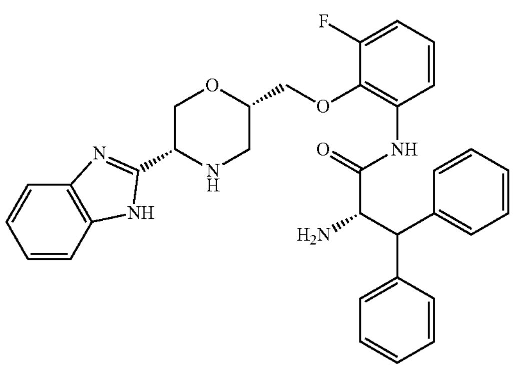 [SMILES: N[C@H](C(=O)Nc1cccc(F)c1OC[C@@H]1CN[C@H](c2nc3ccccc3[nH]2)CO1)C(c1ccccc1)c1ccccc1] | N-(2-{[(2S,5R)-5-(1H-benzimidazol-2-yl)morpholin-2-yl]methoxy}-3-fluorophenyl)-β-phenyl-L-phenylalaninamide | 566.3 |
| 95 | 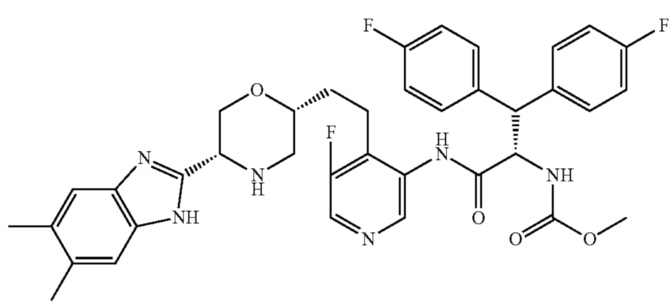 [SMILES: COC(=O)N[C@H](C(=O)Nc1cncc(F)c1CC[C@@H]1CN[C@H](c2nc3cc(C)c(C)cc3[nH]2)CO1)C(c1ccc(F)cc1)c1ccc(F)cc1] | N-(4-{2-[(2R,5R)-5-(5,6-dimethyl-1H-benzimidazol-2-yl)morpholin-2-yl]ethyl}-5-fluoropyridin-3-yl)-4-fluoro-β-(4-fluorophenyl)-Nalpha-(methoxycarbonyl)-L-phenylalaninamide | 687.3 |

-continued

| Ex. | Structure | IUPAC Name | Exact Mass [M + H] ± |
|---|---|---|---|
| 96 | 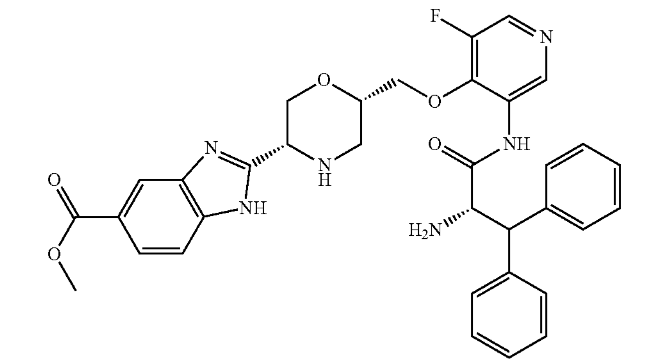 [SMILES: COC(=O)c1ccc2[nH]c([C@@H]3CO[C@H](COc4c(F)cncc4NC(=O)[C@@H](N)C(c4ccccc4)c4ccccc4)CN3)nc2c1] | methyl 2-[(3R,6R)-6-(2-{3-fluoro-5-[(β-phenyl-L-phenylalanyl)amino]pyridin-4-yl}ethyl)morpholin-3-yl]-1H-benzimidazole-5-carboxylate | 623.3 |
| 97 | 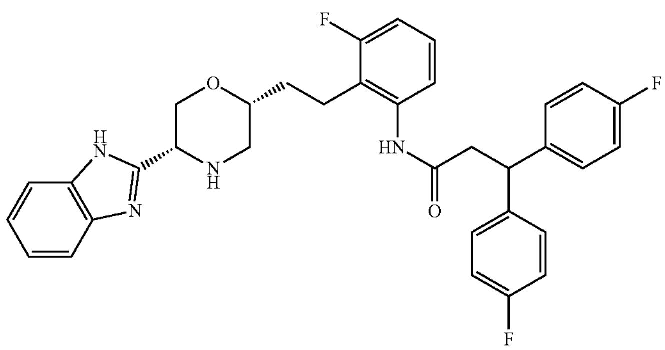 [SMILES: O=C(CC(c1ccc(F)cc1)c1ccc(F)cc1)Nc1cccc(F)c1CC[C@@H]1CN[C@H](c2nc3ccccc3[nH]2)CO1] | N-(2-{2-[(2R,5R)-5-(1H-benzimidazol-2-yl)morpholin-2-yl]ethyl}-3-fluorophenyl)-3,3-bis(4-fluorophenyl)propanamide | 585.2 |
| 98 | 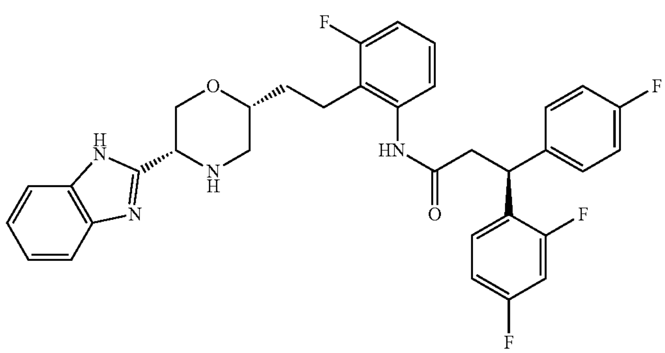 [SMILES: O=C(C[C@@H](c1ccc(F)cc1)c1ccc(F)cc1F)Nc1cccc(F)c1CC[C@@H]1CN[C@H](c2nc3ccccc3[nH]2)CO1] | (3S)-N-(2-{2-[(2R,5R)-5-(1H-benzimidazol-2-yl)morpholin-2-yl]ethyl}-3-fluorophenyl)-3-(2,4-difluorophenyl)-3-(4-fluorophenyl)propanamide | 603.2 |
| 99 | 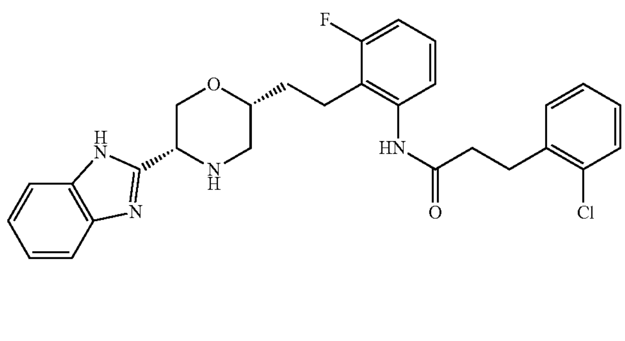 [SMILES: O=C(CCc1ccccc1Cl)Nc1cccc(F)c1CC[C@@H]1CN[C@H](c2nc3ccccc3[nH]2)CO1] | N-(2-{2-[(2R,5R)-5-(1H-benzimidazol-2-yl)morpholin-2-yl]ethyl}-3-fluorophenyl)-3-(2-chlorophenyl)propanamide | 507.2 |

-continued

| Ex. | Structure | IUPAC Name | Exact Mass [M + H] ± |
|---|---|---|---|
| 100 | 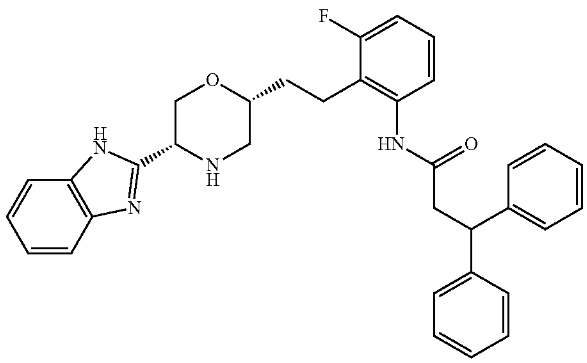 [SMILES: O=C(CC(c1ccccc1)c1ccccc1)Nc1cccc(F)c1CC[C@@H]1CN[C@H](c2nc3ccccc3[nH]2)CO1] | N-(2-{2-[(2R,5R)-5-(1H-benzimidazol-2-yl)morpholin-2-yl]ethyl}-3-fluorophenyl)-3,3-diphenylpropanamide | 549.3 |
| 101 | 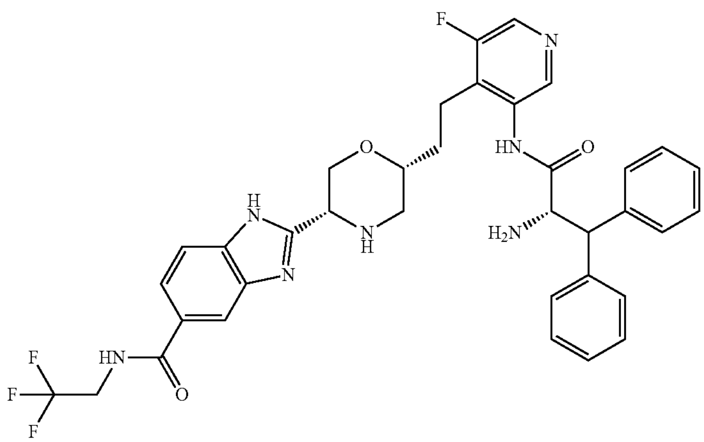 [SMILES: N[C@H](C(=O)Nc1cncc(F)c1CC[C@@H]1CN[C@H](c2nc3cc(C(=O)NCC(F)(F)F)ccc3[nH]2)CO1)C(c1ccccc1)c1ccccc1] | N-(5-fluoro-4-{2-[(2R,5R)-5-{5-[(2,2,2-trifluoroethyl)carbamoyl]-1H-benzimidazol-2-yl}morpholin-2-yl]ethyl}pyridin-3-yl)-β-phenyl-L-phenylalaninamide | 690.3 |
| 102 | 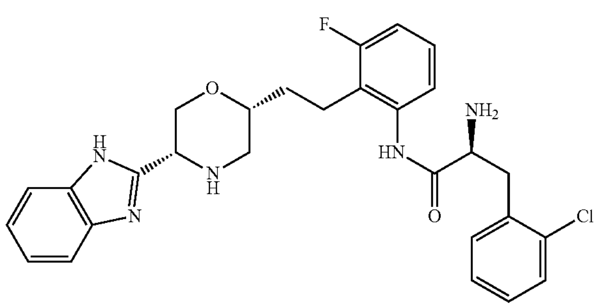 [SMILES: N[C@@H](Cc1ccccc1Cl)C(=O)Nc1cccc(F)c1CC[C@@H]1CN[C@H](c2nc3ccccc3[nH]2)CO1] | N-(2-{2-[(2R,5R)-5-(1H-benzimidazol-2-yl)morpholin-2-yl]ethyl}-3-fluorophenyl)-2-chloro-L-phenylalaninamide | 522.2 |
| 103 | 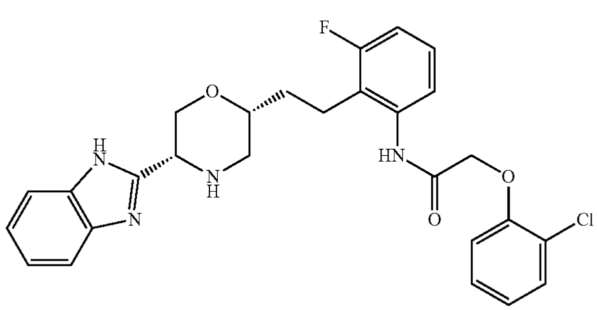 [SMILES: O=C(COc1ccccc1Cl)Nc1cccc(F)c1CC[C@@H]1CN[C@H](c2nc3ccccc3[nH]2)CO1] | N-(2-{2-[(2R,5R)-5-(1H-benzimidazol-2-yl)morpholin-2-yl]ethyl}-3-fluorophenyl)-2-(2-chlorophenoxy)acetamide | 509.2 |

| Ex. | Structure | IUPAC Name | Exact Mass [M + H] ± |
|---|---|---|---|
| 104 | 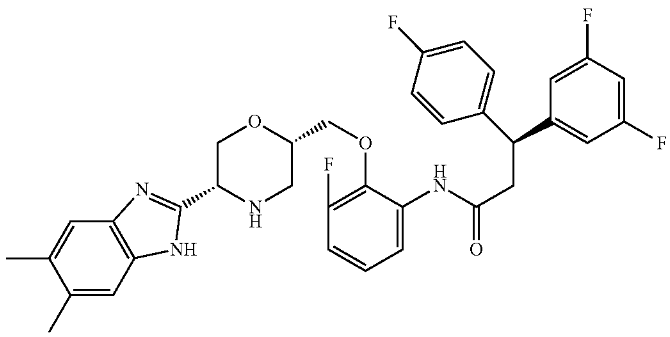 [SMILES: Cc1cc2nc([C@@H]3CO[C@H](COc4c(F)cccc4NC(=O)C[C@@H](c4ccc(F)cc4)c4cc(F)cc(F)c4)CN3)[nH]c2cc1C] | (3S)-3-(3,5-difluorophenyl)-N-(2-{[(2S,5R)-5-(5,6-dimethyl-1H-benzimidazol-2-yl)morpholin-2-yl]methoxy}-3-fluorophenyl)-3-(4-fluorophenyl)propanamide | 633.2 |

Assay for Inhibition of Microbial Expressed HIV Protease ("Pepcleav")

Studies of the inhibition of the wildtype HIV-1 protease (which was expressed in *Escherichia coli*) were carried out with a peptide substrate [Val-Ser-Gln-Asn-(βnaphthyl)Ala-Pro-Ile-Val (SEQ ID NO: 1)]. The inhibitor was first preincubated with the HIV-1 protease (wild type) enzyme in assay buffer (50 mM sodium acetate, pH 5.5, 100 mM NaCl, and 0.1% BSA) for 30 minutes at room temperature. Substrate was added to 400 micromolar in a total volume of 20 microliters containing 20 picomolar HIV-1 protease (final) and the reaction was incubated for 1 hour at 30° C. The reaction was quenched with the addition of formic acid and indinavir to 0.012% and 150 nM final concentrations, respectively. The product formation was determined after separation of product and substrate on a Zorbax Eclipse XDB-C18 column connected to an API 4000 mass spectrometer (Applied Biosystems) with multiple reaction monitoring (transitions were 644.5/428.9 and 615.4/422.2 (M1/M3) for product and indinavir respectively). The extent of inhibition of the reaction was determined from the peak area of the products. Analysis of the products, independently synthesized, provided quantitation standards and confirmation of the product composition. Compounds in the Examples of the present invention exhibited inhibition of HIV-1 protease in this assay as noted below in Table 1.

Antiviral Assays in Cell Culture ("Spread")

Acute Infection Assay ("Spread") data were generated using HIV-1 (H9IIIB strain) infection of MT-4 human T-lymphoid cells in 10% FBS, and according to the methods disclosed by J. P. Vacca et al, "L-735,524: An orally bioavailable human immunodeficiency virus type 1 protease inhibitor," Proc. Natl. Acad. Sci. USA, Vol. 91, pp. 4096-4100 (April 1994).

Data Table 1 displays data regarding Pepcleave and Spread data for each of the example compounds. Both columns of data in the table reflect the mean of at least two independent experiments

DATA TABLE 1

| Example | PEPCLEAV (nM) | Viking 50% (nM) |
|---|---|---|
| 1 | 0.03738 | |
| 2 | 7.964 | |
| 3 | 0.06385 | |

DATA TABLE 1-continued

| Example | PEPCLEAV (nM) | Viking 50% (nM) |
|---|---|---|
| 4 | 0.09234 | |
| 5 | 7.409 | |
| 6 | 0.3339 | |
| 7 | 37.14 | |
| 8 | 0.5043 | |
| 9 | 0.05163 | |
| 10 | 1.586 | |
| 11 | 0.4108 | |
| 12 | 0.7057 | |
| 13 | 0.1373 | |
| 14 | 0.5915 | |
| 15 | 0.05594 | |
| 16 | 0.02462 | |
| 17 | 0.07472 | |
| 18 | 0.1252 | |
| 19 | 0.5726 | |
| 20 | 0.5246 | |
| 21 | 1.682 | |
| 22 | 1.932 | |
| 23 | 3.134 | |
| 24 | 16.32 | |
| 25 | 25.98 | |
| 26 | 65.56 | |
| 27 | 0.6584 | |
| 28 | 0.122 | |
| 29 | 0.0127 | |
| 30 | 0.1461 | |
| 31 | 0.00965 | |
| 32 | 0.03999 | |
| 33 | 4.076 | |
| 34 | 0.1678 | |
| 35 | 0.1588 | |
| 36 | 16.46 | |
| 37 | 246.3 | |
| 38 | 1.995 | |
| 39 | 652.7 | |
| 40 | ND | |
| 41 | 304.2 | |
| 42 | 2.625 | |
| 43 | 1.021 | |
| 44 | 0.5677 | |
| 45 | 0.041 | |
| 46 | 840.7 | |
| 47 | 378.1 | |
| 48 | 1.813 | |
| 49 | 824.2 | |
| 50 | 36.26 | |
| 51 | 576.5 | |
| 52 | 250 | |
| 53 | 44.39 | |
| 54 | 143 | |
| 55 | 152.3 | |

DATA TABLE 1-continued

| Example | PEPCLEAV (nM) | Viking 50% (nM) |
|---|---|---|
| 56 | 98.28 | |
| 57 | 70.18 | |
| 58 | 76.24 | |
| 59 | 96.38 | |
| 60 | 88.59 | |
| 61 | 549.7 | |
| 62 | 156.2 | |
| 63 | | 63 |
| 64 | | 16 |
| 65 | | 13 |
| 66 | | 22 |
| 67 | | 23 |
| 68 | | 52 |
| 69 | 0.01 | 80 |
| 70 | 0.01 | |
| 71 | 0.01 | |
| 72 | 0.01 | |
| 73 | 0.01 | |
| 74 | 0.01 | |
| 75 | 0.01 | |
| 76 | 0.02 | |
| 77 | 3.5 | |
| 78 | 62 | |
| 79 | 59 | |
| 80 | 220 | |
| 81 | 2.8 | |
| 82 | 280 | |
| 83 | 89 | |
| 84 | 150 | |
| 85 | 0.4 | |
| 86 | 1.8 | |
| 87 | 0.6 | |
| 88 | 310 | |
| 89 | 150 | |
| 90 | 68 | |
| 91 | 0.07 | |
| 92 | 0.06 | |
| 93 | 0.02 | |
| 94 | 0.22 | |
| 95 | 0.03 | |
| 96 | 2.1 | |
| 97 | 0.04 | |
| 98 | 0.05 | |
| 99 | 11 | |
| 100 | 0.65 | |
| 101 | 26 | |
| 102 | 17 | |
| 103 | 31 | |
| 104 | 1.1 | |

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:
1. A compound of Formula I:

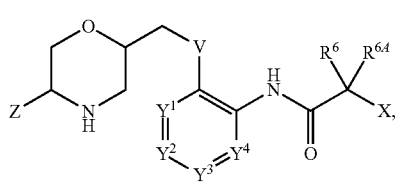

(I)

or a pharmaceutically acceptable salt thereof, wherein:
V is $CH_2$ or O;
$Y^1$, $Y^2$, $Y^3$ and $Y^4$ are independently selected from C(R) and N;
X is selected from H and $NR^7R^8$;
R is selected from H, halo, hydroxy, $C_{1-4}$alkyl, $C_{1-4}$alkoxy, $C_{1-4}$alkyl-$S(O)_k$—, $CF_3$, CN, and benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, $C_{1-4}$alkyl, $C_{1-4}$alkoxy, $CF_3$ and CN;
each k is independently 0, 1 or 2;
Z is HetA;
$R^6$ is selected from:

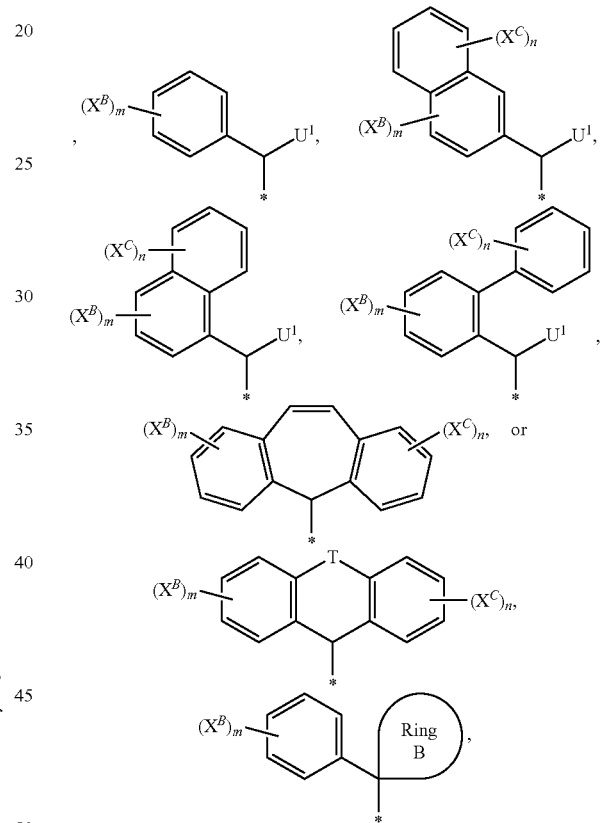

wherein the asterisk (*) denotes the point of attachment to the rest of the compound and $U^1$ is selected from (1) H, (2) $C_{1-10}$alkyl, wherein said $C_{1-10}$alkyl is optionally substituted with 1 to 4 substituents independently selected from halogen, $C_{1-4}$alkyl, $C_{1-4}$haloalkyl, hydroxy and $C_{1-4}$alkoxy, (3) $C_{3-7}$cycloalkyl, wherein said $C_{3-7}$cycloalkyl is optionally substituted with 1 to 4 substituents independently selected from halogen, $C_{1-4}$alkyl, $C_{1-4}$haloalkyl, hydroxy and $C_{1-4}$alkoxy, (4) ArylA, (5) HetA, (6) HetB, (7) $C_{1-10}$alkyl substituted with ArylA, (8) $C_{1-10}$alkyl substituted with HetA, and (9) $C_{1-10}$alkyl substituted with HetB; and Ring B is selected from $C_{3-7}$cycloalkyl and HetB, wherein $C_{3-7}$cycloalkyl is optionally substituted with 1 to 4 substituents independently selected from halogen, OH, $C_{1-4}$alkyl, $C_{1-4}$fluoroalkyl and $C_{1-4}$alkoxy;
$R^{6A}$ is selected from H or $C_{1-6}$ alkyl;

each $X^B$, each $X^C$, each $Y^B$ and each $Y^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) C(O)$NH_2$,
(25) C(O)N(H)—$C_{1-6}$ alkyl,
(26) C(O)N(—$C_{1-6}$ alkyl)$_2$,
(27) C(O)N(H)C(O)—$C_{1-6}$ alkyl,
(28) C(O)N(H)CH(O)
(29) $SO_2H$,
(30) $SO_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or —$CH_2$—HetA, optionally substituted with 1 to 5 substituents selected from halogen and $C_{1-6}$ alkyl,
(33) trimethylsilyl, and
(34) $C_{2-6}$alkenyl,
wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) $NO_2$,
(k) $NH_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) $SO_2$—$C_{1-6}$ alkyl;
T is O, S, S(O), or $SO_2$;
m is an integer equal to 0, 1, 2, or 3;
n is an integer equal to 0, 1, 2, or 3;
$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or $SO_2$—$R^K$;

$R^8$ is H, $C_{1-6}$ alkyl, $C_{1-6}$ haloalkyl or $C_{3-6}$ cycloalkyl;
$R^K$ is:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) $C_{1-6}$ alkyl substituted with C(O)O—$C_{1-6}$ alkyl,
(9) $C_{1-6}$ alkyl substituted with C(O)OH,
(10) $C_{1-6}$ alkyl substituted with C(O)—$C_{1-6}$ alkyl,
(11) N(H)—$C_{1-6}$ alkyl,
(12) N(—$C_{1-6}$ alkyl)$_2$,
(13) $C_{1-6}$ alkyl substituted with $NH_2$, N(H)—$C_{1-6}$ alkyl, or N(—$C_{1-6}$ alkyl)$_2$,
(14) ArylA,
(15) $C_{1-6}$ alkyl substituted with ArylA,
(16) O—$C_{1-6}$ alkyl substituted with ArylA,
(17) HetA,
(18) $C_{1-6}$ alkyl substituted with HetA,
(19) O—$C_{1-6}$ alkyl substituted with HetA,
(20) HetB,
(21) O-HetB, or
(22) O—$C_{1-6}$ alkyl substituted with HetB;
each ArylA is an aryl which is independently phenyl or naphthyl, wherein the phenyl or naphthyl is optionally substituted with $Y^B$ from one up to the maximum number of substitutable positions as allowed by valence;
each HetA is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with $Y^C$ from one up to the maximum number of substitutable positions as allowed by valence; and
each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with one or more substituents, up to the maximum number allowed by valance, each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)$NH_2$, C(O)N(H)—$C_{1-6}$ alkyl, C(O)N(—$C_{1-6}$ alkyl)$_2$, C(O)H, C(O)—$C_{1-6}$ alkyl, $CO_2H$, $CO_2$—$C_{1-6}$ alkyl, $SO_2H$, or $SO_2$—$C_{1-6}$ alkyl.

2. The compound according to claim 1, or a pharmaceutically acceptable salt thereof, wherein $R^6$ is:

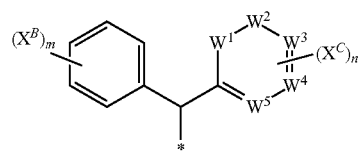

wherein $W^1$ to $W^5$ are independently CH or N, with the proviso that no more than three are N, and $R^{6A}$ is H.

3. The compound according to claim 2 of Formula

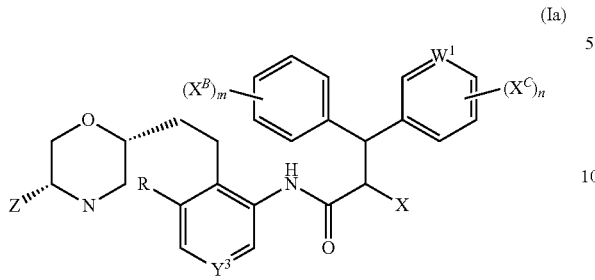

(Ia)

or a pharmaceutically acceptable salt thereof, wherein $W^2$ is CH or N.

4. The compound according to claim 3, or a pharmaceutically acceptable salt thereof, wherein:
R is H or fluoro,
$Y^3$ is CH or N,
$X^B$ and $X^C$ are independently selected from F, Cl, Br, —OCH$_3$, —CF$_3$ and —OCF$_3$, and
m and n are independently 0, 1 or 2.

5. The compound according to claim 4, or a pharmaceutically acceptable salt thereof, wherein X is selected from: H, —NH$_2$ and —N(H)—C(O)—R$^K$ wherein R$^K$ is O—C$_{1-6}$ alkyl or O—C$_{1-6}$ fluoroalkyl.

6. The compound according claim 4, or a pharmaceutically acceptable salt thereof, wherein $W^2$ is CH, one $X^B$ group is present and is a substituent at the 4-position, one or two $X^C$ groups are present and is a substituent at the 3-position or are substituents at the 3,5-positions respectively, and the $X^B$ group is a different group with respect to either $X^C$ group.

7. The compound according to claim 1 of Formula Ib

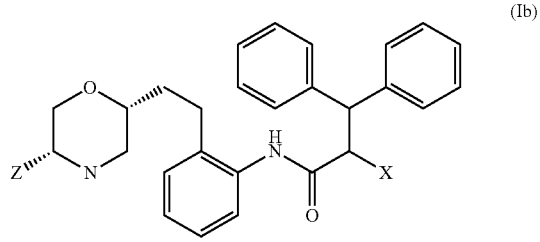

(Ib)

or a pharmaceutically acceptable salt thereof, wherein X is selected from: —NH$_2$ and —NHC(O)—R$^K$ wherein R$^K$ is O—C$_{1-6}$ alkyl or O—C$_{1-6}$ fluoroalkyl.

8. The compound according to claim 7, or a pharmaceutically acceptable salt thereof, wherein Z is selected from

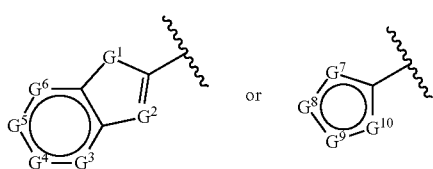

wherein
$G^1$ is selected from O, S, N(R$^9$) and C(R$^9$)(R$^{10}$);
$G^2$, $G^3$, $G^4$, $G^5$ and $G^6$ are independently selected N and C(R$^9$);

$G^7$, $G^8$, $G^9$ and $G^{10}$ are independently selected from N and C(R$^9$), or O, S, N(R$^9$) and C(R$^9$)(R$^{10}$), in accordance with the valency;
wherein the selection of $G^1$ to $G^{10}$ results in a stable aromatic group Z,
and wherein R$^9$ and R$^{10}$ are independently selected from the group consisting of:
(1) C$_{1-6}$ alkyl,
(2) C$_{3-6}$ cycloalkyl,
(3) C$_{1-6}$ haloalkyl,
(4) OH,
(5) O—C$_{1-6}$ alkyl,
(6) O—C$_{1-6}$ haloalkyl,
(7) O—C$_{3-6}$ cycloalkyl,
(8) SH,
(9) S—C$_{1-6}$ alkyl,
(10) S—C$_{1-6}$ haloalkyl,
(11) S—C$_{3-6}$ cycloalkyl,
(12) halo,
(13) CN,
(14) NO$_2$,
(15) NH$_2$,
(16) N(H)—C$_{1-6}$ alkyl,
(17) N(—C$_{1-6}$ alkyl)$_2$,
(18) N(H)C(O)—C$_{1-6}$ alkyl,
(19) N(H)CH(O),
(20) CH(O),
(21) C(O)—C$_{1-6}$ alkyl,
(22) C(O)OH,
(23) C(O)O—C$_{1-6}$ alkyl,
(24) C(O)NH$_2$,
(25) C(O)N(H)—C$_{1-6}$ alkyl,
(26) C(O)N(—C$_{1-6}$ alkyl)$_2$,
(27) C(O)N(H)C(O)—C$_{1-6}$ alkyl,
(28) C(O)N(H)CH(O)
(29) SO$_2$H,
(30) SO$_2$—C$_{1-6}$ alkyl;
(31) phenyl, benzyl or phenoxy, each optionally substituted with 1 to 5 substituents selected from halogen and C$_{1-6}$ alkyl,
(32) HetA, —O-HetA or —CH$_2$—HetA, optionally substituted with 1 to 5 substituents selected from halogen and C$_{1-6}$ alkyl,
(33) trimethylsilyl, and
(34) C$_{2-6}$alkenyl,
wherein C$_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
(a) C$_{1-6}$ haloalkyl,
(b) OH
(c) O—C$_{1-6}$ alkyl,
(d) O—C$_{1-6}$ haloalkyl,
(e) O—C$_{3-6}$ cycloalkyl,
(f) SH,
(g) S—C$_{1-6}$ alkyl,
(h) halo,
(i) CN,
(j) NO$_2$,
(k) NH$_2$,
(l) N(H)—C$_{1-6}$ alkyl,
(m) N(—C$_{1-6}$ alkyl)$_2$,
(n) C(O)—C$_{1-6}$ alkyl,
(o) C(O)OH,
(p) C(O)O—C$_{1-6}$ alkyl, and
(q) SO$_2$—C$_{1-6}$ alkyl, or R$^9$ and R$^{10}$ on the same atom may be joined together to form carbonyl.

9. The compound according to claim 8, or a pharmaceutically acceptable salt thereof, wherein R$^9$ and R$^{10}$ are independently selected from the group consisting of: C$_{1-4}$ alkyl, C$_{1-6}$ haloalkyl, OH, O—C$_{1-6}$ alkyl, halo, CN, SO$_2$—C$_{1-6}$ alkyl, phenyl and benzyl.

10. The compound according to claim 7, or a pharmaceutically acceptable salt thereof, wherein Z is selected from benzimidazolyl, imidazolyl, triazolyl, tetrazolyl, oxadiazolyl, indolyl and pyrrolopyrdidinyl, wherein Z is optionally substituted from one up to the maximum number of substitutable positions as allowed by valence with one or more substituents selected from C$_{1-4}$ alkyl, C$_{1-6}$ haloalkyl, OH, O—C$_{1-6}$ alkyl, halo, CN, SO$_2$—C$_{1-6}$ alkyl, phenyl and benzyl.

11. A compound selected from the group consisting of:
N-(2-{2-[(2R,5R)-5-(1H-benzimidazol-2-yl)morpholin-2-yl]ethyl}phenyl)-Nα-(methoxycarbonyl)-β-phenyl-L-phenylalaninamide;
methyl N-[(1S)-1-benzhydryl-2-[[2-[2-[(2R,5R)-5-(1-methylbenzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(7-methyl-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-methyl-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(3H-imidazo[4,5-c]pyridin-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-methoxy-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-methylsulfonyl-1H-benzimidazol-2-yl)morpholin-2-yl]ethyl]phenyl]amino]-2-oxo-ethyl]carbamate;
methyl N-[(1S)-1-benzhydryl-2-oxo-2-[[2-[2-[(2R,5R)-5-[6-(trifluoromethyl)-1H-benzimidazol-2-yl]morpholin-2-yl]ethyl]phenyl]amino]ethyl]carbamate;
methyl N-[(1S)-1-benzhydryl-2-[[2-[2-[(2R,5R)-5-(5,6-dimethyl-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-cyano-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-bromo-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(5,6-dichloro-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(7-chloro-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(7-bromo-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(4-hydroxy-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(5,6-difluoro-1H-benzimidazol-2-yl)morpholin-2-yl]ethyl]phenyl]amino]-2-oxo-ethyl]carbamate;
methyl N-[(1S)-1-benzhydryl-2-oxo-2-[[2-[2-[(2R,5R)-5-(4,5,6-trifluoro-1H-benzimidazol-2-yl)morpholin-2-yl]ethyl]phenyl]amino]ethyl]carbamate;
methyl N-[(1S)-1-benzhydryl-2-[[2-[2-[(2R,5R)-5-(6-fluoro-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(4-bromo-6-methyl-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-bromo-5-fluoro-1H-benzimidazol-2-yl)morpholin-4-ium-2-yl]ethyl]phenyl]amino]-2-oxo-ethyl]carbamate;
methyl N-[(1S)-1-benzhydryl-2-[[2-[2-[(2R,5R)-5-(3H-imidazo[4,5-b]pyrazin-2-yl)morpholin-2-yl]ethyl]phenyl]amino]-2-oxo-ethyl]carbamate;
methyl N-[(1S)-1-benzhydryl-2-[[2-[2-[(2R,5R)-5-(5-chloro-6-methyl-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(7-methyl-3H-imidazo[4,5-b]pyridin-2-yl)morpholin-2-yl]ethyl]phenyl]amino]-2-oxo-ethyl]carbamate;
methyl N-[(1S)-1-benzhydryl-2-[[2-[2-[(2R,5R)-5-(6-chloro-4-methyl-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-(4,6-dichloro-1H-benzimidazol-2-yl)morpholin-2-yl]ethyl]phenyl]amino]-2-oxo-ethyl]carbamate;
methyl N-[(1S)-1-benzhydryl-2-[[2-[2-[(2R,5R)-5-[4-chloro-6-(trifluoromethyl)-1H-benzimidazol-2-yl]morpholin-2-yl]ethyl]phenyl]amino]-2-oxo-ethyl]carbamate;
N-(2-{2-[(2R,5R)-5-(6-chloro-5-fluoro-1H-benzimidazol-2-yl)morpholin-2-yl]ethyl}phenyl)-Nα-(methoxycarbonyl)-b-phenyl-L-phenylalaninamide;
N-(2-{2-[(2R,5R)-5-(4-fluoro-1H-benzimidazol-2-yl)morpholin-2-yl]ethyl}phenyl)-Nα-(methoxycarbonyl)-b-phenyl-L-phenylalaninamide;
N-(2-{2-[(2R,5R)-5-(5,6-dimethyl-1H-benzimidazol-2-yl)morpholin-2-yl]ethyl}-3-fluorophenyl)-Nα-(methoxycarbonyl)-b-phenyl-L-phenylalaninamide;
methyl N-[(1S)-1-benzhydryl-2-[[4-[2-[(2R,5R)-5-(5,6-dimethyl-1H-benzimidazol-2-yl)morpholin-2-yl]ethyl]-3-pyridyl]amino]-2-oxo-ethyl]carbamate;
methyl N-[(1S)-1-benzhydryl-2-[[4-[2-[(2R,5R)-5-(5,6-dimethyl-1H-benzimidazol-2-yl)morpholin-2-yl]ethyl]-5-fluoro-3-pyridyl]amino]-2-oxo-ethyl]carbamate;
methyl N-[(1S)-1-benzhydryl-2-[[4-[2-[(2R,5R)-5-(5,6-dimethyl-1H-benzimidazol-2-yl)morpholin-2-yl]ethyl]-3-pyridyl]amino]-2-oxo-ethyl]carbamate;
1-[(2-chlorophenyl)methyl]-N-[4-[2-[(2R,5R)-5-(5,6-dimethyl-1H-benzimidazol-2-yl)morpholin-2-yl]ethyl]-5-fluoro-3-pyridyl]cyclopropanecarboxamide;
N-(4-{2-[(2R,5R)-5-(5,6-dimethyl-1H-benzimidazol-2-yl)morpholin-2-yl]ethyl}-2-oxo-1,2-dihydropyridin-3-yl)-β-phenyl-L-phenylalaninamide;
methyl N-[(1S)-1-benzhydryl-2-[[4-[2-[(2R,5R)-5-(5,6-dimethyl-1H-benzimidazol-2-yl)morpholin-2-yl]ethyl]-2-oxo-1H-pyridin-3-yl]amino]-2-oxo-ethyl]carbamate;
Nα-(methoxycarbonyl)-N-[2-(2-{(2R,5R)-5-[(5-methyl-4H-1,2,4-triazol-3-yl)]morpholin-2-yl}ethyl)phenyl]-β-phenyl-L-phenylalaninamide;
methyl [(1S)-2-[(2-{2-[(2R,5R)-5-cyanomorpholin-2-yl]ethyl}phenyl)amino]-1-(diphenylmethyl)-2-oxoethyl]carbamate;

Nα-(methoxycarbonyl)-β-phenyl-N-(2-{2-[(2R,5R)-5-(1H-tetrazol-5-yl)morpholin-2-yl]ethyl}phenyl)-L-phenylalaninamide;

methyl [(1S)-2-[(2-{2-[(2R,5R)-5-(1-benzyl-1H-tetrazol-5-yl)morpholin-2-yl]ethyl}phenyl)amino]-1-(diphenylmethyl)-2-oxoethyl]carbamate;

methyl [(1S)-2-[(2-{2-[(2R,5R)-5-(2-benzyl-2H-tetrazol-5-yl)morpholin-2-yl]ethyl}phenyl)amino]-1-(diphenylmethyl)-2-oxoethyl]carbamate;

methyl {(1S)-1-(diphenylmethyl)-2-[(2-{2-[(2R,5R)-5-(1,2,4-oxadiazol-3-yl)morpholin-2-yl]ethyl}phenyl)amino]-2-oxoethyl}carbamate;

methyl {(1S)-1-(diphenylmethyl)-2-[(2-{2-[(2R,5R)-5-(1H-imidazol-2-yl)morpholin-2-yl]ethyl}phenyl)amino]-2-oxoethyl}carbamate;

methyl {(1S)-1-(diphenylmethyl)-2-[(2-{2-[(2R,5R)-5-(5-methyl-1H-imidazol-2-yl)morpholin-2-yl]ethyl}phenyl)amino]-2-oxoethyl}carbamate;

N-(2-{2-[(2R,5R)-5-(5-benzyl-1H-imidazol-2-yl)morpholin-2-yl]ethyl}phenyl)-Nα-(methoxycarbonyl)-β-phenyl-L-phenylalaninamide;

Nα-(methoxycarbonyl)-β-phenyl-N-(2-{2-[(2R,5R)-5-(5-phenyl-1H-imidazol-2-yl)morpholin-2-yl]ethyl}phenyl)-L-phenylalaninamide;

Nα-(methoxycarbonyl)-β-phenyl-N-(2-{2-[(2R,5R)-5-(2-phenyl-1H-imidazol-5-yl)morpholin-2-yl]ethyl}phenyl)-L-phenylalaninamide;

Nα-(methoxycarbonyl)-N-(2-{2-[(2R,5R)-5-(2-methyl-1H-imidazol-5-yl)morpholin-2-yl]ethyl}phenyl)-β-phenyl-L-phenylalaninamide;

N-(2-{2-[(2R,5R)-5-(4,5-dimethyl-1H-imidazol-2-yl)morpholin-2-yl]ethyl}phenyl)-Nα-(methoxycarbonyl)-β-phenyl-L-phenylalaninamide;

N-(2-{2-[(2R,5R)-5-ethynylmorpholin-2-yl]ethyl}phenyl)-Nα-(methoxycarbonyl)-β-phenyl-L-phenylalaninamide;

N-(2-{2-[(2R,5R)-5-(1-benzyl-1H-1,2,3-triazol-4-yl)morpholin-2-yl]ethyl}phenyl)-Nα-(methoxycarbonyl)-β-phenyl-L-phenylalaninamide;

N-(2-{2-[(2R,5R)-5-(1-benzyl-1H-1,2,3-triazol-5-yl)morpholin-2-yl]ethyl}phenyl)-Nα-(methoxycarbonyl)-β-phenyl-L-phenylalaninamide;

Nα-(methoxycarbonyl)-β-phenyl-N-(2-{2-[(2R,5R)-5-(1H-1,2,3-triazol-5-yl)morpholin-2-yl]ethyl}phenyl)-L-phenylalaninamide;

N-(2-{2-[(2R,5R)-5-(1H-indol-2-yl)morpholin-2-yl]ethyl}phenyl)-Nα-(methoxycarbonyl)-β-phenyl-L-phenylalaninamide;

Nα-(methoxycarbonyl)-N-(2-{2-[(2R,5R)-5-(5-methyl-1H-indol-2-yl)morpholin-2-yl]ethyl}phenyl)-β-phenyl-L-phenylalaninamide;

Nα-(methoxycarbonyl)-β-phenyl-N-[2-(2-{(2R,5R)-5-[5-(trifluoromethyl)-1H-indol-2-yl]morpholin-2-yl}ethyl)phenyl]-L-phenylalaninamide;

Nα-(methoxycarbonyl)-N-(2-{2-[(2R,5R)-5-(5-methoxy-1H-indol-2-yl)morpholin-2-yl]ethyl}phenyl)-β-phenyl-L-phenylalaninamide;

N-(2-{2-[(2R,5R)-5-(5-chloro-1H-indol-2-yl)morpholin-2-yl]ethyl}phenyl)-Nα-(methoxycarbonyl)-β-phenyl-L-phenylalaninamide;

N-(2-{2-[(2R,5R)-5-(6-chloro-1H-indol-2-yl)morpholin-2-yl]ethyl}phenyl)-Nα-(methoxycarbonyl)-β-phenyl-L-phenylalaninamide;

N-(2-{2-[(2R,5R)-5-(7-chloro-1H-indol-2-yl)morpholin-2-yl]ethyl}phenyl)-Nα-(methoxycarbonyl)-β-phenyl-L-phenylalaninamide;

N-(2-{2-[(2R,5R)-5-(4-chloro-1H-indol-2-yl)morpholin-2-yl]ethyl}phenyl)-Nα-(methoxycarbonyl)-β-phenyl-L-phenylalaninamide;

Nα-(methoxycarbonyl)-β-phenyl-N-(2-{2-[(2R,5R)-5-(1H-pyrrolo[3,2-c]pyridin-2-yl)morpholin-2-yl]ethyl}phenyl)-L-phenylalaninamide;

Nα-(methoxycarbonyl)-β-phenyl-N-(2-{2-[(2R,5R)-5-(1H-pyrrolo[2,3-b]pyridin-2-yl)morpholin-2-yl]ethyl}phenyl)-L-phenylalaninamide;

(3S)—N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)-3-(3-fluoropyridin-4-yl)propanamide;

(3S)-3-(3,5-difluorophenyl)-N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)propanamide;

(3S)—N-(4-{2-[(2R,5R)-5-(6-chloro-1H-benzimidazol-2-yl)morpholin-2-yl]ethyl}-5-fluoropyridin-3-yl)-3-(3,5-difluorophenyl)-3-(4-fluorophenyl)propanamide;

(3S)-3-(3,5-difluorophenyl)-N-(5-fluoro-4-{2-[(2R,5R)-5-(6-methyl-1H-benzimidazol-2-yl)morpholin-2-yl]ethyl}pyridin-3-yl)-3-(4-fluorophenyl)propanamide;

(3R)-3-(4-chloro-3-fluorophenyl)-N-(4-{2-[(2R,5R)-5-(5,6-dimethyl-1H-benzimidazol-2-yl)morpholin-2-yl]ethyl}-5-fluoropyridin-3-yl)-3-(3-fluorophenyl)propanamide;

(3S)-3-(4-chloro-3-fluorophenyl)-N-(4-{2-[(2R,5R)-5-(5,6-dimethyl-1H-benzimidazol-2-yl)morpholin-2-yl]ethyl}-5-fluoropyridin-3-yl)-3-(5-fluoropyridin-3-yl)propanamide;

(3R)—N-(4-{2-[(2R,5R)-5-(5,6-dimethyl-1H-benzimidazol-2-yl)morpholin-2-yl]ethyl}-5-fluoropyridin-3-yl)-3-(4-fluorophenyl)-3-phenylpropanamide;

(3R)—N-(4-{2-[(2R,5R)-5-(5,6-difluoro-1H-benzimidazol-2-yl)morpholin-2-yl]ethyl}-5-fluoropyridin-3-yl)-3-(4-fluorophenyl)-3-phenylpropanamide;

(3R)—N-(4-{2-[(2R,5R)-5-(1H-benzimidazol-2-yl)morpholin-2-yl]ethyl}-5-fluoropyridin-3-yl)-3-(4-fluorophenyl)-3-phenylpropanamide;

N-(4-{2-[(2R,5R)-5-(1H-benzimidazol-2-yl)morpholin-2-yl]ethyl}-5-fluoropyridin-3-yl)-4-fluoro-β-(4-fluorophenyl)-Nα-(methoxycarbonyl)-L-phenylalaninamide;

(3S)—N-(2-{2-[(2R,5R)-5-(1H-benzimidazol-2-yl)morpholin-2-yl]ethyl}-3-fluorophenyl)-3-(4-fluorophenyl)-3-(3-fluoropyridin-4-yl)propanamide;

N-(4-{2-[(2R,5R)-5-(1H-benzimidazol-2-yl)morpholin-2-yl]ethyl}-5-fluoropyridin-3-yl)-4-fluoro-β-(4-fluorophenyl)-L-phenylalaninamide;

N-(4-{2-[(2R,5R)-5-(5,6-difluoro-1H-benzimidazol-2-yl)morpholin-2-yl]ethyl}-5-fluoropyridin-3-yl)-4-fluoro-β-(4-fluorophenyl)-L-phenylalaninamide;

N-(4-{2-[(2R,5R)-5-(5,6-difluoro-1H-benzimidazol-2-yl)morpholin-2-yl]ethyl}-5-fluoropyridin-3-yl)-4-fluoro-β-(4-fluorophenyl)-Nα-(methoxycarbonyl)-L-phenylalaninamide;

Nα-(methoxycarbonyl)-β-phenyl-N-(2-{2-[(2R,5R)-5-(1H-tetrazol-5-yl)morpholin-2-yl]ethyl}phenyl)-L-phenylalaninamide;

N-(2-{2-[(2R,5S)-5-(5-benzyl-1,3,4-oxadiazol-2-yl)morpholin-2-yl]ethyl}phenyl)-Nalpha-(methoxycarbonyl)-β-phenyl-L-phenylalaninamide;

N-[2-(2-{(2R,5S)-5-[5-(4-fluorophenyl)-1,3,4-oxadiazol-2-yl]morpholin-2-yl}ethyl)phenyl]-Nalpha-(methoxycarbonyl)-β-phenyl-L-phenylalaninamide;

Nalpha-(methoxycarbonyl)-N-(2-{2-[(2R,5S)-5-(5-methyl-1,3,4-oxadiazol-2-yl)morpholin-2-yl]ethyl}phenyl)-β-phenyl-L-phenylalaninamide;

N-(2-{2-[(2R,5R)-5-(5-benzyl-4H-1,2,4-triazol-3-yl)morpholin-2-yl]ethyl}phenyl)-Nalpha-(methoxycarbonyl)-β-phenyl-L-phenylalaninamide;

Nalpha-(methoxycarbonyl)-N-(2-{2-[(2R,5S)-5-(1,3,4-oxadiazol-2-yl)morpholin-2-yl]ethyl}phenyl)-β-phenyl-L-phenylalaninamide;

Nalpha-(methoxycarbonyl)-N-(2-{2-[(2R,5R)-5-(2-methyl-1,3-thiazol-4-yl)morpholin-2-yl]ethyl}phenyl)-β-phenyl-L-phenylalaninamide;

N-(2-{2-[(2R,5R)-5-(2-benzyl-1,3-thiazol-4-yl)morpholin-2-yl]ethyl}phenyl)-Nalpha-(methoxycarbonyl)-β-phenyl-L-phenylalaninamide;

N-(2-{2-[(2R,5R)-5-(5,6-dichloro-1H-benzimidazol-2-yl)morpholin-2-yl]ethyl}phenyl)-Nalpha-(methoxycarbonyl)-β-phenyl-L-phenylalaninamide;

N-(2-{2-[(2R,5R)-5-(1H-imidazol-2-yl)morpholin-2-yl]ethyl}phenyl)-Nalpha-(methoxycarbonyl)-β-phenyl-L-phenylalaninamide;

N-(2-{2-[(2R,5R,6S)-5-(1H-imidazol-2-yl)-6-{[(5-pyridin-4-yl-1,3,4-oxadiazol-2-yl)sulfanyl]methyl}morpholin-2-yl]ethyl}phenyl)-Nalpha-(methoxycarbonyl)-β-phenyl-L-phenylalaninamide;

Nalpha-(methoxycarbonyl)-N-(2-{2-[(2R,5R)-5-(1-methyl-2-oxo-2, 3-dihydro-1H-imidazol-4-yl)morpholin-2-yl]ethyl}phenyl)-β-phenyl-L-phenylalaninamide;

N-(2-{2-[(2R,5R)-5-(5-hydroxy-3H-imidazo[4,5-b]pyridin-2-yl)morpholin-2-yl]ethyl}phenyl)-Nalpha-(methoxycarbonyl)-β-phenyl-L-phenylalaninamide;

N-[(2-{(3R,6R)-6-[2-(2-{[N-(methoxycarbonyl)-β-phenyl-L-phenylalanyl]amino}phenyl)ethyl]morpholin-3-yl}-1H-indol-3-yl)methylidene]-N-methylmethanaminium;

N-(4-{2-[(2R,5R)-5-(1H-benzimidazol-2-yl)morpholin-2-yl]ethyl}-5-fluoropyridin-3-yl)-4-fluoro-β-(4-fluorophenyl)-L-phenylalaninamide;

N-(4-{2-[(2R,5R)-5-(5,6-dimethyl-1H-benzimidazol-2-yl)morpholin-2-yl]ethyl}-5-fluoropyridin-3-yl)-4-fluoro-β-(4-fluorophenyl)-L-phenylalaninamide;

N-(4-{2-[(2R,5R)-5-(5,6-difluoro-1H-benzimidazol-2-yl)morpholin-2-yl]ethyl}-5-fluoropyridin-3-yl)-4-fluoro-β-(4-fluorophenyl)-L-phenylalaninamide;

N-(2-{[(2S,5R)-5-(1H-benzimidazol-2-yl)morpholin-2-yl]methoxy}-3-fluorophenyl)-β-phenyl-L-phenylalaninamide;

N-(4-{2-[(2R,5R)-5-(5,6-dimethyl-1H-benzimidazol-2-yl)morpholin-2-yl]ethyl}-5-fluoropyridin-3-yl)-4-fluoro-β-(4-fluorophenyl)-Nalpha-(methoxycarbonyl)-L-phenylalaninamide;

methyl 2-[(3R,6R)-6-(2-{3-fluoro-5-[(β-phenyl-L-phenylalanyl)amino]pyridin-4-yl}ethyl)morpholin-3-yl]-1H-benzimidazole-5-carboxylate;

N-(2-{2-[(2R,5R)-5-(1H-benzimidazol-2-yl)morpholin-2-yl]ethyl}-3-fluorophenyl)-3,3-bis(4-fluorophenyl)propanamide;

(3S)—N-(2-{2-[(2R,5R)-5-(1H-benzimidazol-2-yl)morpholin-2-yl]ethyl}-3-fluorophenyl)-3-(2,4-difluorophenyl)-3-(4-fluorophenyl)propanamide;

N-(2-{2-[(2R,5R)-5-(1H-benzimidazol-2-yl)morpholin-2-yl]ethyl}-3-fluorophenyl)-3-(2-chlorophenyl)propanamide;

N-(2-{2-[(2R,5R)-5-(1H-benzimidazol-2-yl)morpholin-2-yl]ethyl}-3-fluorophenyl)-3,3-diphenylpropanamide;

N-(5-fluoro-4-{2-[(2R,5R)-5-{5-[(2,2,2-trifluoroethyl)carbamoyl]-1H-benzimidazol-2-yl}morpholin-2-yl]ethyl}pyridin-3-yl)-β-phenyl-L-phenylalaninamide;

N-(2-{2-[(2R,5R)-5-(1H-benzimidazol-2-yl)morpholin-2-yl]ethyl}-3-fluorophenyl)-2-chloro-L-phenylalaninamide;

N-(2-{2-[(2R,5R)-5-(1H-benzimidazol-2-yl)morpholin-2-yl]ethyl}-3-fluorophenyl)-2-(2-chlorophenoxy)acetamide; or (3S)-3-(3, 5-difluorophenyl)-N-(2-{[(2S,5R)-5-(5,6-dimethyl-1H-benzimidazol-2-yl)morpholin-2-yl]methoxy}-3-fluorophenyl)-3-(4-fluorophenyl)propanamide;

or a pharmaceutically acceptable salt thereof.

12. A pharmaceutical composition comprising a compound according to claim 1 or a pharmaceutically acceptable salt thereof, and a pharmaceutically acceptable carrier.

13. A method for the treatment or prophylaxis of infection by HIV or for the treatment, prophylaxis, or delay in the onset of AIDS in a subject in need thereof, which comprises administering to the subject an effective amount of the compound according to claim 1 or a pharmaceutically acceptable salt thereof.

14. The pharmaceutical composition of claim 12 further comprising an anti-HIV agent selected from the group consisting of HIV antiviral agents, immunomodulators, and anti-infective agents.

15. The pharmaceutical composition of claim 14, wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

* * * * *

UNITED STATES PATENT AND TRADEMARK OFFICE
CERTIFICATE OF CORRECTION

PATENT NO. : 9,737,545 B2
APPLICATION NO. : 15/104782
DATED : August 22, 2017
INVENTOR(S) : John A. McCauley et al.

Page 1 of 1

It is certified that error appears in the above-identified patent and that said Letters Patent is hereby corrected as shown below:

On the Title Page

Column 1, in item (72) in the inventors field:
Please replace "Katharine M. Holloway" with -- M. Katharine Holloway --,
and
Please replace "Helen Juteau" with -- Helene Juteau --

Signed and Sealed this
Tenth Day of July, 2018

Andrei Iancu
*Director of the United States Patent and Trademark Office*